(12) United States Patent
Swayze et al.

(10) Patent No.: US 8,569,264 B2
(45) Date of Patent: *Oct. 29, 2013

(54) ANTIBACTERIAL 4,5-SUBSTITUTED AMINOGLYCOSIDE ANALOGS HAVING MULTIPLE SUBSTITUENTS

(75) Inventors: Eric E. Swayze, Encinitas, CA (US); Stephen Hanessian, Beaconsfield (CA); Janek Szychowski, Val Belair (CA); Susanta Sekhar Adhikari, Calcutta (IN); Kandasamy Pachamuthu, North York (CA); Xiaojing Wang, Foster City, CA (US); Michael T. Migawa, Carlsbad, CA (US); Richard H. Griffey, Vista, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/344,247

(22) Filed: Jan. 5, 2012

(65) Prior Publication Data

US 2013/0005674 A1  Jan. 3, 2013

Related U.S. Application Data

(63) Continuation of application No. 12/987,842, filed on Jan. 10, 2011, now Pat. No. 8,114,856, which is a continuation of application No. 12/130,048, filed on May 30, 2008, now Pat. No. 7,893,039, which is a continuation of application No. PCT/US2006/046122, filed on Dec. 1, 2006.

(60) Provisional application No. 60/742,051, filed on Dec. 2, 2005.

(51) Int. Cl.
*A01N 43/04* (2006.01)
*A61K 31/715* (2006.01)

(52) U.S. Cl.
USPC ............................ 514/61; 514/23; 514/54

(58) Field of Classification Search
None
See application file for complete search history.

(56) References Cited

U.S. PATENT DOCUMENTS

| | | | |
|---|---|---|---|
| 3,808,198 A | 4/1974 | Naito et al. |
| 3,860,574 A | 1/1975 | Naito et al. |
| 3,896,106 A | 7/1975 | Naito et al. |
| 3,897,412 A | 7/1975 | Naito et al. |
| 3,956,274 A | 5/1976 | Umezawa et al. |
| 4,021,601 A | 5/1977 | Arcamone et al. |
| 4,066,753 A | 1/1978 | Hanessian |
| 4,078,138 A | 3/1978 | Akita et al. |
| 4,170,642 A | 10/1979 | Umezawa et al. |
| 4,247,687 A | 1/1981 | Hanessian |
| 4,337,248 A | 6/1982 | Battistini et al. |
| 4,347,354 A | 8/1982 | Cron et al. |
| 4,424,343 A | 1/1984 | Cron et al. |
| 4,617,293 A | 10/1986 | Wahlig et al. |
| 4,937,257 A | 6/1990 | Gericke et al. |
| 5,470,836 A | 11/1995 | Donno et al. |
| 5,534,408 A | 7/1996 | Green et al. |
| 5,763,587 A | 6/1998 | Mangia |
| 5,935,776 A | 8/1999 | Green et al. |
| 5,942,547 A | 8/1999 | Gustafson et al. |
| 6,140,361 A | 10/2000 | Gustafson et al. |
| 6,541,456 B1 | 4/2003 | Swayze et al. |
| 6,759,523 B2 | 7/2004 | Swayze et al. |
| 6,967,242 B2 | 11/2005 | Swayze et al. |
| 7,893,039 B2 | 2/2011 | Swayze et al. |
| 8,114,856 B2 | 2/2012 | Swayze et al. |
| 8,318,685 B2 | 11/2012 | Goldblum et al. |
| 8,367,625 B2 | 2/2013 | Aggen et al. |
| 8,372,813 B2 | 2/2013 | Aggen et al. |
| 8,377,896 B2 | 2/2013 | Migawa et al. |
| 8,383,596 B2 | 2/2013 | Aggen et al. |
| 8,399,419 B2 | 3/2013 | Aggen et al. |
| 2004/0229265 A1 | 11/2004 | Lapidot et al. |
| 2005/0004052 A1 | 1/2005 | Baasov et al. |
| 2005/0148522 A1 | 7/2005 | Baasov et al. |
| 2008/0045468 A1 | 2/2008 | Hanessian et al. |
| 2008/0214845 A1 | 9/2008 | Migawa et al. |
| 2008/0293649 A1 | 11/2008 | Swayze et al. |
| 2008/0300199 A1 | 12/2008 | Linsell et al. |
| 2010/0099661 A1 | 4/2010 | Aggen et al. |
| 2011/0166334 A1 | 7/2011 | Swayze et al. |
| 2011/0245476 A1 | 10/2011 | Migawa et al. |
| 2011/0275586 A1 | 11/2011 | Aggen et al. |
| 2011/0288041 A1 | 11/2011 | Aggen et al. |
| 2012/0122809 A1 | 5/2012 | Goldblum et al. |
| 2012/0135945 A1 | 5/2012 | Dozzo et al. |
| 2012/0135946 A1 | 5/2012 | Goldblum et al. |
| 2012/0135948 A1 | 5/2012 | Goldblum et al. |

(Continued)

FOREIGN PATENT DOCUMENTS

| | | |
|---|---|---|
| CA | 1 271 744 | 7/1990 |
| DE | 25 15 629 A1 | 10/1975 |

(Continued)

OTHER PUBLICATIONS

Alper et al., "Metal Catalyzed Diazo Transfer for the Synthesis of Azides From Amines," *Tetrahedron Letters* 37(34):6029-6032, 1996.
Alper et al., "Probing the Specificity of Aminoglycoside-Ribosomal RNA Interactions with Designed Synthetic Analogs," *J. Am. Chem. Soc.* 120(9):1965-1978, 1998.
Battistini et al., "Semisynthetic Aminoglycoside Antibiotics. IV 3',4'-Dideoxyparomomycin and Analogues," *The Journal of Antibiotics* 35(1):98-101, Jan. 1982.
The Merck Index, twelfth edition. Budavari (ed.), Whitehouse Station: Merck & Co., Inc., Compound 1559, 1996.
Cavender et al., "Trifluoromethanesulfonyl Azide. Its Reaction with Alkyl Amines to Form Alkyl Azides," *J. Org. Chem.* 37(22):3567-3569, 1972.

(Continued)

*Primary Examiner* — Patrick Lewis
(74) *Attorney, Agent, or Firm* — Cooley LLP

(57) ABSTRACT

The present invention is directed to analogs of aminoglycoside compounds as well as their preparation and use as prophylactic or therapeutics against microbial infection.

25 Claims, No Drawings

(56) References Cited

U.S. PATENT DOCUMENTS

| | | | |
|---|---|---|---|
| 2012/0165282 A1 | 6/2012 | Dozzo et al. |
| 2012/0172332 A1 | 7/2012 | Aggen et al. |
| 2012/0184501 A1 | 7/2012 | Dozzo et al. |
| 2012/0196791 A1 | 8/2012 | Armstrong et al. |
| 2012/0208781 A1 | 8/2012 | Bruss et al. |
| 2012/0214759 A1 | 8/2012 | Bruss et al. |
| 2012/0214760 A1 | 8/2012 | Bruss et al. |
| 2012/0258925 A1 | 10/2012 | Aggen et al. |
| 2012/0283207 A1 | 11/2012 | Maianti et al. |
| 2012/0283208 A1 | 11/2012 | Aggen et al. |
| 2012/0283209 A1 | 11/2012 | Dozzo et al. |

FOREIGN PATENT DOCUMENTS

| | | |
|---|---|---|
| DE | 29 36 120 A1 | 3/1980 |
| DE | 30 44 970 A1 | 9/1981 |
| DE | 34 05 326 A1 | 8/1985 |
| EP | 0 021 150 A1 | 1/1981 |
| FR | 1 361 393 | 4/1964 |
| FR | 2 183 236 | 12/1973 |
| GB | 1 400 676 | 7/1975 |
| GB | 1 456 674 | 11/1976 |
| GB | 1 488 420 | 10/1977 |
| GB | 2 068 366 A | 8/1981 |
| GB | 1 600 457 | 10/1981 |
| JP | 49-92044 | 9/1974 |
| JP | 49-101355 | 9/1974 |
| JP | 52-100464 | 8/1977 |
| JP | 55-15445 A | 2/1980 |
| JP | 56-110697 | 9/1981 |
| WO | WO 82/00464 | 2/1982 |
| WO | WO 92/02530 | 2/1992 |
| WO | WO 94/09792 | 5/1994 |
| WO | WO 00/39139 | 7/2000 |
| WO | WO 01/54691 A1 | 8/2001 |
| WO | WO 02/053188 A1 | 7/2002 |
| WO | WO 03/059246 A2 | 7/2003 |
| WO | WO 03/101405 A2 | 12/2003 |
| WO | WO 03/105774 A2 | 12/2003 |
| WO | WO 2005/041984 A1 | 5/2005 |
| WO | WO 2006/052930 A1 | 5/2006 |
| WO | WO 2007/028012 A2 | 3/2007 |
| WO | WO 2007/064954 A2 | 6/2007 |
| WO | WO 2007/088999 A1 | 8/2007 |
| WO | WO 2008/006583 A1 | 1/2008 |
| WO | WO 2008/092690 A1 | 8/2008 |
| WO | WO 2008/124821 A1 | 10/2008 |
| WO | WO 2009/067692 A1 | 5/2009 |
| WO | WO 2010/030690 A1 | 3/2010 |
| WO | WO 2010/030704 A2 | 3/2010 |
| WO | WO 2010/042850 A1 | 4/2010 |
| WO | WO 2010/042851 A1 | 4/2010 |
| WO | WO 2010/132757 A2 | 11/2010 |
| WO | WO 2010/132759 A1 | 11/2010 |
| WO | WO 2010/132760 A1 | 11/2010 |
| WO | WO 2010/132765 A2 | 11/2010 |
| WO | WO 2010/132768 A1 | 11/2010 |
| WO | WO 2010/132770 A1 | 11/2010 |
| WO | WO 2010/132777 A2 | 11/2010 |
| WO | WO 2010/132839 A2 | 11/2010 |
| WO | WO 2010/147836 A1 | 12/2010 |
| WO | WO 2011/044498 A1 | 4/2011 |
| WO | WO 2011/044501 A2 | 4/2011 |
| WO | WO 2011/044502 A1 | 4/2011 |
| WO | WO 2011/044503 A1 | 4/2011 |
| WO | WO 2011/044538 A1 | 4/2011 |
| WO | WO 2012/067978 A1 | 5/2012 |

OTHER PUBLICATIONS

Chen et al., "Structure-toxicity relationship of aminoglycosides: Correlation of 2'-amine basicity with acute toxicity in pseudo-disaccharide scaffolds," *Bioorganic & Medicinal Chemistry* 16:8940-8951, 2008.

Chow et al., "A Structural Basis for RNA-Ligand Interactions," *Chem. Rev.* 97(5):1489-1513, Jul./Aug. 1997.

Ding et al., "Efficient synthesis of neomycin B related aminoglycosides," *Tetrahedron Letters* 41:4049-4052, 2000.

Dozzo et al., "New aminoglycoside antibiotics," *Expert Opin. Ther. Patents* 20(10):1-21, 2010.

François et al., "Antibacterial Aminoglycosides with a Modified Mode of Binding to the Ribosomal-RNA Decoding Site," *Angew. Chem. Int. Ed.* 43:6735-6738, 2004.

Georgiadas et al., "Synthesis of Amino Acid Derivatives of Neamine and 2-Deoxystreptamine to Be Used as Mutasynthons," *J. Carbohydrate Chemistry* 10(5):739-748, 1991.

Greenberg et al., "Design and Synthesis of New Aminoglycoside Antibiotics Containing Neamine as an Optimal Core Structure: Correlation of Antibiotic Activity with in Vitro Inhibition of Translation," *J. Am. Chem. Soc.* 121(28):6527-6541, 1999.

Greene, "Protective Groups in Organic Synthesis," John Wiley & Sons, Inc., New York, p. 29-39, 1981.

Hanessian et al., "Aminoglycoside antibiotics: Chemical conversion of neomycin B, paromomycin, and lividomycin B into bioactive pseudosaccharides," *Canadian Journal of Chemistry* 56(11):1482-1491, Jun. 1, 1978.

Hanessian et al., "Aminoglycoside Antibiotics 4'-Deoxyneomycin and 4'-Deoxyparomamine," *The Journal of Antibiotics* 33(6):675-678, Jun. 1980.

Hanessian et al., "Probing the functional requirements of the L-haba side-chain of amikacin—synthesis, 16S A-site or rRNA binding, and antibacterial activity," *Tetrahedron* 59: 995-1007, 2003.

Hanessian et al., "Probing the ribosomal RNA A-site with functionally diverse analogues of paromomycin—synthesis of ring I mimetics," *Tetrahedron* 63:827-846, 2007.

Hermansky, "Neomycin N-methanesulfonate," Database CAPLUS on STN, Accession No. 60:11121, 1962, 2 pages.

Hoshi et al., "Amikacin Analogs with a Fluorinated Amino Acid Side Chain," *The Journal of Antibiotics* 43(7):858-872, Jul. 1990.

Kane et al., "Basicity of the Amino Groups of the Aminoglycoside Amikacin Using Capillary Electrophoresis and Coupled CE-MS-MS Techniques," *Analytical Chemistry* 73(16):4028-4036, Aug. 15, 2001.

Kondo et al., "Crystal Structure of the Bacterial Ribosomal Decoding Site Complexed with a Synthetic Doubly Functionalized Paromomycin Derivative: a New Specific Binding Mode to an A-Minor Motif Enhances in vitro Antibacterial Activity," *ChemMedChem* 2:1631-1638, 2007.

Kumar et al., "Aminoglycoside Antibiotics. 4. Regiospecific Partial Synthesis of Ribostamycin and 4"-Thioribostamycin," *J. Org. Chem.* 46(21):4298-4300, 1981.

Lesniak et al., "An isocratic separation of underivatized gentamicin components, H NMR assignment and protonation pattern," *Carbohydrate Research* 338:2853-2862, 2003.

Li et al., "Investigation of the Regioselectivity for the Staudinger Reaction and Its Application for the Synthesis of Aminoglycosides with N-1 Modification," *J. Org. Chem.* 72(11):4055-4066, 2007.

Li et al., "Guanidine/Pd(OAc)$_2$-Catalyzed Room Temperature Suzuki Cross-Coupling Reaction in Aqueous Media under Aerobic Conditions," *J. Org. Chem.* 72(11):4067-4072, 2007.

Llewellyn et al., "Chemoenzymatic acylation of aminoglycoside antibiotics," *Chem. Commun.* 32:3786-3788, 2008.

Marrero-Ponce et al., "Non-stochastic and stochastic linear indices of the molecular pseudograph's atom-adjacency matrix: a novel approach for computational in silico screening and "rational" selection of new lead antibacterial agents," *J. Mol. Model.* 12: 255-271, 2006.

Marrero-Ponce et al., "Atom, atom-type, and total nonstochastic and stochastic quadratic fingerprints: a promising approach for modeling of antibacterial activity," *Bioorganic & Medicinal Chemistry* 13:2881-2899, 2005.

Moazed et al., "Interaction of antibiotics with functional sites in 16S ribosomal RNA," *Nature* 327:389-394, Jun. 4, 1987.

Narita et al., "Synthesis and Activity of Butirosin Derivatives with 5"-Amidino and 5"-Guanidino Substituents," *The Journal of Antibiotics* 44(1):86-92, Jan. 1991.

O'Shea et al., "Physicochemical Properties of Antibacterial Compounds: Implications for Drug Discovery," *Journal of Medicinal Chemistry* 51(10):2871-2878, May 22, 2008.

(56) References Cited

OTHER PUBLICATIONS

Pénasse et al., "Sur quelques dérivés mono N-alcoylés de la néomycine et de la paromomycine," *Bulletin de la Société chimique de France* 7:2391-2394, Jul. 1969.
Scholl et al., "Synthesis and Activity of a New Generation of Ruthenium-Based Olefin Metathesis Catalysts Coordinated with 1,3-Dimesityl-4,5-dihydroimidazol-2-ylidene Ligands," *Organic Letters* 1(6):953-956, 1999.
Shier et al., "Chemistry and Biochemistry of the Neomycins. XVI Synthesis and Bioactivity of Hexa-N-Benzylneomycins," *The Journal of Antibiotics* 26(10):547-550, Oct. 1973.
Sunada et al., "Enzymatic 1-N-Acetylation of Paromomycin by an Actinomycete Strain #8 with Multiple Aminoglycoside Resistance and Paromomycin Sensitivity," *The Journal of Antibiotics* 52(9):809-814, Sep. 1999.
Takahashi et al., "Syntheses of 1-Epikanamycin A and Its 1-N-[(S)-4-Amino-2-hydroxybutyryl] Derivative," *Bull. Chem. Soc. Jpn.* 56(6):1807-1811, Jun. 1983.
Takahashi et al., "Study on fluorination-toxicity relationships. Syntheses of 1-N-[(2R,3R)- and (2R,3S)-4-amino-3-fluoro-2-hydroxybutanoyl] derivatives of kanamycins," *Carbohydrate Research* 249:57-76, 1993.
Takahashi et al., "Synthesis of 1-N-[(2S,4S)- and (2S,4R)-5-amino-4-fluoro-2-hydroxypentanoyl]dibekacins (study on structure—toxicity relationships)," *Carbohydrate Research* 306:349-360, 1998.
Takamoto et al., "Aminoglycoside Antibiotics: Chemical Transformation of Paromomycin Into a Bioactive Pseudotrisaccharide," *Tetrahedron Letters* 46:4009-4012, 1974.
Takeda et al., "Mutational Biosynthesis of Butirosin Analogs II. 3',4'-Dideoxy-6'-N-Methylbutirosins, New Semisynthetic Aminoglycosides," *The Journal of Antibiotics* 31(10):1031-1038, Oct. 1978.
Takeda et al., "Mutational Biosynthesis of Butirosin Analogs III. 6'-N-Methylbutirosins and 3',4'-Dideoxy-6'-C-Methylbutirosins, New Semisynthetic Aminoglycosides," *The Journal of Antibiotics* 31(10):1039-1045, Oct. 1978.
Tamura et al., "The Synthesis of Destomycin C, a Typical Pseudo-Trisaccharide of Destomycin-Group Antibiotics," *Carbohydrate Research* 174:181-199, 1988.
Taniyama et al., "Antibiotics Aminosidin. II. Some Amino Derivatives of Aminosidin and Their Biological Activity," *Chem. Pharm. Bull.* 21(3):609-615, Mar. 1973.
Tok et al., "Binding of Aminoglycoside Antibiotics with Modified A-site 16S rRNA Construct Containing Non-Nucleotide Linkers," *Bioorganic & Medicinal Chemistry Letters* 12:365-370, 2002.
Torn et al., Synthesis of 5''-Deoxy-5''-fluorolividomycin B, Bull. Chem. Soc. Jpn. 56, 56(5):1522-1526 1983.
Umezawa et al., "Synthesis and Antibacterial Activity of 6'-N-Alkyl Derivatives of 1-N-[(S)-4-Amino-2-Hydroxybutyryl]-Kanamycin," *The Journal of Antibiotics* 28(6):483-485, Jun. 1975.
Van Straten et al., "An Expeditious Route to the Synthesis of Adenophostin A," *Tetrahedron* 53(18):6509-6522, 1997.
Wallis et al., "The Binding of Antibiotics to RNA," *Prog. Biophys. molec. Biol.* 67(2/3):141-154, 1997.
Watanabe et al., "Syntheses of 6'-Amino-6'-Deoxylividomycin B and 6'-Deoxy-6'-Methylamino- and 6'-Deoxy-6'-(2-Hydroxyethylamino)-Lividomycin B," *The Journal of Antibiotics* 26(12):802-804, Dec. 1973.
Watanabe et al., "Synthesis of 6'-Amino-1-N-[(S)-4-Amino-2-Hydroxybutyryl]-6'-Deoxylividomycin A," *Bulletin of the Chemical Society of Japan* 48(8):2303-2305, Aug. 1975.
Watanabe et al., "Synthesis of 1-N-[(S)-4-Amino-2-hydroxybutyryl]lividomycin A," *Bulletin of the Chemical Society of Japan* 48(7):2124-2126, Jul. 1975.
Watanabe et al., "Synthesis of 1-N-((s)-4-Amino-2-Hydroxybutyryl) Lividomycin A," *The Journal of Antibiotics* 26(5):310-312, May 1973.
Yamasaki et al., "Synthesis and Biological Activity of 1-N-[4-(Substituted)Amidino and Guanidino-2-Hydroxybutyryl]Kanamycins A and B," *The Journal of Antibiotics* 44(6):646-658, Jun. 1991.
Zaloom et al., "Preparation of Azido Derivatives from Amino Acids and Peptides by Diazo Transfer," *J. Org. Chem* 46(25):5173-5176, 1981.
International Search Report for PCT International Application No. PCT/US2005/040364, mailed Mar. 29, 2006, 4 pages.
International Search Report for PCT International Application No. PCT/US2006/034216, mailed May 3, 2007, 5 pages.
International Search Report for PCT International Application No. PCT/US2006/046122, mailed Jun. 21, 2007, 7 pages.
International Search Report for PCT International Application No. PCT/US2008/059904, mailed Jun. 19, 2008, 4 pages.
International Search Report for PCT International Application No. PCT/US2009/056391, mailed Feb. 15, 2010, 7 pages.
International Search Report for PCT International Application No. PCT/US2009/056407, mailed Mar. 30, 2010, 4 pages.
International Search Report for PCT International Application No. PCT/US2009/060211, mailed Dec. 29, 2009, 3 pages.
International Search Report for PCT International Application No. PCT/US2009/060212, mailed Dec. 9, 2009, 2 pages.
International Search Report for PCT International Application No. PCT/US2010/052045, mailed Feb. 17, 2011, 4 pages.
International Search Report for PCT International Application No. PCT/US2010/052109, mailed Feb. 23, 2011, 4 pages.
International Search Report for PCT International Application No. PCT/US2010/052040, mailed Feb. 23, 2011, 3 pages.
International Search Report for PCT International Application No. PCT/US2010/052044, mailed Feb. 23, 2011, 4 pages.
International Search Report for PCT International Application No. PCT/US2010/052043, mailed May 2, 2011, 5 pages.
International Search Report for PCT International Application No. PCT/US2011/060513, mailed Mar. 27, 2011, 4 pages.
Invitation to Pay Additional Fees for PCT International Application No. PCT/US2010/052043, mailed Feb. 24, 2011, 8 pages.
International Preliminary Report on Patentability for PCT/US2005/040364, mailed May 8, 2007, 9 pages.
International Preliminary Report on Patentability for PCT/US2006/034216, mailed Mar. 4, 2008, 8 pages.
International Preliminary Report on Patentability for PCT/US2009/056391, mailed Mar. 15, 2011, 9 pages.
International Preliminary Report on Patentability for PCT/US2006/046122, mailed Jun. 4, 2008, 11 pages.
International Preliminary Report on Patentability for PCT/US2008/059904, mailed Oct. 13, 2009, 7 pages.
International Preliminary Report on Patentability for PCT/US2009/056407, mailed Mar. 15, 2011, 5 pages.
International Preliminary Report on Patentability for PCT/US2009/060212, mailed Apr. 12, 2011, 6 pages.
International Preliminary Report on Patentability for PCT/US2009/060211, mailed Apr. 12, 2011, 7 pages.
International Preliminary Report on Patentability for PCT/US2010/052040, mailed Apr. 19, 2012, 7 pages.
International Preliminary Report on Patentability for PCT/US2010/052043, mailed Apr. 19, 2012, 12 pages.
International Preliminary Report on Patentability for PCT/US2010/052045, mailed Apr. 19, 2012, 7 pages.
International Preliminary Report on Patentability for PCT/US2010/052044, mailed Apr. 19, 2012, 8 pages.
Written Opinion for PCT/US2005/040364,mailed Mar. 29, 2006, 8 pages.
Written Opinion for PCT/US2006/034216, mailed May 3, 2007, 7 pages.
Written Opinion for PCT/US2006/046122, mailed Jun. 21, 2007, 10 pages.
Written Opinion for PCT/US2008/059904, mailed Jun. 19, 2008, 7 pages.
Written Opinion for PCT/US2009/056391, mailed Feb. 15, 2010, 8 pages.
Written Opinion for PCT/US2009/056407, mailed Mar. 30, 2010, 4 pages.

(56) References Cited

OTHER PUBLICATIONS

Written Opinion for PCT/US2009/060211, mailed Dec. 29, 2009, 6 pages.
Written Opinion for PCT/US2009/060212, mailed Dec. 9, 2009, 5 pages.
Written Opinion for PCT/US2010/052045, mailed Feb. 17, 2011, 5 pages.
Written Opinion for PCT/US2010/052109, mailed Feb. 23, 2011, 6 pages.
Written Opinion for PCT/US2010/052040, mailed Feb. 23, 2011, 5 pages.
Written Opinion for PCT/US2010/052043, mailed May 2, 2011, 10 pages.
Written Opinion for PCT/US2010/052044, mailed Feb. 23, 2011, 8 pages.
Written Opinion for PCT/US2011/060513, mailed Mar. 27, 2011, 7 pages.
Non-Final Office Action for U.S. Appl. No. 12/040,615, mailed Jan. 27, 2009, 6 pages.
Non-Final Office Action for U.S. Appl. No. 12/040,615, mailed Jun. 25, 2009, 16 pages.
Notice of Abandonment for U.S. Appl. No. 12/040,615, mailed Feb. 3, 2010, 3 pages.
Non-Final Office Action for U.S. Appl. No. 13/044,226, mailed May 15, 2012, 5 pages.
Non-Final Office Action for U.S. Appl. No. 09/452,606, mailed Jul. 13, 2001, 13 pages.
Office Communication for U.S. Appl. No. 09/452,606, mailed Dec. 21, 2001, 4 pages.
Final Office Action for U.S. Appl. No. 09/452,606, mailed May 7, 2002, 7 pages.
Office Communication for U.S. Appl. No. 09/452,606, mailed Feb. 5, 2003, 3 pages.
Advisory Action for U.S. Appl. No. 09/452,606, mailed Aug. 5, 2002, 3 pages.
Notice of Allowance and Fee(s) Due for U.S. Appl. No. 09/452,606, mailed Oct. 21, 2002, 3 pages.
Issue Notification for U.S. Appl. No. 09/452,606, mailed Mar. 12, 2003, 1 page.
Non-Final Office Action for U.S. Appl. No. 09/727,315, mailed Sep. 23, 2002, 7 pages.
Non-Final Office Action for U.S. Appl. No. 09/727,315, mailed Jan. 14, 2003, 10 pages.
Final Office Action for U.S. Appl. No. 09/727,315, mailed Apr. 28, 2003, 7 pages.
Notice of Allowance and Fee(s) Due for U.S. Appl. No. 09/727,315, mailed Aug. 25, 2003, 7 pages.
Notice of Allowance and Fee(s) Due for U.S. Appl. No. 09/727,315, mailed Jan. 28, 2004, 3 pages.
Issue Notification for U.S. Appl. No. 09/727,315, mailed Jun. 17, 2004, 1 page.
Non-Final Office Action for U.S. Appl. No. 10/299,220, mailed Nov. 3, 2003, 11 pages.
Notice of Non-Compliant Amendment (37 CFR 1.121) for U.S. Appl. No. 10/299,220, mailed Feb. 10, 2004, 2 pages.
Final Office Action for U.S. Appl. No. 10/299,220, mailed May 13, 2004, 10 pages including Appendices A-C.
Advisory Action for U.S. Appl. No. 10/299,220, mailed Aug. 6, 2004, 3 pages.
Notice of Allowance and Fee(s) Due for U.S. Appl. No. 10/299,220, mailed Oct. 13, 2004, 5 pages.
Response to Rule 312 Communication for U.S. Appl. No. 10/299,220, mailed Ocober 13, 2005, 2 pages.
Issue Notification for U.S. Appl. No. 10/299,220, mailed Nov. 2, 2005, 1 page.
Non-Final Office Action for U.S. Appl. No. 12/130,048, mailed May 27, 2010, 9 pages.
Notice of Allowance and Fee(s) Due for U.S. Appl. No. 12/130,048, mailed Dec. 14, 2010, 4 pages.
Issue Notification for U.S. Appl. No. 12/130,048, mailed Feb. 2, 2011, 1 page.
Non-Final Office Action for U.S. Appl. No. 12/100,981, mailed Nov. 27, 2009, 10 pages.
Non-Final Office Action for U.S. Appl. No. 12/100,981, mailed Feb. 26, 2010, 7 pages.
Final Office Action for U.S. Appl. No. 12/100,981, mailed Oct. 4, 2010, 8 pages.
Non-Final Office Action for U.S. Appl. No. 12/100,981, mailed Nov. 29, 2011, 7 pages.
Final Office Action for U.S. Appl. No. 12/100,981, mailed Jul. 6, 2012, 8 pages.
Non-Final Office Action for U.S. Appl. No. 13/044,234, mailed Apr. 27, 2012, 8 pages.
Notice of Allowance and Fee(s) Due for U.S. Appl. No. 13/082,141, mailed Aug. 6, 2012, 9 pages.
Office Communication enclosing corrected Notice of Allowability for U.S. Appl. No. 13/082,141, mailed Sep. 5, 2012 (3 pages).
Notice of Allowance and Fee(s) Due for U.S. Appl. No. 13/082,143, mailed Aug. 9, 2012, 9 pages.
Notice of Allowance and Fee(s) Due for U.S. Appl. No. 13/295,219, mailed Jul. 30, 2012, 8 pages.
Banker, G.S., et al., "Modern Pharmaceutics, Third Edition, Revised and Expanded," Macel Dekker, Inc., New York, 1996, p. 596.
International Preliminary Report on Patentability for PCT International Application No. PCT/US2010/052109, mailed Apr. 9, 2013 (8 pages).
Non-Final Office Action for U.S. Appl. No. 12/100,981, mailed Feb. 20, 2013 (7 pages).
Non-Final Office Action for U.S. Appl. No. 13/441,693, mailed May 6, 2013 (8 pages).
Non-Final Office Action for U.S. Appl. No. 13/441,696, mailed Sep. 13, 2012 (10 pages).
Non-Final Office Action for U.S. Appl. No. 13/441,699, mailed May 7, 2013 (10 pages).
Non-Final Office Action for U.S. Appl. No. 13/441,701, mailed May 9, 2013 (10 pages).
Non-Final Office Action for U.S. Appl. No. 13/652,163, mailed May 6, 2013 (6 pages).
Notice of Allowance and Fee(s) Due for U.S. Appl. No. 13/044,226, mailed Oct. 18, 2012 (6 pages).
Notice of Allowance and Fee(s) Due for U.S. Appl. No. 13/044,234, mailed Nov. 13, 2012 (5 pages).
Notice of Allowance and Fee(s) Due for U.S. Appl. No. 13/082,141, mailed Oct. 9, 2012 (5 pages).
Notice of Allowance and Fee(s) Due for U.S. Appl. No. 13/082,143, mailed Oct. 9, 2012 (4 pages).
Notice of Allowance and Fee(s) Due for U.S. Appl. No. 13/441,696, mailed Feb. 21, 2013 (5 pages).
Notice of Allowance and Fee(s) Due for U.S. Appl. No. 13/295,219, mailed Oct. 3, 2012 (8 pages).
Wolff, Manfred E., "Burger's Medicinal Chemistry and Drug Discovery, Fifth Edition, vol. 1: Principles and Practice," John Wiley & Sons, Inc., 1995, pp. 975-977.

ANTIBACTERIAL 4,5-SUBSTITUTED AMINOGLYCOSIDE ANALOGS HAVING MULTIPLE SUBSTITUENTS

CROSS-REFERENCES TO RELATED APPLICATIONS

This application is a continuation of U.S. patent application Ser. No. 12/987,842, filed Jan. 10, 2011, which is a continuation of U.S. patent application Ser. No. 12/130,048, filed May 30, 2008, now issued as U.S. Pat. No. 7,893,039, which is a continuation of International PCT Patent Application No. PCT/US2006/046122, which was filed on Dec. 1, 2006, now abandoned, which claims the benefit under 35 U.S.C. §119(e) of U.S. Provisional Patent Application No. 60/742,051 filed Dec. 2, 2005. These applications are incorporated herein by reference in their entireties.

BACKGROUND OF THE INVENTION

1. Field of the Invention

The present invention is directed to novel aminoglycoside compounds and synthetic methods for their preparation and use as therapeutic or prophylactic agents.

2. Description of the Related Art

A particular interest in modern drug discovery is the development of novel low molecular weight orally-bioavailable drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, such proteins can be inhibited by preventing their production in the first place by interfering with the translation of the mRNA. Since both proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein may have the appropriate 3-dimensional shape for drug binding. Preparation of biologically active proteins for screening is a major limitation in classical high throughput screening. Quite often the limiting reagent in high throughput screening efforts is a biologically active form of a protein which can also be quite expensive.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition of RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified as containing only the essential region, and have been shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charges are believed to be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the O4 and O6 oxygen atoms of uridine and guanosine, and the amines of adenosine and cytidine. The rich structural and sequence diversity of RNA suggests to us that ligands can be created with high affinity and specificity for their target.

Although our understanding of RNA structure and folding, as well as the modes in which RNA is recognized by other ligands, is far from being comprehensive, significant progress has been made in the last decade (Chow, C. S.; Bogdan, F. M., Chem. Rev., 1997, 97, 1489, Wallis, M. G.; Schroeder, R., Prog. Biophys. Molec. Biol. 1997, 67, 141). Despite the central role RNA plays in the replication of bacteria, drugs that target these pivotal RNA sites of these pathogens are scarce. The increasing problem of bacterial resistance to antibiotics makes the search for novel RNA binders of crucial importance.

Certain small molecules can bind and block essential functions of RNA. Examples of such molecules include the aminoglycoside antibiotics and drugs such as erythromycin which binds to bacterial rRNA and releases peptidyl-tRNA and mRNA. Aminoglycoside antibiotics have long been known to bind RNA. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (Moazed, D.; Noller, H. F., Nature, 1987, 327, 389). Binding of aminoglycosides to this RNA target interferes with the fidelity of mRNA translation and results in miscoding and truncation, leading ultimately to bacterial cell death (Alper, P. B.; Hendrix, M.; Sears, P.; Wong, C., J. Am. Chem. Soc., 1998, 120, 1965).

There is a need in the art for new chemical entities that work against bacteria with broad-spectrum activity. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA. There are three sets of data that provide hints on how to do this: natural protein interactions with RNA, natural product antibiotics that bind RNA, and man-made RNAs (aptamers) that bind proteins and other molecules. Each data set, however, provides different insights to the problem.

Several classes of drugs obtained from natural sources have been shown to work by binding to RNA or RNA/protein complexes. These include three different structural classes of antibiotics: thiostreptone, the aminoglycoside family and the macrolide family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity these ancient processes fundamental to all bacterial life represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist, these include the aminoglycosides, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code. Misreading of the code during translation of integral membrane proteins is thought to produce abnormal proteins that compromise the barrier properties of the bacterial membrane.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. At the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these agents have also contributed significantly to the rising costs of medical care.

When the antimicrobial activity of a new agent is first tested, a pattern of sensitivity and resistance is usually defined. Unfortunately, this spectrum of activity can subsequently change to a remarkable degree, because microorganisms have evolved the array of ingenious alterations discussed above that allow them to survive in the presence of antibiotics. The mechanism of drug resistance varies from microorganism to microorganism and from drug to drug.

The development of resistance to antibiotics usually involves a stable genetic change, heritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

For the foregoing reasons, there is a need for new chemical entities that possess antimicrobial activity. Further, in order to accelerate the drug discovery process, new methods for synthesizing aminoglycoside antibiotics are needed to provide an array of compounds that are potentially new drugs for the treatment microbial infections.

BRIEF SUMMARY OF THE INVENTION

The present invention provides compounds having the following formula I:

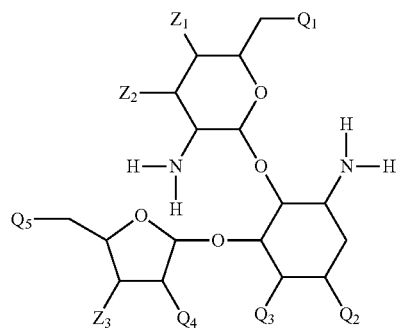

or a stereoisomer, prodrug or pharmaceutically acceptable salt thereof, wherein:

$Q_1$ is azido, —OH, a protected hydroxyl, —$NR_2R_3$ or a nitrogen containing heterocycle radical which can include one or more additional heteroatoms selected from N, O and S wherein the heterocycle is covalently linked through said nitrogen atom;

$Q_2$ is —$NR_2R_4$;

each $Q_3$ and $Q_4$ is —$OR_7$;

$Q_5$ is H, halogen, cyano, azido, —$OR_8$, —$NR_2R_3$, a protected amino group or a nitrogen containing heterocyclic radical which can include one or more additional heteroatoms selected from N, O and S wherein the heterocyclic radical is covalently linked through said nitrogen atom;

each $R_1$ is, independently, H or a hydroxyl protecting group;

each $R_2$ is, independently, H, an amino protecting group, $C_1$-$C_{12}$ alkyl or substituted $C_1$-$C_{12}$ alkyl;

each $R_3$ is, independently, H, an amino protecting group, cyano, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$-$(CH_2)_{nn}$-$E_1$;

$R_4$ is H, an amino protecting group, $C_1$-$C_{12}$ alkyl, substituted $C_1$-$C_{12}$ alkyl or a group having the following formula III:

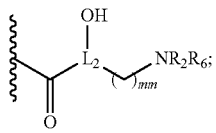

each $R_6$ is, independently, H or an amino protecting group;

each $R_7$ is, independently, H, a hydroxyl protecting group or $-(CH_2)_n-(L_1)_m-(CH_2)_{nn}-E_1$;

$R_8$ is H, a hydroxyl protecting group, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl or $-(CH_2)_n-(L_1)_m-(CH_2)_{nn}-E_1$;

$L_1$ is S, O or $NJ_1$;

$L_2$ is CH or N;

n is an integer from 1 to 8;

m is 0 or 1;

nn is 0 or an integer from 1 to 8;

mm is 1 or 2;

$E_1$ is H, hydroxyl, halogen, cyano, $C_2-C_{12}$ alkenyl, substituted $C_2-C_{12}$ alkenyl, $C_2-C_{12}$ alkynyl, substituted $C_2-C_{12}$ alkynyl, $C_5-C_{20}$ aryl, substituted $C_5-C_{20}$ aryl, heteroaryl, substituted heteroaryl, a heterocyclic radical, a substituted heterocyclic radical or a substituted or unsubstituted mono or poly cyclic structure that can be unsaturated, partially saturated or fully saturated and can include one or more heteroatoms selected from O, N and S;

each $J_1$ and $J_2$ is, independently, H, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl, $C_5-C_{20}$ aryl, substituted $C_5-C_{20}$ aryl, $-C(=O)-X$, a heterocyclic radical or a substituted heterocyclic radical;

each X is, independently, H, $C_1-C_{12}$ alkyl or substituted $C_1-C_{12}$ alkyl;

each $Z_1$ and $Z_2$ is, independently, H, hydroxyl or a protected hydroxyl; and $Z_3$ is $-OR_8$ or a group having the following formula IV:

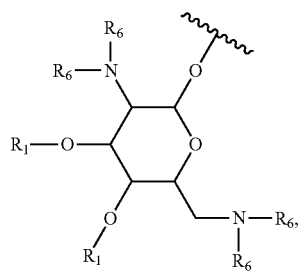

and wherein at least two of $Q_1, Q_2, Q_3, Q_4$ and $Q_5$ are other than hydroxyl, protected hydroxyl, amino or a protected amino group and when $Q_2$ is $-N(H)C(=O)C(H)(OH)CH_2-CH_2NH_2$ then $Q_1$ is other than $-N(H)CH_3$ or $-N(H)CH_2CH_3$ and $Q_5$ is other than $-N(H)C(=NH)NH_2$ or $-N(H)CH=NH_2$.

In one aspect of the present invention, the compounds of formula I are substituted such that:

$Q_1$ is azido or $-NR_{10}R_{11}$; and $Q_2$ is $-NR_{10}R_{12}$, wherein:

$R_{10}$ is H, $C_1-C_{12}$ alkyl or substituted $C_1-C_{12}$ alkyl;

$R_{11}$ is cyano, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl or $-(CH_2)_n-(L_1)_m-(CH_2)_{nn}-E_1$; and $R_{12}$ is $C_1-C_{12}$ alkyl, substituted $C_1-C_{12}$ alkyl or a group having formula III.

In another aspect of the present invention, the compounds of formula I are substituted such that:

$Q_1$ is azido or $-NR_{10}R_{11}$; and $Q_3$ is $-OR_{13}$, wherein:

$R_{10}$ is H, $C_1-C_{12}$ alkyl or substituted $C_1-C_{12}$ alkyl;

$R_{11}$ is cyano, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl or $-(CH_2)_n-(L_1)_m-(CH_2)_{nn}-E_1$; and $R_{13}$ is $-(CH_2)_n-(L_1)_m-(CH_2)_{nn}-E_1$.

In another aspect of the present invention, the compounds of formula I are substituted such that:

$Q_1$ is azido or $-NR_{10}R_{11}$; and $Q_4$ is $-OR_{13}$, wherein:

$R_{10}$ is H, $C_1-C_{12}$ alkyl or substituted $C_1-C_{12}$ alkyl;

$R_{11}$ is cyano, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl or $-(CH_2)_n-(L_1)_m-(CH_2)_{nn}-E_1$; and $R_{13}$ is $-(CH_2)_n-(L_1)_m-(CH_2)_{nn}-E_1$.

In another aspect of the present invention, the compounds of formula I are substituted such that:

$Q_1$ is azido or $-NR_{10}R^{11}$; and $Q_5$ is halogen, cyano, azido, $-OR_{14}$ or $-NR_{10}R_{11}$, wherein:

$R_{10}$ is H, $C_1-C_{12}$ alkyl or substituted $C_1-C_{12}$ alkyl;

$R_{11}$ is cyano, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl or $-(CH_2)_n-(L_1)_m-(CH_2)_{nn}-E_1$; and $R_{14}$ is $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl or $-(CH_2)_n-(L_1)_m-(CH_2)_{nn}-E_1$.

In another aspect of the present invention, the compounds of formula I are substituted such that:

$Q_2$ is $-NR_{10}R_{12}$, and $Q_3$ is $-OR_{13}$, wherein:

$R_{10}$ is H, $C_1-C_{12}$ alkyl or substituted $C_1-C_{12}$ alkyl;

$R_{12}$ is $C_1-C_{12}$ alkyl, substituted $C_1-C_{12}$ alky or a group having formula III; and $R_{13}$ is $-(CH_2)_n-(L_1)_m-(CH_2)_{nn}-E_1$.

In another aspect of the present invention, the compounds of formula I are substituted such that:

$Q_2$ is $-NR_{10}R_{12}$; and $Q_4$ is $-OR_{13}$, wherein:

$R_{10}$ is H, $C_1-C_{12}$ alkyl or substituted $C_1-C_{12}$ alkyl;

$R_{12}$ $C_1-C_{12}$ alkyl, substituted $C_1-C_{12}$ alky or a group having formula III; and $R_{13}$ is $-(CH_2)_n-(L_1)_m-(CH_2)_{nn}-E_1$.

In another aspect of the present invention, the compounds of formula I are substituted such that:

$Q_2$ is $-NR_{10}R_{12}$; and $Q_5$ is halogen, cyano, azido, $-OR_{14}$ or $-NR_{10}R_{11}$;

wherein:

$R_{10}$ is H, $C_1-C_{12}$ alkyl or substituted $C_1-C_{12}$ alkyl;

$R_{11}$ is cyano, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl or $-(CH_2)_n-(L_1)_m-(CH_2)_{nn}E_1$;

$R_{12}$ is $C_1-C_{12}$ alkyl, substituted $C_1-C_{12}$ alky or a group having formula III; and $R_{14}$ is $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$-$(CH_2)_{nn}$-$E_1$.

In another aspect of the present invention, the compounds of formula I are substituted such that $Q_3$ and $Q_4$ are each —$OR_{13}$, wherein each $R_{13}$ is, independently, —$(CH_2)_n$-$(L_1)_m$-$(CH_2)_{nn}$-$E_1$.

In another aspect of the present invention, the compounds of formula I are substituted such that:
$Q_3$ is —$OR_{13}$; and
$Q_5$ is halogen, cyano, azido, —$OR_{14}$ or —$NR_{10}R_{11}$;
wherein:
$R_{13}$ is —$(CH_2)_n$-$(L_1)_m$-$(CH_2)_{nn}$-$E_1$;
$R_{10}$ is H, $C_1$-$C_{12}$ alkyl or substituted $C_1$-$C_{12}$ alkyl;
$R_{11}$ is cyano, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$-$(CH_2)_{nn}$-$E_1$; and
$R_{14}$ is $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$-$(CH_2)_{nn}$-$E_1$.

In another aspect of the present invention, the compounds of formula I are substituted such that:
$Q_4$ is —$OR_{13}$; and
$Q_5$ is halogen, cyano, azido, —$OR_{14}$ or —$NR_{10}R_{11}$;
wherein:
$R_{10}$ is H, $C_1$-$C_{12}$ alkyl or substituted $C_1$-$C_{12}$ alkyl;
$R_{11}$ is cyano, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$-$(CH_2)_{nn}$-$E_1$;
$R_{13}$ is —$(CH_2)_n$-$(L_1)_m$-$(CH_2)_{nn}$-$E_1$; and
$R_{14}$ is $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$-$(CH_2)_{nn}$-$E_1$.

In another aspect of the present invention, the compounds of formula I are substituted such that $Z_1$ and $Z_2$ are both H.

In another aspect of the present invention, the compounds of formula I are substituted such that $Z_1$ and $Z_2$ are both hydroxyl or protected hydroxy.

In another aspect of the present invention, the compounds of formula I are substituted such that one of $Z_1$ and $Z_2$ is H.

In another aspect of the present invention, the compounds of formula I are substituted such that $Q_2$ is an optionally protected group having the formula —N(H)C(O)C(H)(OH)$(CH_2)_2NH_2$.

In another aspect of the present invention, the compounds of formula I are substituted such that $Z_3$ is —$OR_8$.

In another aspect of the present invention, the compounds of formula I are substituted such that $Z_3$ is a group having formula IV.

In another aspect of the present invention, the compounds of formula I are substituted such that:
$Q_2$ is:

and
$Q_4$ is —O—$(CH_2)_n$-$(L_1)_m$-$(CH_2)_{nn}$-$E_1$.

In another aspect of the present invention, the compounds of formula I are substituted such that:
$Q_1$ is —OH, a protected hydroxyl or —$NR_2R_3$;

each $Q_3$ and $Q_5$ is, independently, —OH or a protected hydroxyl; at least one of $Z_1$ and $Z_2$ is H;
$Z_3$ is a group having formula IV; and
each $R_2$ is, independently, H or an amino protecting group.

In another aspect of the present invention, the compounds of formula I are substituted such that:
$Q_1$ is amino or protected amino;
$L_2$ is CH;
$L_1$ is —$NJ_1$; and
$E_1$ is $C_5$-$C_{20}$ aryl, substituted $C_5$-$C_{20}$ aryl, heteroaryl, substituted heteroaryl or a substituted or unsubstituted mono or poly cyclic structure that can be unsaturated, partially saturated or fully saturated and can include one or more heteroatoms selected from O, N and S.

In another aspect of the present invention, the compounds of formula I are substituted such that:
n is an integer from 1 to 3;
m is 1; and
nn is an integer from 1 to 3.

In another aspect of the present invention, the compounds of formula I are substituted such that $E_1$ is $C_5$-$C_{20}$ aryl or substituted $C_5$-$C_{20}$ aryl.

In another aspect of the present invention, the compounds of formula I are substituted such that $E_1$ is phenyl.

In another aspect of the present invention, the compounds of formula I are substituted such that: n is 2; and nn is 2.

In another aspect of the present invention, the compounds of formula I are substituted such that each of $Z_1$ and $Z_2$ is H.

In another aspect of the present invention, the compounds of formula I are substituted such that one of $Z_1$ and $Z_2$ is H and the other of $Z_1$ and $Z_2$ is hydroxy.

In another aspect of the present invention, the compounds of formula I are substituted such that $Q_2$ has the configuration:

and
* indicates a chiral carbon having (S)-configuration.

In another aspect of the present invention, the compounds of formula I are substituted such that:
$Q_2$ is:

$Q_4$ is —O—$(CH_2)_2$—N(H)—$(CH_2)_2$—$C_6H_5$;
$Q_1$ is —OH, a protected hydroxyl, amino or protected amino;
$Q_3$ and $Q_5$ are each —OH;
$Z_3$ is a group having formula IV; and
at least one of $Z_1$ and $Z_2$ is H.

In another aspect of the present invention, the compounds of formula I are substituted such that $Q_2$ and $Q_4$ are each, independently, a group other than hydroxyl, protected hydroxyl, amino or protected amino.

In another aspect of the present invention, the compounds of formula I are substituted such that $Q_1$ is —OH, protected hydroxyl or —$NR_2R_3$.

In another aspect of the present invention, the compounds of formula I are substituted such that $Z_3$ is a group having formula IV.

In another aspect of the present invention, the compounds of formula I are substituted such that:

each of said substituted groups, is, independently, mono or poly substituted with optionally protected substituent groups independently selected from $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl or substituted $C_5$-$C_{20}$ aryl, heterocyclic radical, substituted heterocyclic radical, heteroaryl, substituted heteroaryl, $C_5$-$C_7$ alicyclic radical, substituted $C_5$-$C_7$ alicyclic radical, halogen, —$OJ_3$, —$SJ_3$, —$N_3$, —COOH, —C(=O)—X, —CN, —S(=O)$_2$—X, —S(=O)—X, —C(=O)—$NJ_1J_2$, —N(H)C(=O)-$J_1$, —N($J_1$)—(CH$_2$)$_{nm}$—$OJ_3$ and —N($J_1$)-(CH$_2$)$_{nm}$—$NJ_1J_2$ and a substituted or unsubstituted mono or poly cyclic structure that can be unsaturated, partially saturated or fully saturated and can include one or more heteroatoms selected from O, N and S;

each $J_3$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ aminoalkyl, substituted $C_1$-$C_{12}$ aminoalkyl or a hydroxyl protecting group; and nm is an integer from 1 to 20.

In another aspect of the present invention, the compounds of formula I have the configuration:

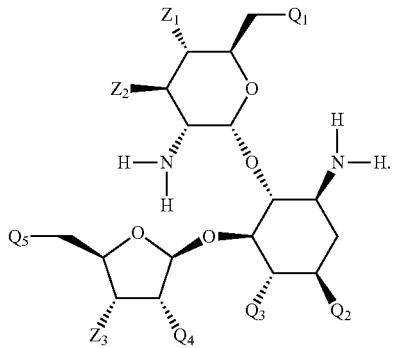

In another aspect of the present invention, the compounds of formula I have the configuration:

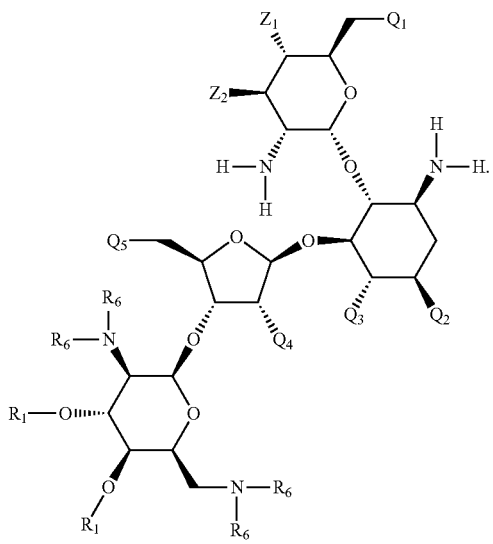

The present invention also provides methods of using a compound of the invention in therapy. In particular, the present invention provides a method of treating a bacterial infection in a mammal comprising administering to the mammal an effective amount of a compound of the invention.

DETAILED DESCRIPTION OF THE INVENTION

As noted above, in one aspect of the present invention, aminoglycoside compounds are provided having the following formula I:

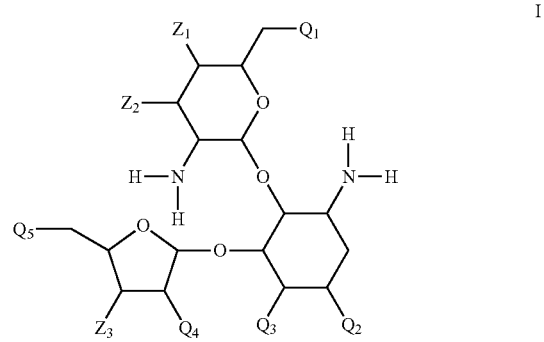

or a stereoisomer, prodrug or pharmaceutically acceptable salt thereof, wherein:

$Q_1$ is azido, —OH, a protected hydroxyl, —NR$_2$R$_3$ or a nitrogen containing heterocycle radical which can include one or more additional heteroatoms selected from N, O and S wherein the heterocycle is covalently linked through said nitrogen atom;

$Q_2$ is —NR$_2$R$_4$;

each $Q_3$ and $Q_4$ is —OR$_7$;

$Q_5$ is H, halogen, cyano, azido, —OR$_8$, —NR$_2$R$_3$, a protected amino group or a nitrogen containing heterocyclic radical which can include one or more additional heteroatoms selected from N, O and S wherein the heterocyclic radical is covalently linked through said nitrogen atom;

each R$_1$ is, independently, H or a hydroxyl protecting group;

each R$_2$ is, independently, H, an amino protecting group, $C_1$-$C_{12}$ alkyl or substituted $C_1$-$C_{12}$ alkyl;

each R$_3$ is, independently, H, an amino protecting group, cyano, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —(CH$_2$)$_n$-(L$_1$)$_m$-(CH$_2$)$_{nn}$-E$_1$;

R$_4$ is H, an amino protecting group, $C_1$-$C_{12}$ alkyl, substituted $C_1$-$C_{12}$ alkyl or a group having the following formula III

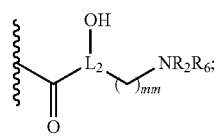

each R$_6$ is, independently, H or an amino protecting group;
each R$_7$ is, independently, H, a hydroxyl protecting group or —(CH$_2$)$_n$-(L$_1$)$_m$-(CH$_2$)$_{nn}$-E$_1$;

R$_8$ is H, a hydroxyl protecting group, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —(CH$_2$)$_n$-(L)$_n$-(CH$_2$)$_{nn}$-E$_1$;

$L_1$ is S, O or $NJ_1$;
$L_2$ is CH or N;
n is an integer from 1 to 8;
m is 0 or 1;
nn is 0 or an integer from 1 to 8;
mm is 1 or 2;
$E_1$ is H, hydroxyl, halogen, cyano, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heteroaryl, substituted heteroaryl, a heterocyclic radical, a substituted heterocyclic radical or a substituted or unsubstituted mono or poly cyclic structure that can be unsaturated, partially saturated or fully saturated and can include one or more heteroatoms selected from O, N and S;
each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, —C(=O)—X, a heterocyclic radical or a substituted heterocyclic radical;
each X is, independently, H, $C_1$-$C_{12}$ alkyl or substituted $C_1$-$C_{12}$ alkyl;
each $Z_1$ and $Z_2$ is, independently, H, hydroxyl or a protected hydroxyl; and
$Z_3$ is —$OR_8$ or a group having the following formula IV:

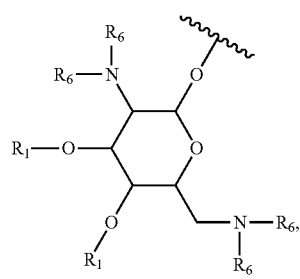

and
wherein at least two of $Q_1$, $Q_2$, $Q_3$, $Q_4$ and $Q_5$ are other than hydroxyl, protected hydroxyl, amino or a protected amino group and when $Q_2$ is —N(H)C(=O)C(H)(OH)CH$_2$—CH$_2$NH$_2$ then $Q_1$ is other than —N(H)CH$_3$ or —N(H)CH$_2$CH$_3$ and $Q_5$ is other than —N(H)C(=NH)NH$_2$ or —N(H)CH=NH$_2$.

In other aspects of the present invention, wherein $Z_3$ is —$OR_8$ or $Z_3$ is a group having the formula IV, aminoglycoside compounds are provided having the following formulas V and VI, respectively:

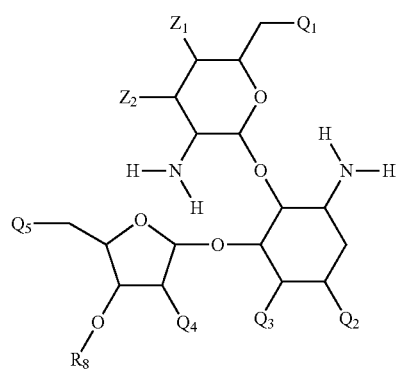

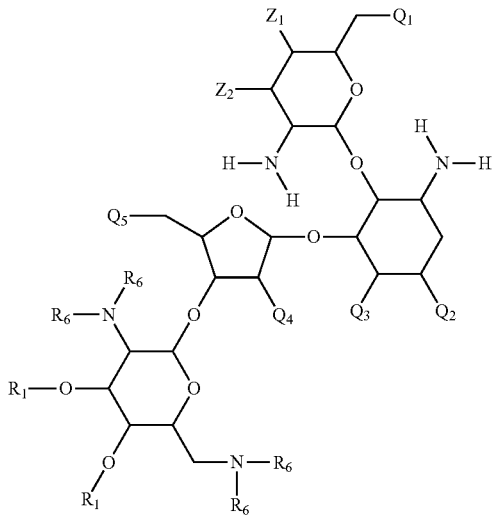

In more specific embodiments of the foregoing, aminoglycoside compounds are provided having the following formulas VII and VIII, respectively:

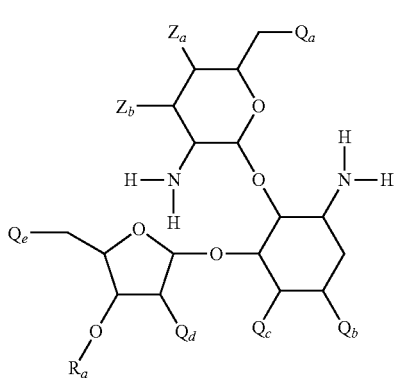

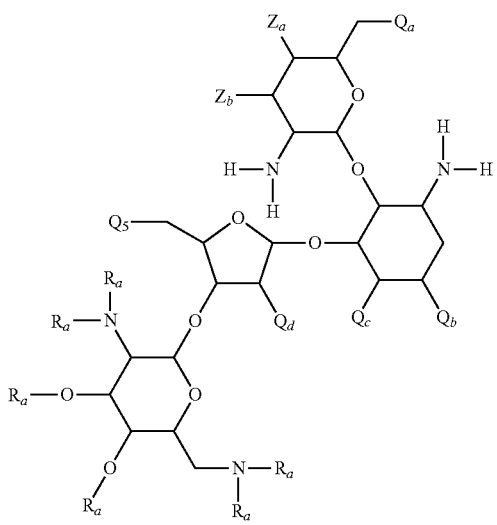

wherein:
each $Z_a$ and $Z_b$ is, independently, H, —OH or a protected hydroxyl;

each $R_a$ is, independently, H, a hydroxyl protecting group or an amino protecting group;

at least two of $Q_a$, $Q_b$, $Q_c$, $Q_d$ and $Q_e$ are, independently, an optionally linked chemical functional group; and each of the remaining $Q_a$, $Q_b$, $Q_c$, $Q_d$ and $Q_e$ are, independently, hydroxyl, amino, a protected hydroxyl, a protected amino or an optionally linked chemical functional group.

Aminoglycoside compounds of the present invention are prepared according to established organic synthetic methods. In a particular general method, paromomycin is selectively protected such that one of the 1, 2", 5", 6 or 6' positions can be selectively functionalized followed by deprotection of one of the remaining protected positions for further functionalization. Following the orthogonal protection schemes provided in the examples below aminoglycoside compounds are prepared having at least two of the 1, 2", 5", 6 or 6' positions selectively functionalized.

In a preferred embodiment the compounds of the present invention are prepared from paromomycin sulfate salt (commercially available from various sources including Sigma-Aldrich Co., et al.). The reactive groups are orthogonally protected as illustrated in the examples below to enable selective functionalization of at least two of the 1, 2", 5", 6 or 6' positions. The methods disclosed herein are amenable to a wide variety of chemical reactions to prepare a large number of paromomycin analogs. The present invention therefor provides a variety of substituted paromomycin analogs that are useful as therapeutic and/or prophylactic agents as well as processes and intermediates for making them.

In some preferred embodiments each of the 3' and 4' substituents (either $Z_1$ and $Z_2$ or $Z_a$ and $Z_b$) are hydroxyl groups as found in paromomycin. In other embodiments one or both of the 3' and 4' substituents are hydrogen.

The term "chemical functional group" as used herein, refers to one or more groups that are directly attached or linked to a site in a compound. Such groups can enhance the properties of the parent compound to provide for example enhanced activity against one or more selected targets. A representative list of chemical functional groups includes, but is not limited to, H, alkyl, substituted alkyl, alkenyl, substituted alkenyl, alkynyl, substituted alkynyl, aminoalkyl, substituted aminoalkyl, carbocyclic alkyl, substituted carbocyclic alkyl, alkenyl carbocyclic, substituted alkenyl carbocyclic, alkynyl carbocyclic, substituted alkynyl carbocyclic, aryl, aralkyl, substituted aralkyl, —O-aralkyl, —S-aralkyl, —NH-aralkyl, heteroaryl, substituted heteroaryl, heteroarylalkyl, substituted heteroarylalkyl, a heterocycle containing one or more heteroatoms selected from N, O and S, a substituted heterocycle, alicyclyl, substituted alicyclyl, a substituted or unsubstituted mono or poly cyclic structure that can be unsaturated, partially saturated or fully saturated and can include one or more heteroatoms selected from O, N and S, wherein said mono or poly cyclic structure is bonded directly or through said substituent group, hydroxyl, alkoxy, thiol, thioalkyl, halogen, an ether having 2 to 10 carbon atoms and 1 to 4 oxygen or sulfur atoms, a metal coordination group, a conjugate group, trifluoromethyl, trifluoromethoxy, —$OJ_a$, —C(=O)$J_c$, =O, —C(=O)$OJ_c$, —$NJ_aJ_b$, =$NJ_a$, —N($J_a$)C(=O)$J_c$, —N($J_a$)C(=O)$NJ_aJ_b$, —N($J_a$)C(S)$NJ_aJ_b$, —N($J_a$)S(O)$_2J_a$, —N($J_a$)C(=$NJ_a$)$NJ_aJ_b$, —N($J_a$)(CH$_2$)$_{nmn}$—$OJ_b$, —N($J_a$)(CH$_2$)$_{nmn}NJ_aJ_b$, —C(=O)$NJ_aJ_b$, —OC(=O)$NJ_aJ_b$, —C(=$NJ_a$)$NJ_aJ_b$, —C(=$NJ_a$)$J_a$, —C(=O)—(CH$_2$)$_2$—CH($NJ_aJ_b$)—C(=O)$OJ_a$, —CN, —NO$_2$, —N$_3$, —NHNH$_2$, —ONH$_2$, —S(O)$_2NJ_aJ_b$, —S(O)$_2J_a$, S, —$SJ_a$, silyl, an amino acid side chain, a carbohydrate, a drug, or a group capable of hydrogen bonding where nmn is from 1 to about 20.

Wherein each $J_a$ and $J_b$ is, independently, H, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocyclic radical, a substituted heterocyclic radical, heteroaryl, substituted heteroaryl, $C_1$-$C_{12}$ aminoalkyl, substituted $C_1$-$C_{12}$ aminoalkyl, —C(O)$J_c$, a protecting group, an optionally linked conjugate group or an optionally linked chemical functional group.

Wherein each $J_c$ is, independently, H, hydroxyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocyclic radical, a substituted heterocyclic radical, heteroaryl, substituted heteroaryl, $C_1$-$C_{12}$ aminoalkyl, substituted $C_1$-$C_{12}$ aminoalkyl, a protecting group, an optionally linked conjugate group or an optionally linked chemical functional group.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such substituent groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxo (—O—$R_{aa}$), aryl, aralkyl, heterocyclic, heteroaryl, heteroarylalkyl, amino (—$NR_{bb}R_{cc}$), imino (=$NR_{bb}$), amido (—C(O)$NR_{bb}R_{cc}$ or —N($R_{bb}$)C(O)$R_{aa}$), azido (—N$_3$), nitro (—NO$_2$), cyano (—CN), carbamido (—OC(O)$NR_{bb}R_{cc}$ or —N($R_{bb}$)C(O)$OR_{aa}$), ureido (—N($R_{bb}$)C(O)$NR_{bb}R_{cc}$), thioureido (—N($R_{bb}$)C(S)$NR_{bb}R_{cc}$), guanidinyl (—N($R_{bb}$)C(—$NR_{bb}$)$NR_{bb}R_{cc}$), amidinyl (—C(=$NR_{bb}$)$NR_{bb}R_{cc}$ or —N($R_{bb}$)C($NR_{bb}$)$R_{aa}$), thiol (—$SR_{bb}$), sulfinyl (—S(O)$R_{bb}$), sulfonyl (—S(O)$_2R_{bb}$), sulfonamidyl (—S(O)$_2NR_{bb}R_{cc}$ or —N($R_{bb}$)S(O)$_2R_{bb}$) and conjugate groups. Wherein each $R_{aa}$, $R_{bb}$ and $R_{cc}$ is H, an optionally linked chemical functional group or a further substituent group, with a preferred list including, without limitation, H, alkyl, alkenyl, alkynyl, aliphatic, alkoxy, acyl, aryl, aralkyl, heteroaryl, alicyclic, heterocyclic and heteroarylalkyl groups.

Linking groups such as those known in the art are amenable to the present invention. Linking groups or bifunctional linking moieties are useful for attachment of chemical functional groups, conjugate groups, reporter groups and other groups to selective sites in a parent compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the linker comprises a chain structure or an oligomer of repeating units such as ethylene glyol or amino acid units. Examples of functional groups that are routinely used in a bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms ($C_1$-$C_{24}$ alkyl), more typically from 1 to about 12 carbon atoms ($C_1$-$C_{12}$ alkyl) with from 1 to about 6 carbon atoms ($C_1$-$C_6$ alkyl) being more preferred. The teen "lower alkyl" as used herein includes from 1 to about 6 carbon atoms. Alkyl groups as used herein may optionally include one or more further substitutent groups.

The term "alkenyl," as used herein, refers to a straight or branched hydrocarbon chain radical containing from two up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms ($C_2$-$C_{24}$ alkenyl), more typically from 2 to about 12 carbon atoms ($C_2$-$C_{12}$ alkenyl) with from 2 to about 6 carbon atoms ($C_2$-$C_6$ alkenyl) being more preferred. Alkenyl groups as used herein may optionally include one or more further substitutent groups.

The term "alkynyl," as used herein, refers to a straight or branched hydrocarbon radical containing from two up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms ($C_2$-$C_{24}$ alkynyl), more typically from 2 to about 12 carbon atoms ($C_2$-$C_{17}$ alkynyl) with from 2 to about 6 carbon atoms ($C_2$-$C_6$ alkynyl) being more preferred. Alkynyl groups as used herein may optionally include one or more further substitutent groups.

The term "aminoalkyl" as used herein, refers to an amino substituted alkyl, alkenyl or alkynyl radical. This term is meant to include $C_1$-$C_{12}$ alkyl groups having an amino substituent at any position and wherein the alkyl group attaches the aminoalkyl group to the parent molecule. The alkyl, alkenyl, alkynyl or amino portions of the aminoalkyl group can be further substituted with substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interupted with one or more heteroatoms that include nitrogen, oxygen, sulfur and phosphorus. Such aliphatic groups interupted by heteroatoms include without limitation polyalkoxys, such as polyalkylene glycols, polyamines, and polyimines. Aliphatic groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "alkoxy," as used herein, refers to a radical formed between an alkyl, alkenyl or alkynyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The terms "halo" and "halogen," as used herein, refer to an atom selected from fluorine, chlorine, bromine and iodine.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "aralkyl" and "arylalkyl," as used herein, refer to a radical formed between an alkyl, alkenyl or alkynyl group and an aryl group wherein the alkyl, alkenyl or alkynyl group is used to attach the aralkyl group to a parent molecule. Examples include, but are not limited to, benzyl, phenethyl and the like. Aralkyl groups as used herein may optionally include further substitutent groups attached to the alkyl, alkenyl, alkynyl, aryl or both groups that form the radical group.

The term "heterocyclic," "heterocyclic radical," or "heterocycle" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined having an alkyl, alkenyl or alkynyl radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups.

The term "mono or poly cyclic structure" as used in the present invention includes all ring systems that are single or polycyclic having rings that are fused or linked and is meant to be inclusive of single and mixed ring systems individually selected from aliphatic, alicyclic, aromatic, aralkyl, heterocyclic, heteroaromatic, and heteroarylalkyl groups. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "acyl," as used herein, refers to a radical formed by removal of a hydroxyl group from an organic acid and has the general formula —C(O)—X, where X is typically aliphatic, alicyclic or aromatic. Acyl groups as used herein may optionally include further substituent groups.

In one aspect of the present invention aminoglycoside compounds having formula I, V and VI are are modified by covalent attachment of one or more conjugate groups that modify one or more properties of the compounds, including but not limited to pharmakodynamic, pharmacokinetic, binding, absorption, cellular distribution, cellular uptake, charge and clearance. Conjugate groups are routinely used in the chemical arts with a preferred list including, without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Reporter groups that are suitable as conjugate groups include any moiety that can be detected by, for example, spectroscopic means. Examples of reporter groups include dyes, fluorophores, phosphors, radiolabels, and the like. In some embodiments, the reporter group is biotin, flourescein, rhodamine, coumarin, or related compounds. Reporter groups can also be attached to other conjugate moieties. Conjugate moieties can be attached directly to a compound of the present invention or through a linker group or bifunctional linking moiety (linker or tether).

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into aminoglycosides of the invention as precursors. For example an amino group can be placed into a compound of the invention as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Examples of amino protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

Examples of thiol protecting groups include, but are not limited to, triphenylmethyl (trityl), benzyl (Bn), and the like.

The synthesized compounds can be separated from reaction mixtures and further purified by methods including but not limited to column chromatography, high pressure liquid chromatography and recrystallization. Further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids et al. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Susceptible organisms generally include those gram positive and gram negative, aerobic and anaerobic organisms whose growth can be inhibited by the compounds of the invention such as *Staphylococcus, Lactobacillus, Streptococcus, Sarcina, Escherichia, Enterobacter, Klebsiella, Pseudomonas, Acinetobacter, Proteus, Campylobacter, Citrobacter, Nisseria, Baccillus, Bacteroides, Peptococcus, Clostridium, Salmonella, Shigella, Serratia, Haemophilus, Brucella* and other organisms.

It has been found that the compounds of the present invention possess antibacterial activity against a wide spectrum of gram positive and gram negative bacteria, as well as enterobacteria and anaerobes. The compounds, by reason of their in vitro activity, may be used in scrub solutions for surface inhibition of bacterial growth, e.g., in sterilization of glasswear or as an additive in fabric laundering compositions.

Accordingly there is provided a method of treating bacterial infection in a mammal comprising administering to the mammal, for example a human, an effective amount of a compound of the invention. By "effective amount" is meant an amount of compound which upon administration is capable of reducing or preventing proliferation of the bacteria or reducing or preventing symptoms associated with the bacterial infection. The actual amount of compound administered and the route of administration will depend upon the particular disease or bacteria as well as other factors such as the size, age, sex and ethnic origin of the individual being treated and is determined by routine analysis. The compounds of the invention may also be formulated into compositions together with pharmaceutically acceptable carriers for parenteral injection, for oral administration in solid or liquid form, for rectal administration, and the like. In methods of the invention, the compound may be administered orally (including buccal, sublingual, inhalation), nasally, rectally, vaginally, intravenously, intradermally, subcutaneously and topically. Compounds will be formulated into compositions suitable for administration for example with suitable carriers, diluents, thickeners, adjuvants, etc., as are routine in the formulation art. Compositions of the invention may also include additional active ingredients. Dosage forms include solutions, powders, tables, capsules, gel capsules, suppositories, topical ointments and creams and aerosols for inhalation.

Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carries include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. Optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances of binders may be desirably added to such formulations. The use of such formulations has the effect of delivering the nucleic acid to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally, Nairn, Chapter 83; Block, Chapter 87; Rudnic et. al., Chapter 89; and Longer et. al., Chapter 91 In: Remington's Pharmaceutical Sciences, 18$^{th}$ Ed., Gennaro, ed., Mack Publishing Co., Easton, Pa., 1990. The formulations of the invention can be converted in a known manner into the customary fog mulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 95% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); filters (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods will known in the art. The preparations may be also contain flavoring, coloring and/or sweetening agents as appropriate.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided soled carriers or both, and then, if necessary, shaping the product.

Formulations of the present invention suitable for oral administration may be presented as discrete units such as capsules, cachets or tables each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

Included within the scope of the present invention are the pharmaceutically acceptable salts of the foregoing compounds. As used herein, the term "pharmaceutically acceptable salts" refers to non-toxic acid addition salts and alkaline earth metal salts of the compounds of the invention. The salts can be prepared in situ during the final isolation and purification of the compounds of the invention, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts.

Included within the scope of the present invention are prodrugs of the foregoing compounds. As used herein, the term "prodrug" refers to a compound that may be converted under physiological conditions or by solvolysis to a biologically active compound of the present invention. Thus, the term "prodrug" refers to a metabolic precursor of a compound of the present invention that is pharmaceutically acceptable. A prodrug may be inactive when administered to a subject in need thereof, but is converted in vivo to an active compound. Prodrugs are typically rapidly transformed in vivo to yield the active compound, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam)). A discussion of prodrugs is also provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release an active compound of the present invention in vivo when such prodrug is administered to a mammalian subject. Prodrugs are generally prepared by modifying functional groups in a way such that the modification is cleaved, either by routine manipulation or in vivo, yielding the parent compound. Prodrugs include, for example, compounds of the present invention wherein hydroxy, amine or sulfhydryl groups are bonded to any group that, when administered to a mammalian subject, cleaves to form the hydroxy, amine or sulfhydryl groups. Thus, representative examples of prodrugs include (but are not limited to) acetate, formate and benzoate derivatives of alcohol and amine functional groups of the compounds of the present invention. Further, in the case of a carboxylic acid (—COOH), esters may be employed, such as methyl esters, ethyl esters, and the like.

The invention disclosed herein is also meant to encompass the in vivo metabolic products of the disclosed compounds. Such products may result from, for example, the oxidation, reducation, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its coversion products from the urine, blood or other biological samples.

EXAMPLES

Example 1

4',6'-O-benzylidene-penta-N-benzyloxycarbonyl paromomycin (2)

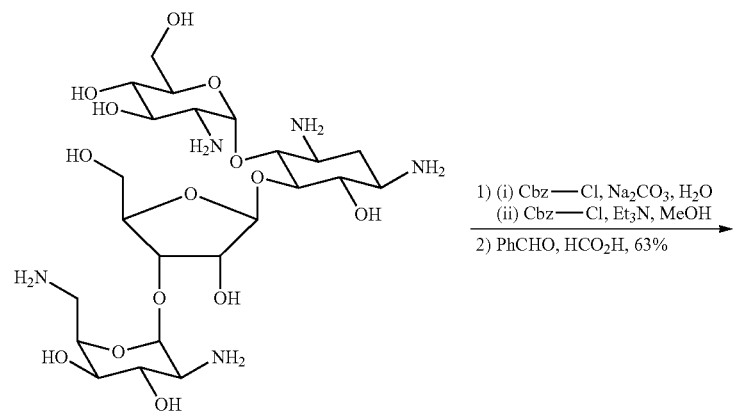

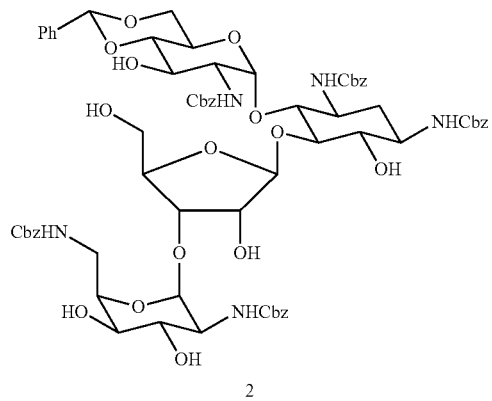

2

Sodium carbonate (55.0 g, 0.523 mol) and Cbz-Cl (20.00 mL, 0.139 mol) were added to paromomycin sulfate (30.00 g, 0.0271 mol) in water (500 mL). After 35 hours under vigorous stirring, the water was decanted and the white precipitate was washed with water twice. A solution of triethylamine (97.00 mL, 0.697 mol) in methanol (600 mL) was added, followed by Cbz-Cl (25.00 mL, 0.174 mol). After 24 hours, dimethylamine (100 mL of a 40% aqueous solution) was added to quench the remaining Cbz-Cl. The solvents were evaporated and the oil was washed with 3% methanol in ether twice and water. The resulting sticky solid was co distilled with pyridine (200 mL) three times and at ½ of the volume of the third co distillation, toluene (200 mL) was added and the solvents were evaporated to dryness. Another co-distillation with toluene (300 mL) was done before heating the flask at 60° C. under 10 mm Hg vacuum for 12 hours. Freshly distilled benzaldehyde (400 mL) was added to the resulting white solid and sonication was used to form a solution. To the stirred mixture was added 4 angstrom molecular sieves (15g) and formic acid (20.00 mL, 0.530 mol). After stirring for 12 hours at room temperature, the mixture was added dropwise to a stirred ice-cold solution of saturated aqueous $Na_2CO_3$, extracted with ethyl acetate (3 times), and the organic layer was washed with water, brine and dried over $Na_2SO_4$. The solvent was evaporated to dryness and excess benzaldehyde was removed under vacuum to afford a crude solid, which was purified by flash column chromatography over silica gel (3% MeOH/$CH_2Cl_2$) to obtain pure Compound 2 (23.89 g, 63%).

The spectroscopic analysis of the resulting material was consistent with data reported in the literature for the identical material (Hanessian S., Takamoto T., Massé R., Patil G.; Aminoglycoside antibiotics: Chemical conversion of neomycin B, paromomycin, and lividomycin B into bioactive pseudosaccharides; *Can. J. Chem.*, 1978, 56, 1482).

Example 2

4',6'-O-benzylidene-penta-N-benzyloxycarbonyl-5''-O-tert-butyldimethylsilyl paromomycin (3)

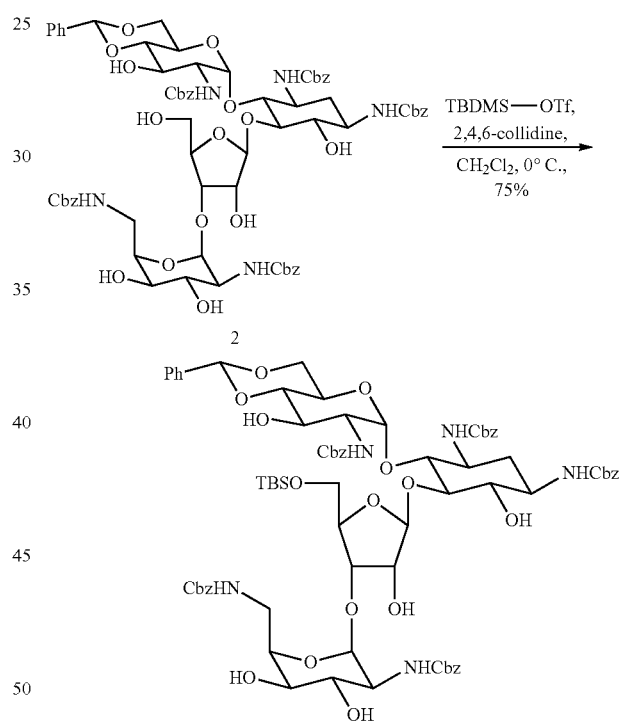

The alcohol, Compound 2 (6.00 g, 4.367 mmol) dried by two co distillations with toluene was dissolved in $CH_2Cl_2$ (400 mL) and 2,4,6-collidine (1.15 mL, 8.735 mmol) followed by TBDMSOTf (0.50 mL, 2.184 mmol) were added at 0° C. After 18 hours, 0.6 equivalent of TBDMSOTf was added and 6 hours later, some of the $CH_2Cl_2$ was evaporated to a smaller volume for washing with HCl (0.5 M) twice and $H_2O$. Drying with $Na_2SO_4$ and purification by silica gel chromatography (2% MeOH/$CH_2Cl_2$) gave Compound 3 (4.861 g, 75%).

$[\alpha]_D$+41.8° (c 0.9, $CHCl_3$); $R_f$ 0.6 ($CHCl_3$:EtOAc:MeOH (20:5:3); $^1$H NMR (300 MHz, $CDCl_3$) δ7.60-7.10 (m, 30H)

5.60-3.00 (m, 41H), 2.20 (m, 1H), 1.30 (m, 1H), 0.83 (s, 9H), 0.01 (s, 6H); ESI m/z calcd $C_{76}H_{93}N_5O_{24}Si$ 1487.60 found 1488.9.

Example 3

2"-O-allyl-4',6'-O-benzylidene-penta-N-benzyloxycarbonyl-5"-O-tert-butyldimethylsilyl paromomycin (4)

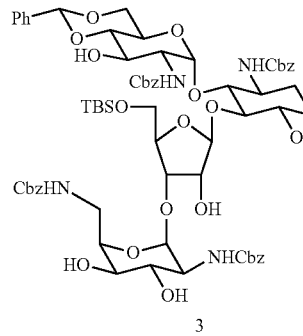

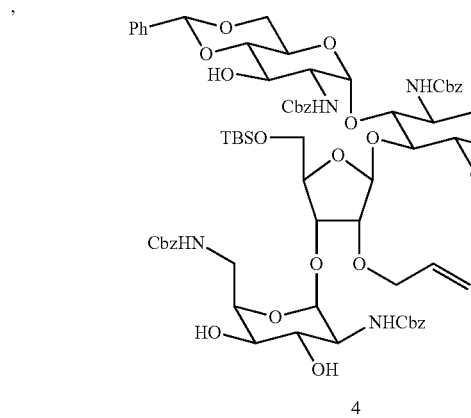

Compound 3 (2.10 g, 1.411 mmol) was co-distilled with toluene twice and the residue dissolved in dry THF (70 mL) in a flask covered with aluminum foil. Allyl iodide (1.29 mL, 14.11 mmol) was added followed by the dropwise addition of 0.5 M KHMDS solution in toluene (1.411 mL, 0.706 mmol). The mixture was stirred for overnight at room temperature, then, 0.3 equivalents of KHMDS was added and 6 hours later the reaction mixture was quenched with an aqueous solution of NH$_4$Cl saturated (2 mL) and water. THF was evaporated and the aqueous layer was extracted with ethyl acetate (3 times), and the organic layer was washed with a sodium thiosulfate solution, brine and dried over Na$_2$SO$_4$. The solvent was evaporated to dryness to afford a crude solid, which was purified by silica gel flash chromatography (1.5% MeOH/CH$_2$Cl$_2$) providing the corresponding allyl ether, Compound 4 (1.468 g, 68%).

$[\alpha]_D$+22.2° (c 2.6, CHCl$_3$); R$_f$ 0.7 (CHCl$_3$:EtOAc:MeOH (20:5:3); $^1$H NMR (300 MHz, CDCl$_3$) δ7.60-7.10 (m, 30H), 6.30-3.00 (m, 44H), 2.20 (m, 1H), 1.30 (m, 1H), 0.83 (s, 9H), 0.01 (s, 6H); $^{13}$C NMR (75 MHz, CDCl$_3$) δ 157.7, 157.1, 156.5, 155.6, 137.2, 136.2, 135.7, 128.8, 128.5, 128.4, 128.0, 127.9, 127.4, 126.3, 126.0, 101.5, 99.4, 85.2, 82.3, 81.4, 77.2, 76.9, 76.6, 76.2, 74.2, 72.7, 69.5, 68.5, 67.3, 66.7, 63.5, 62.8, 56.5, 52.7, 50.8, 40.1, 33.7, 25.8, 18.1, 14.1, −5.3, −5.5, −5.8; ESI m/z calcd for $C_{79}H_{97}N_5O_{24}Si$ 1527.63. found 1528.8.

Example 4

2"-O-allyl-3',3',4'-tri-O-benzoyl-4',6'-O-benzylidene-penta-N-benzyloxycarbonyl-5"-O-tert-butyldimethylsilyl paromomycin (5)

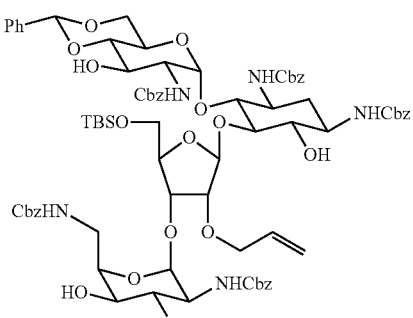

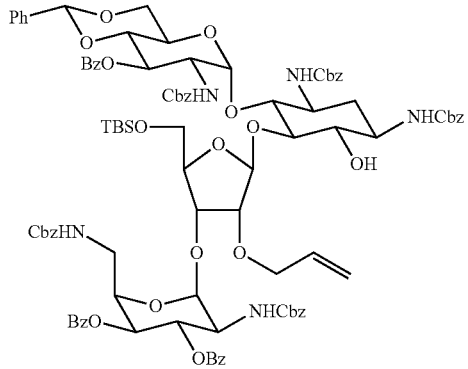

A solution containing Compound 4 (5.30 g, 3.46 mmol) and N,N-dimethyl-4-aminopyridine (100 mg) in dry pyridine (100 mL) was treated with benzoyl chloride (3.017 mL, 34.641 mmol). The reaction mixture was stirred at room temperature for 36 hours water (5 mL) was added and after standing for 10 min, the solvent was removed under vacuum. The residue was dissolved in ethyl acetate, and the organic layer was washed with NaHCO$_3$ saturated, 0.5 M HCl and water, dried over Na$_2$SO$_4$ and concentrated under vacuum. The crude product was purified by silica gel flash column chromatography (1:1 EtOAc/hexane) to yield Compound 5 (5.3 g, quantitative).

$[\alpha]_C$+11.6° (c 2.5, CHCl$_3$); R$_f$ 0.6 (1:1 EtOAc/hexane); $^1$H NMR (300 MHz, CDCl$_3$) δ 8.10-7.10 (m, 47H), 6.30-3.00 (m, 44H), 2.20 (m, 1H), 1.30 (m, 1H), 0.83 (s, 9H), 0.01 (s, 6H); $^{13}$C NMR (75 MHz, CDCl$_3$) δ158.5, 156.4, 138.0, 137.0, 136.9, 136.8, 136.5, 129.6, 129.5, 129.4, 129.2, 129.1, 129.0, 128.8, 128.7, 128.4, 128.3, 128.2, 128.1, 127.0, 98.5, 82.2, 78.1, 70.3, 70.2, 68.0, 67.8, 67.6, 67.4, 67.2, 26.6, 18.9; ESI m/z calcd for $C_{100}H_{109}N_5O_{27}Si$ 1839.71 found 1840.9.

Example 5

3',3''',4'''-tri-O-benzoyl-4',6'-O-benzylidene-penta-N-benzyloxycarbonyl-2''-O-methylenecarbonyl-5''-O-tert-butyldimethylsilyl paromomycin (6)

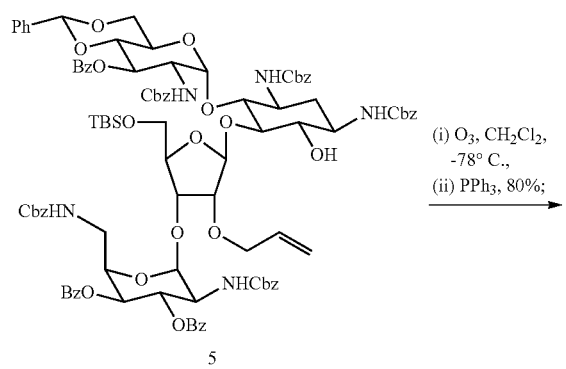

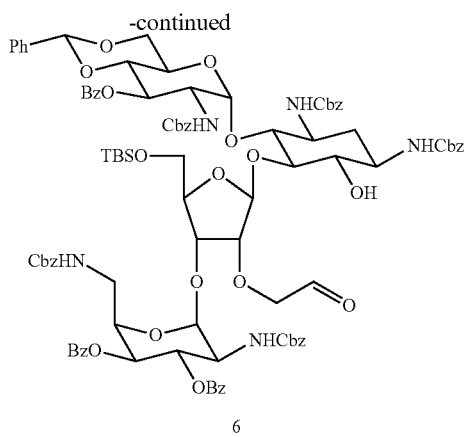

The allyl ether derivative, Compound 5 (2.00 g, 1.086 mmol) in $CH_2Cl_2$ (60 mL) was cooled at $-78°$ C. and ozone was bubbled for 2 hours after which excess ozone was removed by bubbling argon. The mixture was treated with PPh$_3$ (427 mg, 1.629 mmol), warmed to room temperature and the solvent was removed under vacuum. The crude solid was purified by silica gel flash chromatography (2:3 EtOAc/hexane) to give the aldehyde, Compound 6 (1.627 g, 80%).

$R_f$ 0.4 (1:1 EtOAc/hexane); ESI m/z $C_{99}H_{107}N_5O_{28}Si$ 1841.69. found 1842.9.

Example 6

General Procedure for Reductive Amination

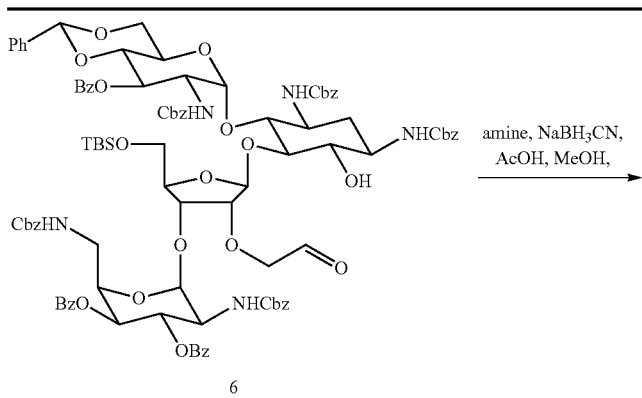

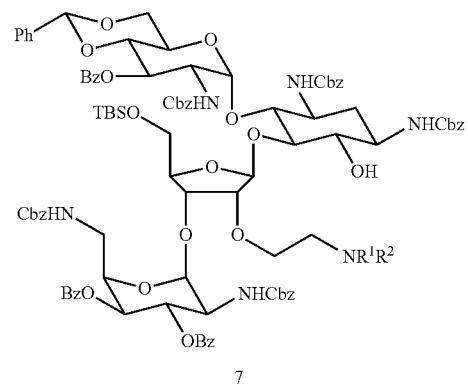

-continued
| Compound | R¹ | R² |
|---|---|---|
| 7a | H | 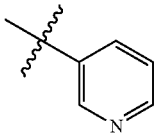 [SMILES: *c1cccnc1] |
| 7b | H | 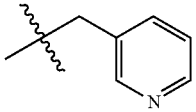 |
| 7c | H | 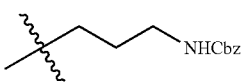 |
| 7d | H | 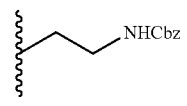 |
| 7e | H | 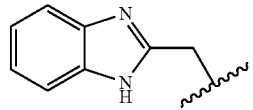 [SMILES: *Cc1nc2ccccc2[nH]1] |
| 7f | H | 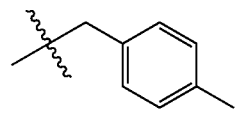 [SMILES: *Cc1ccc(C)cc1] |
| 7g | Me | Me |
| 7h | 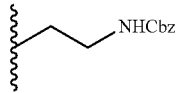 [SMILES: *CCNC(=O)OCc1ccccc1] | 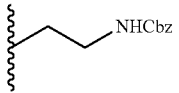 |
| 7i | 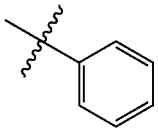 [SMILES: *c1ccccc1] | |
| 7l | H | 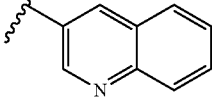 |
| 7m | H | 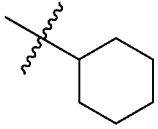 [SMILES: *C1CCCCC1] |
| 7n | H |  |

-continued
| | | |
|---|---|---|
| 7o | H | 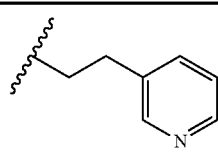 |
| 7p | H | 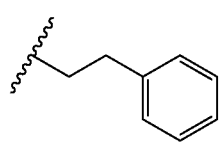 [SMILES: *CCc1ccccc1] |
| 7q | H | 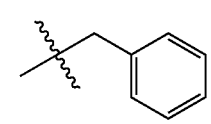 [SMILES: *Cc1ccccc1] |
| 7r | H | 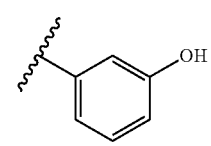 [SMILES: *c1cccc(O)c1] |
| 7s | H | 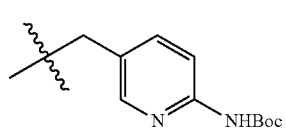 [SMILES: *Cc1ccc(NC(=O)OC(C)(C)C)nc1] |
| 7t | H | 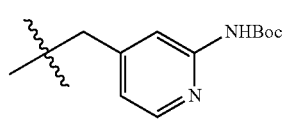 [SMILES: *Cc1ccnc(NC(=O)OC(C)(C)C)c1] |
| 7u | H | 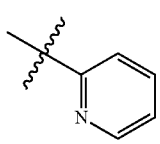 |
| 7v | H | 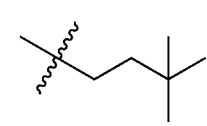 [SMILES: *CCC(C)(C)C] |
| 7w | H | 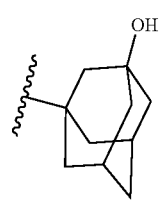 [SMILES: *C12CC3CC(C1)CC(O)(C3)C2] |
| 7x | H | 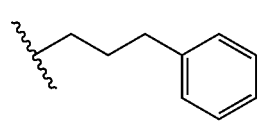 [SMILES: *CCCc1ccccc1] |
| 7y | H | 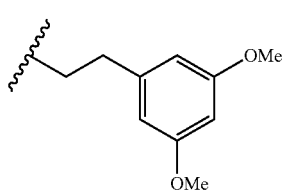 [SMILES: *CCc1cc(OC)cc(OC)c1] |

-continued
| | | |
|---|---|---|
| 7z | H | 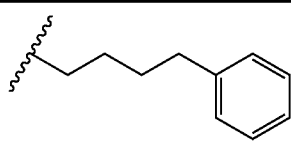 |
| 7aa | H | 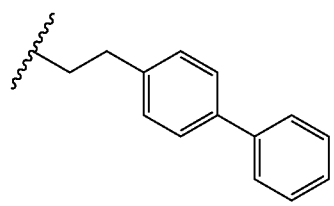 [SMILES: *CCc1ccc(-c2ccccc2)cc1] |
| 7ab | H | 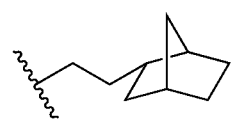 [SMILES: *CCC1CC2CCC1C2] |
| 7ac | H | 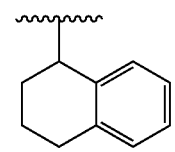 [SMILES: *C1CCCc2ccccc21] |
| 7ad | H | 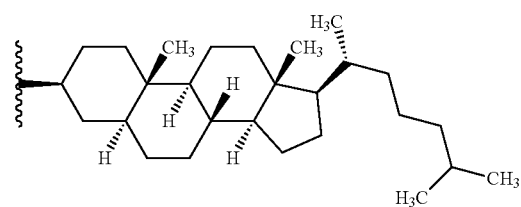 |
| 7ae | H | 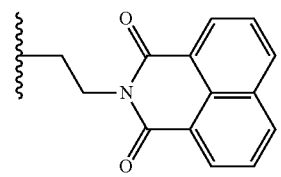 |
| 7af | H | 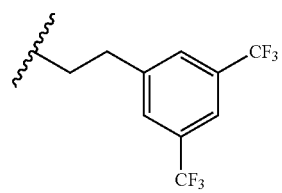 |
| 7ag | 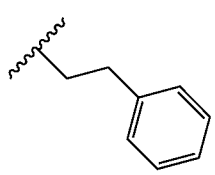 [SMILES: *CCc1ccccc1] | 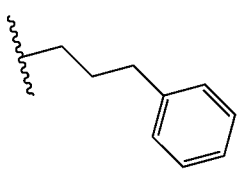 [SMILES: *CCCc1ccccc1] |
| 7ah | H | 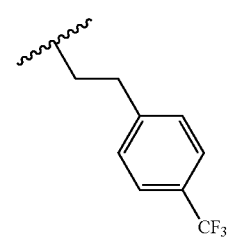 [SMILES: *CCc1ccc(C(F)(F)F)cc1] |

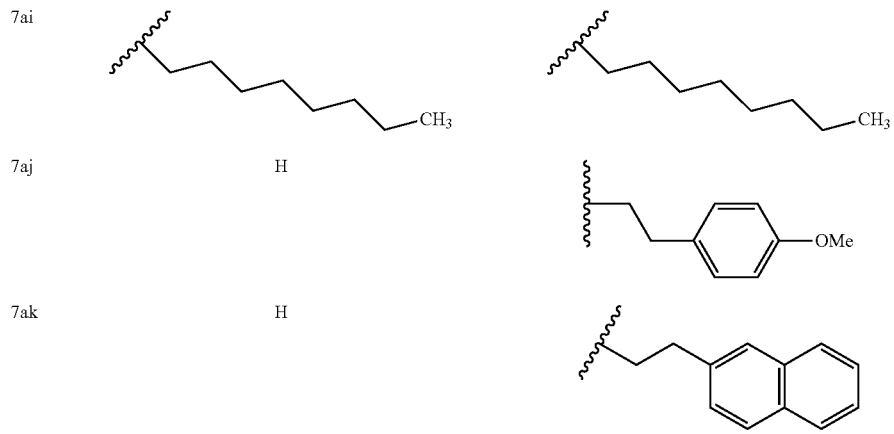

To a mixture of Compound 6 (80.0 mg, 0.043 mmol) and the appropriate amine (0.129 mmol) in dry MeOH (3 mL) was added acetic acid (0.1 mL) followed by $NaBH_3CN$ (1.0 M in THF, 60 µL). The mixture was stirred at room temperature overnight. The solvents were removed under vacuum and the crude solid was dissolved in ethyl acetate and washed with a solution of $NaHCO_3$ saturated and dried over $Na_2SO_4$. After evaporation of the solvents, the residue was purified by flash chromatography.

Compound 7a. 90% yield from 2-aminopyridine and compound 6 using the general procedure above; silica gel flash chromatography eluent: EtOAc:hexane (4:1); $[\alpha]_D$+15.7° (c 1.3, $CHCl_3$); $R_f$ 0.5 (EtOAc); ESI m/z $C_{104}H_{113}N_7O_{27}Si$ 1919.75. found 1920.8;

Compound 7b. 90% yield from 2-(aminomethyl)pyridine and compound 6 using the general procedure above; silica gel flash chromatography eluent: 3% MeOH/$CH_2Cl_2$; $[\alpha]_D$+17.8° (c 0.9, $CHCl_3$); $R_f$ 0.6 (5% MeOH/$CH_2Cl_2$); ESI m/z $C_{105}H_{115}N_7O_{27}Si$ 1933.76. found 1934.8;

Compound 7c. 90% yield from N-1-(benzyloxycarbonyl)-1,3-diaminopropane and compound 6 using the general procedure above; silica gel flash chromatography eluent: 3% MeOH/$CH_2Cl_2$; +12.7° (c 0.8, $CHCl_3$); $R_f$ 0.5 (5% MeOH/$CH_2Cl_2$); FAB m/z $C_{110}H_{123}N_7O_{29}Si$ 2033.81. found 2036.1.

Compound 7d. 90% yield from N-1-(benzyloxycarbonyl)-1,2-diaminoethane and compound 6 using the general procedure above; silica gel flash chromatography eluent: 3% MeOH/$CH_2Cl_2$; $[\alpha]_D$+21.6.7° (c 1.7, $CHCl_3$); $R_f$ 0.5 (5% MeOH/$CH_2Cl_2$); ESI m/z $C_{109}H_{121}N_7O_{29}Si$ 2019.80. found 2021.9;

Compound 7e. 90% yield from 2-aminomethylbenzimidazole and compound 6 using the general procedure above (note: the benzylidene and the TBS were often removed during the reductive amination); silica gel flash chromatography eluent: 7% MeOH/$CH_2Cl_2$; $[\alpha]_D$+11.5° (c 1.1, $CHCl_3$); $R_f$0.5 (10% MeOH/$CH_2Cl_2$); ESI m/z $C_{94}H_{98}N_8O_{27}$ 1770.65. found 1771.7;

Compound 7f. 90% yield from p-methylbenzylamine and compound 6 using the general procedure above; silica gel flash chromatography eluent: 3% MeOH/$CH_2Cl_2$; $[\alpha]_D$+8.9° (c 1.7, $CHCl_3$); $R_f$ 0.6 (5% MeOH/$CH_2Cl_2$); ESI m/z $C_{107}H_{118}N_6O_{27}Si$ 1946.78. found 1947.5.

Compound 7g. 90% yield from dimethylamine and compound 6 using the general procedure above; silica gel flash chromatography eluent: 3% MeOH/$CH_2Cl_2$; $[\alpha]_D$+28.3° (c 0.8, $CHCl_3$); $R_f$ 0.6 (10% MeOH/$CH_2Cl_2$); ESI m/z $C_{101}H_{114}N_6O_{27}Si$ 1870.75. found 1871.8;

Compound 7h. 90% yield from bis-[N-1-(benzyloxycarbonyl)aminoethyl]amine and compound 6 using the general procedure above; silica gel flash chromatography eluent: 3% MeOH/$CH_2Cl_2$; $[\alpha]_D$+10.8° (c 1.5, $CHCl_3$); $R_f$ 0.7 (5% MeOH/$CH_2Cl_2$); ESI m/z $C_{102}H_{116}N_8O_{33}$ 1980.76. found 1981.7;

Compound 7i. 90% yield from N-1-(benzyloxycarbonyl) piperazine and compound 6 using the general procedure above; silica gel flash chromatography eluent: 3% MeOH/$CH_2Cl_2$; $[\alpha]_D$+13.1° (c 1.2, $CHCl_3$); $R_f$ 0.5 (5% MeOH/$CH_2Cl_2$); FAB m/z $C_{118}H_{128}N_7O_{30}Si$ 2150.85. found 2149.6.

Compound 7l. 88% yield from aniline and compound 6 using the general procedure above; ESI m/z $C_{105}H_{114}N_6O_{27}Si$ 1920.14. found 1921.0; No $^1H$ NMR available.

Compound 7m. 84% yield from 3-aminoquinoline and compound 6 using the general procedure above; ESI m/z $C_{108}H_{115}N_7O_{27}Si$ 1971.18. found 1972.0

Compound 7n. 88% yield from cyclohexylamine and compound 6 using the general procedure above; ESI m/z $C_{105}H_{120}N_6O_{27}Si$ 1926.19. found 1927.0

Compound 7o. 92% yield from 3-(2-aminoethyl)pyridine and compound 6 using the general procedure above; ESI m/z $C_{106}H_{117}N_7O_{27}Si$ 1949.18. found 1950.3

Compound 7p. 74% yield from n-phenethylamine and compound 6 using the general procedure above; ESI m/z $C_{107}H_{118}N_6O_{27}Si$ 1948.19. found 1949.1

Compound 7q was prepared from benzylamine and compounds 6 and was subsequently taken on directly to the next step without further characterization.

Compound 7r was prepared from 3-aminophenol and compounds 6 and was subsequently taken on directly to the next step without further characterization.

Compound 7s was prepared from N-2-(t-butoxycarbonylamino)-5-(aminomethyl)pyridine and compounds 6 and was subsequently taken on directly to the next step without further characterization.

Compound 7t was prepared from N-2-(t-butoxycarbonylamino)-4-(aminomethyl)pyridine and compounds 6 and was subsequently taken on directly to the next step without further characterization.

Compound 7u. 90% yield from 2-aminopyridine and compound 6 using the general procedure above; ESI m/z $C_{104}H_{113}N_7O_{27}Si$ 1921.13. found 1921.0

Compound 7v was prepared from 3,3-dimethylaminopropane and compounds 6 and was subsequently taken on directly to the next step without further characterization.

Compound 7w was prepared from 1-amino-3-hydroxyadamantane and compounds 6 and was subsequently taken on directly to the next step without further characterization.

Compound 7x. 85% yield from n-phenpropylamine and compound 6 using the general procedure above; ESI m/z $C_{108}H_{120}N_6O_{27}Si$ 1962.22. found 1963.3

Compound 7y was prepared from 1-amino-2-(2,4-dimethoxyphen-1-yl)ethane and compounds 6 and was subsequently taken on directly to the next step without further characterization.

Compound 7z was prepared from n-phenbutylamine and compound 6 and was subsequently taken on directly to the next step without further characterization.

Compound 7aa was prepared from (4-phenyl)phenethylamine and compound 6 and was subsequently taken on directly to the next step without further characterization.

Compound 7ab was prepared from 1-amino-2-(norborn-2-yl)ethane and compound 6 and was subsequently taken on directly to the next step without further characterization.

Compound 7ac was prepared from 2-aminonapthylene and compound 6 and was subsequently taken on directly to the next step without further characterization.

Compound 7ad was prepared from the amino-substituted cholesterol and compound 6 and was subsequently taken on directly to the next step without further characterization.

Compound 7ae was prepared from 2-(2-Amino-ethyl)-benzo[de]isoquinoline-1,3-dione and compounds 6 and was subsequently taken on directly to the next step without further characterization.

Compound 7af was prepared from 2-(3,5-Bis-trifluoromethyl-phenyl)-ethylamine and compound 6 and was subsequently taken on directly to the next step without further characterization.

Compound 7ag was prepared from Phenethyl-(3-phenyl-propyl)-amine and compound 6 and was subsequently taken on directly to the next step without further characterization.

Compound 7ah was prepared from 2-(4-Trifluoromethyl-phenyl)-ethylamine and compound 6 and was subsequently taken on directly to the next step without further characterization.

Compound 7ai was prepared from dioctylamine and compound 6 and was subsequently taken on directly to the next step without further characterization.

Compound 7aj was prepared from 2-(4-Methoxyphenyl) ethylamine and compound 6 and was subsequently taken on directly to the next step without further characterization.

Compound 7ak was prepared from 2-(napthyl)ethylamine and compound 6 and was subsequently taken on directly to the next step without further characterization.

Example 7

General Procedure for Debenzoylation

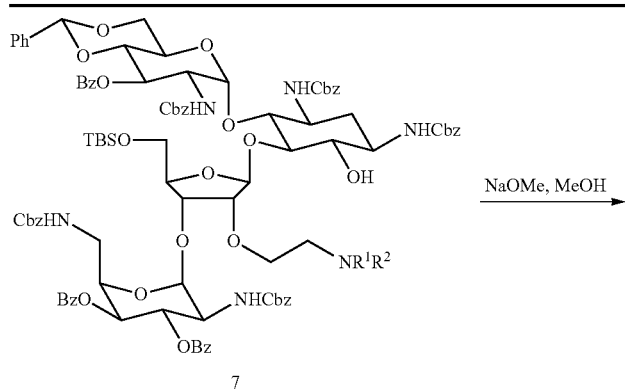

7

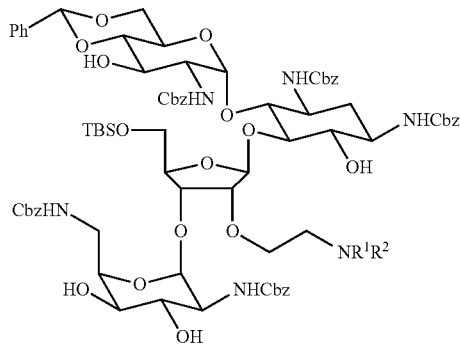

8

-continued
| Compound | R¹ | R² |
|---|---|---|
| 8a | H | 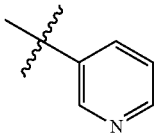 [SMILES: *c1cccnc1] |
| 8b | H | 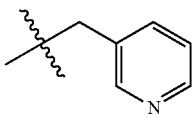 |
| 8c | H | 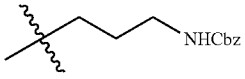 |
| 8d | H | 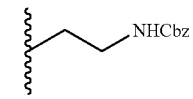 |
| 8e | H | 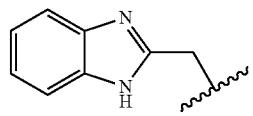 [SMILES: *Cc1nc2ccccc2[nH]1] |
| 8f | H | 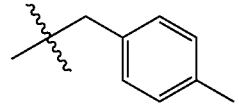 [SMILES: *Cc1ccc(C)cc1] |
| 8g | Me | Me |
| 8h | 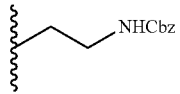 [SMILES: *CCNC(=O)OCc1ccccc1] | 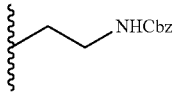 |
| 8i | | |
| 8l | H | 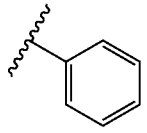 [SMILES: *c1ccccc1] |
| 8m | H | 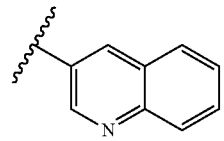 [SMILES: *c1cnc2ccccc2c1] |
| 8n | H | 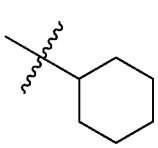 [SMILES: *C1CCCCC1] |

-continued
| | | |
|---|---|---|
| 8o | H | 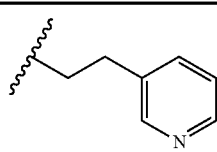 |
| 8p | H | 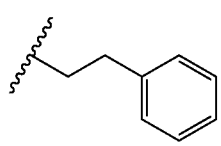 [SMILES: *CCc1ccccc1] |
| 8q | H | 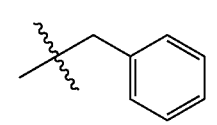 [SMILES: *Cc1ccccc1] |
| 8r | H | 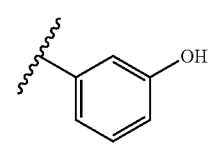 |
| 8s | H | 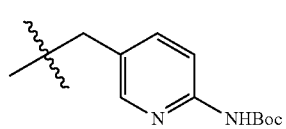 [SMILES: *Cc1ccc(NC(=O)OC(C)(C)C)nc1] |
| 8t | H | 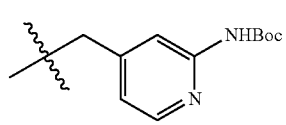 [SMILES: *Cc1ccnc(NC(=O)OC(C)(C)C)c1] |
| 8u | H | 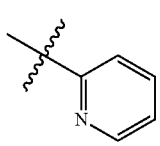 [SMILES: *c1ccccn1] |
| 8v | H | 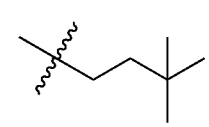 [SMILES: *CCC(C)(C)C] |
| 8w | H | 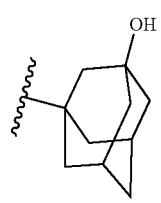 [SMILES: *C12CC3CC(C1)CC(O)(C3)C2] |
| 8x | H | 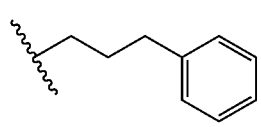 [SMILES: *CCCc1ccccc1] |
| 8y | H | 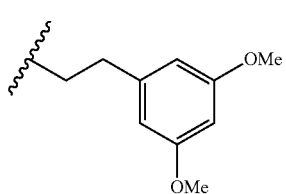 [SMILES: *CCc1cc(OC)cc(OC)c1] |

-continued
| | | |
|---|---|---|
| 8z | H | 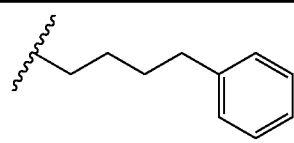 |
| 8aa | H | 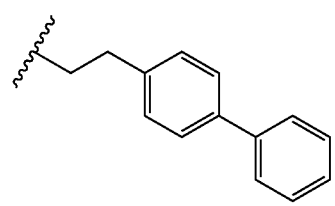 [SMILES: *CCc1ccc(-c2ccccc2)cc1] |
| 8ab | H | 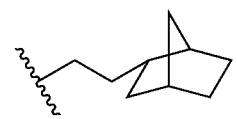 [SMILES: *CCC1CC2CCC1C2] |
| 8ac | H | 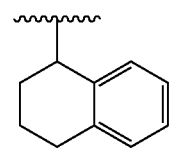 [SMILES: *C1CCCc2ccccc21] |
| 8ad | H | 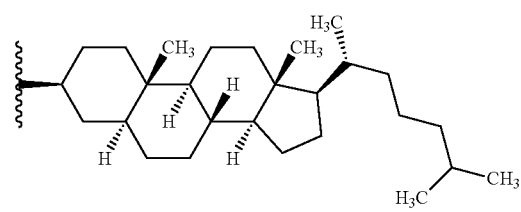 |
| 8ae | H | 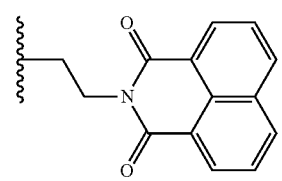 |
| 8af | H | 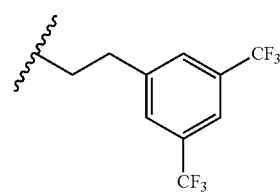 [SMILES: *CCc1cc(C(F)(F)F)cc(C(F)(F)F)c1] |
| 8ag | 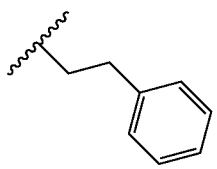 [SMILES: *CCc1ccccc1] | 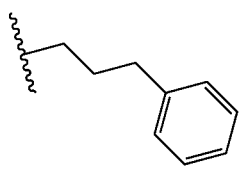 [SMILES: *CCCc1ccccc1] |
| 8ah | H | 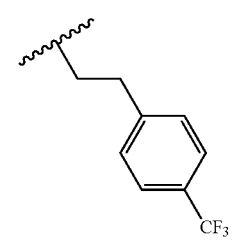 [SMILES: *CCc1ccc(C(F)(F)F)cc1] |

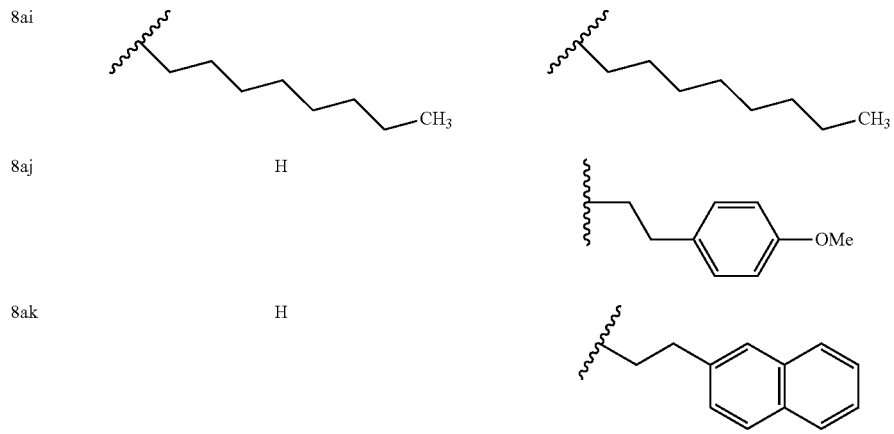

| 8ai | | |
| 8aj | H | |
| 8ak | H | |

The ester was treated with a catalytic amount of NaOMe in MeOH (1:1, 2 mL, pH 9-10) and stirred at room temperature for overnight. The solution was cooled down to −78° C. and dry ice was added, solvent was removed under vacuum and the residue was taken in $CH_2Cl_2$ and filtered over Celite. After removal of the solvent under vacuum the solid was purified by silica gel flash chromatography.

Compound 8a. 95% yield from compound 7a following the general procedure; silica gel flash chromatography eluent: 5% $MeOH/CH_2Cl_2$; $[\alpha]_D$+8.9° (c 1.4, MeOH); $R_f$ 0.2 (5% $MeOH/CH_2Cl_2$); ESI m/z $C_{83}H_{101}N_7O_{24}Si$ 1607.67. found 1630.8 (M+Na);

Compound 8b. 95% yield from compound 7b following the general procedure; silica gel flash chromatography eluent: 5% $MeOH/CH_2Cl_2$; $[\alpha]_D$+10.3° (c 1.1, MeOH); $R_f$ 0.1 (5% $MeOH/CH_2Cl_2$); ESI m/z $C_{84}H_{103}N_7O_{24}Si$ 1621.68. found 1644.8 (M+Na);

Compound 8c. 95% yield from compound 7c following the general procedure; silica gel flash chromatography eluent: 5% $MeOH/CH_2Cl_2$; $R_f$ 0.1 (5% $MeOH/CH_2Cl_2$).

Compound 8d. 95% yield from compound 7d following the general procedure; silica gel flash chromatography eluent: 5% $MeOH/CH_2Cl_2$; $R_f$ 0.1 (5% $MeOH/CH_2Cl_2$);

Compound 8e. 95% yield from compound 7e following the general procedure (the benzylidene and the TBS were removed during the reductive amination); silica gel flash chromatography eluent: 10% $MeOH/CH_2Cl_2$; $[\alpha]_D$+7.3° (c 1.6, MeOH); $R_f$ 0.2 (10% $MeOH/CH_2Cl_2$); ESI m/z $C_{73}H_{86}N_8O_{24}Si$ 1458.58. found 1459.7;

Compound 8f. 95% yield from compound 7f following the general procedure; silica gel flash chromatography eluent: 5% $MeOH/CH_2Cl_2$; $[\alpha]_D$+11.3° (c 0.8), MeOH)$R_f$ 0.1 (5% $MeOH/CH_2Cl_2$). ESI m/z $C_{73}H_{88}N_6O_{24}Si$ 1432.59. found 1433.4;

Compound 8g. 95% yield from compound 7g following the general procedure; silica gel flash chromatography eluent: 10% $MeOH/CH_2Cl_2$; $[\alpha]_D$+11.6° (c 1.1, MeOH); $R_f$ 0.4 (10% $MeOH/CH_2Cl_2$);

Compound 8i. 95% yield from compound 9i following the general procedure; silica gel flash chromatography eluent: 5% $MeOH/CH_2Cl_2$; $[\alpha]_D$+17.6° (c 0.4, MeOH)$R_f$ 0.3 (5% $MeOH/CH_2Cl_2$). ESI m/z $C_{90}H_{112}N_7O_{26}Si$ 1734.74 found 1732.1.

Compound 8l. 82% yield from compound 7l following the general procedure; ESI m/z $C_{87}H_{102}N_6O_{24}Si$ 1607.82. found 1608.9; $^1H$ NMR was taken and is consistent with the structure.

Compound 8m. 79% yield from compound 7m following the general procedure; ESI m/z $C_{87}H_{103}N_7O_{24}Si$ 1658.87. found 1659.9; $^1H$ NMR was taken and is consistent with the structure.

Compound 8n. 80% yield from compound 7n following the general procedure; ESI m/z $C_{84}H_{108}N_6O_{24}Si$ 1613.87. found 1614.9; $^1H$ NMR was taken and is consistent with the structure.

Compound 8o. 86% yield from compound 7o following the general procedure; ESI m/z $C_{85}H_{105}N_7O_{24}Si$ 1636.86. found 1637.2; $^1H$ NMR was taken and is consistent with the structure.

Compound 8p. 82% yield from compound 7p following the general procedure; ESI m/z $C_{86}H_{106}N_6O_{24}Si$ 1635.87. found 1636.0; $^1H$ NMR was taken and is consistent with the structure.

Compound 8q. 78% yield from compound 7q following the general procedure; ESI m/z $C_{85}H_{104}N_6O_{24}Si$ 1621.85. found 1622.1; $^1H$ NMR was taken and is consistent with the structure.

Compound 8r. 78% yield from compound 7r following the general procedure; ESI m/z $C_{84}H_{102}N_6O_{25}Si$ 1623.82. found 1623.8; $^1H$ NMR was taken and is consistent with the structure.

Compound 8s. 81% yield from compound 7s following the general procedure; ESI m/z $C_{89}H_{112}N_8O_{26}Si$ 1737.97. found 1738.9; $^1H$ NMR was taken and is consistent with the structure.

Compound 8t. 86% yield from compound 7t following the general procedure; ESI m/z $C_{89}H_{112}N_8O_{26}Si$ 1737.97. found 1738.2; $^1H$ NMR was taken and is consistent with the structure.

Compound 8u. 85% yield from compound 7u following the general procedure; ESI m/z $C_{83}H_{101}N_7O_{24}Si$ 1608.81. found 1608.8; $^1H$ NMR was taken and is consistent with the structure.

Compound 8v. 72% yield from compound 7v following the general procedure; ESI m/z $C_{84}H_{110}N_6O_{24}Si$ 1615.88. found 1615.8; $^1H$ NMR was taken and is consistent with the structure.

Compound 8w. 91% yield from compound 7w following the general procedure; ESI m/z $C_{88}H_{112}N_6O_{25}Si$ 1681.94. found 1681.6; $^1H$ NMR was taken and is consistent with the structure.

Compound 8x. 90% yield from compound 7x following the general procedure; ESI m/z $C_{87}H_{108}N_6O_{24}Si$ 1649.90. found 1671.9 (M+Na); $^1H$ NMR was taken and is consistent with the structure.

Compound 8y. 84% yield from compound 7y following the general procedure; ESI m/z $C_{88}H_{110}N_6O_{26}Si$ 1695.93. found 1695.9; $^1H$ NMR was taken and is consistent with the structure.

Compound 8z. 95% yield from compound 7z following the general procedure; ESI m/z $C_{88}H_{110}N_6O_{24}Si$ 1663.93. found 1686.1 (M+Na); $^1H$ NMR was taken and is consistent with the structure.

Compound 8aa. 81% yield from compound 7aa following the general procedure; ESI m/z $C_{92}H_{110}N_6O_{24}Si$ 1711.97. found 1711.9; $^1H$ NMR was taken and is consistent with the structure.

Compound 8ab. 73% yield from compound 7ab following the general procedure; ESI m/z $C_{87}H_{112}N_6O_{24}Si$ 1652.75. found 1653.7; $^1H$ NMR was taken and is consistent with the structure.

Compound 8ac. 80% yield from compound 7ac following the general procedure; ESI m/z $C_{88}H_{108}N_6O_{24}Si$ 1661.91. found 1661.6; $^1H$ NMR was taken and is consistent with the structure.

Compound 8ad. 87% yield from compound 7ad following the general procedure; ESI m/z $C_{105}H_{144}N_6O_{24}Si$ 1902.38. found 1902.2; $^1H$ NMR was taken and is consistent with the structure.

Compound 8ae. 70% yield from compound 7e following the general procedure; ESI m/z $C_{92}H_{107}N_7O_{26}Si$ 1754.95. found 1755.7; $^1H$ NMR was taken and is consistent with the structure.

Compound 8af. 85% yield from compound 7af following the general procedure; ESI m/z $C_{88}H_{104}F_6N_6O_{24}Si$ 1771.87. found 1771.5; $^1H$ NMR was taken and is consistent with the structure.

Compound 8ag. 88% yield from compound 7ag following the general procedure; ESI m/z $C_{95}H_{116}N_6O_{24}Si$ 1754.05. found 1756.4; $^1H$ NMR was taken and is consistent with the structure.

Compound 8ah. 94% yield from compound 7ah following the general procedure; ESI m/z $C_{87}H_{105}F_3N_6O_{24}Si$ 1703.87. found 1703.5; $^1H$ NMR was taken and is consistent with the structure.

Compound 8ai. 95% yield from compound 7ai following the general procedure; ESI m/z $C_{94}H_{130}N_6O_{24}Si$ 1756.15. found 1756.3; $^1H$ NMR was taken and is consistent with the structure.

Compound 8aj. 83% yield from compound 7aj following the general procedure; ESI m/z $C_{87}H_{108}N_6O_{25}Si$ 1665.9. found 1665.6; $^1H$ NMR was taken and is consistent with the structure.

Compound 8ak was prepared from compound 7ak following the general procedure and was subsequently taken on directly to the next step without further characterization.

Example 8

General Procedure for Final Deprotection

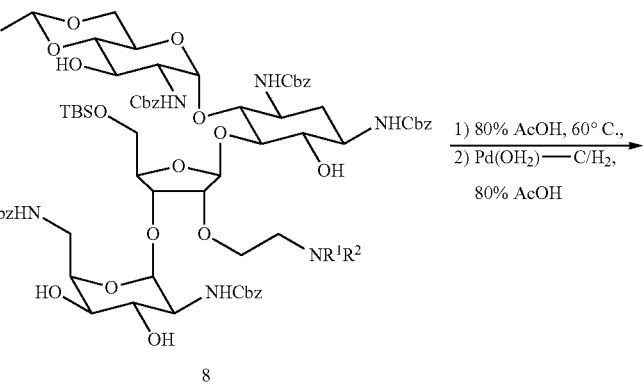

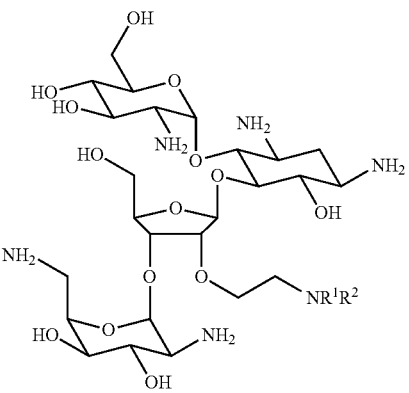

-continued
| Compound | R¹ | R² |
|---|---|---|
| 9a | H | 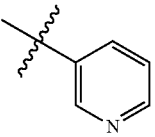 3-pyridyl |
| 9b | H | 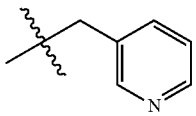 [SMILES: *Cc1cccnc1] 3-pyridylmethyl |
| 9c | H | 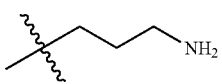 [SMILES: *CCCN] -(CH₂)₃NH₂ |
| 9d | H | 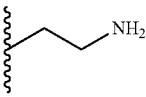 [SMILES: *CCN] -CH₂NH₂ |
| 9e | H | 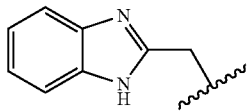 [SMILES: *Cc1nc2ccccc2[nH]1] benzimidazol-2-ylmethyl |
| 9f | H | H |
| 9g | Me | Me |
| 9h | 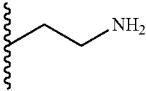 [SMILES: *CCN] -CH₂CH₂NH₂ | 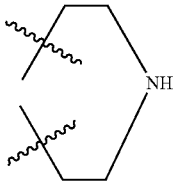 [SMILES: *CCNCC*] -CH₂CH₂NH₂ |
| 9i | (R¹ and R² joined) 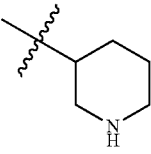 [SMILES: *C1CCCNC1] | |
| 9j | H | 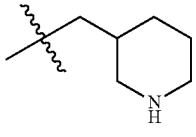 [SMILES: *CC1CCCNC1] piperidin-3-yl |
| 9k | H | 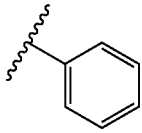 [SMILES: *c1ccccc1] piperidin-3-ylmethyl |
| 9l | H | phenyl |

-continued
| | | |
|---|---|---|
| 9m | H | 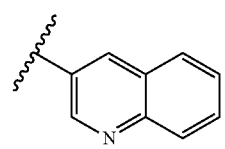 [SMILES: *c1cnc2ccccc2c1] |
| 9n | H | 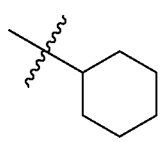 |
| 9o | H | 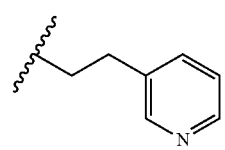 [SMILES: *CCc1cccnc1] |
| 9p | H | 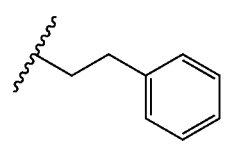 [SMILES: *CCc1ccccc1] |
| 9q | H | 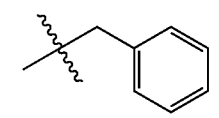 [SMILES: *Cc1ccccc1] |
| 9r | H | 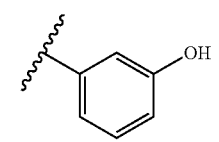 [SMILES: *c1cccc(O)c1] |
| 9s | H | 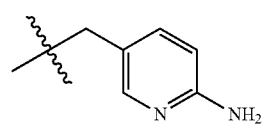 [SMILES: *Cc1ccc(N)nc1] |
| 9t | H | 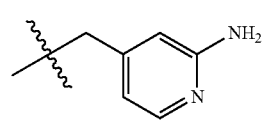 [SMILES: *Cc1ccnc(N)c1] |
| 9u | H | 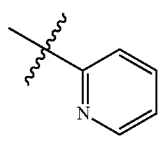 |
| 9v | H | 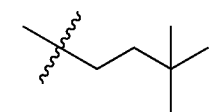 [SMILES: *CCC(C)(C)C] |
| 9w | H | 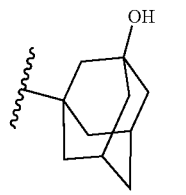 |

-continued
| | | |
|---|---|---|
| 9x | H | 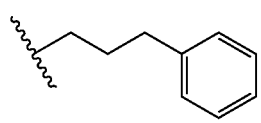 [SMILES: *CCCc1ccccc1] |
| 9y | H | 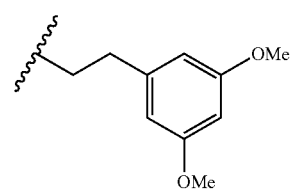 |
| 9z | H | 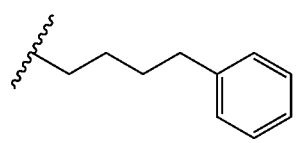 [SMILES: *CCCCc1ccccc1] |
| 9aa | H | 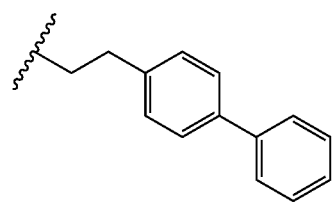 [SMILES: *CCc1ccc(-c2ccccc2)cc1] |
| 9ab | H | 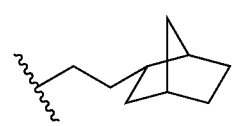 [SMILES: *CCC1CC2CCC1C2] |
| 9ac | H | 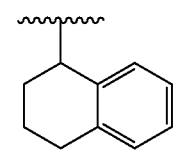 |
| 9ad | H | 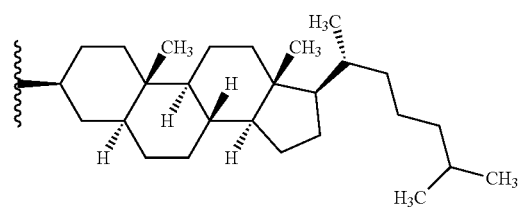 |
| 9ae | H | 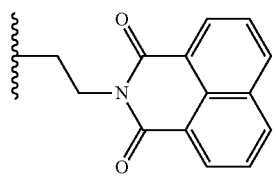 [SMILES: *CCN1C(=O)c2cccc3cccc(c23)C1=O] |
| 9af | H | 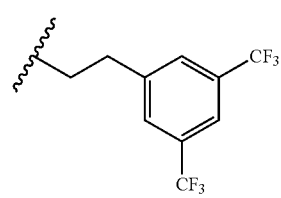 [SMILES: *CCc1cc(C(F)(F)F)cc(C(F)(F)F)c1] |

| | | |
|---|---|---|
| 9ag | 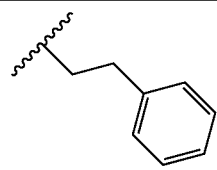 | 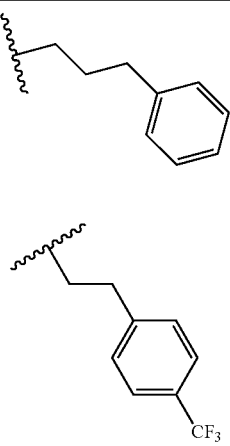 |
| 9ah | H | |
| 9ai | 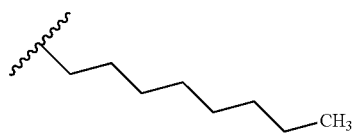 [SMILES: *CCCCCCCC] | 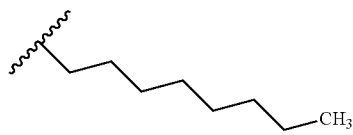 [SMILES: *CCCCCCCC] |
| 9aj | H | 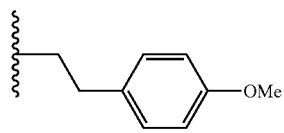 [SMILES: *CCc1ccc(OC)cc1] |
| 9ak | H | 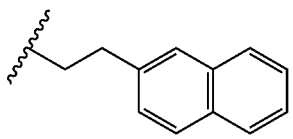 [SMILES: *CCc1ccc2ccccc2c1] |

The appropriate substrate was dissolved in 80% aqueous acetic acid (3 mL) and heated at 60° C. for 3 hours The solution was cooled down to room temperature and a catalytic amount of 20% palladium hydroxide on carbon was added and the suspension was stirred at room temperature under an atmosphere of hydrogen (hydrogen balloon) until the conversion of the starting material into the product was completed as indicated by MS analysis. The mixture was filtered through a layer of Celite on cotton, concentrated under vacuum, washed with $CH_2Cl_2$ and lyophilized to afford floppy white solids.

Compound 9a. Quantitative yield from compound 8a following the general procedure; $[\alpha]_D$+6.8° (c 0.4, $H_2O$); $^1H$ NMR (400 MHz, $D_2O$) δ 8.00-7.70 (m, 2H), 7.60-7.40 (m, 2H), 5.70 (m, 1H), 5.33 (m, 1H), 5.11 (m, 1H), 4.50 (m, 1H), 4.20-4.00 (m, 4H), 3.85-3.50 (m, 13H), 3.40-3.15 (m, 8H), 2.37 (m, 1H), 1.79 (s, 18H), 1.70 (m, 1H); $^{13}C$ NMR (125 MHz, $D_2O$) δ 181.4, 132.3, 131.6, 129.5, 129.2, 128.7, 127.1, 126.8, 108.8, 96.2, 95.3, 85.3, 81.6, 81.0, 78.0, 74.1, 73.1, 70.7, 69.6, 69.3, 68.0, 67.7, 60.7, 60.3, 54.2, 51.5, 50.3, 49.2, 43.0, 40.7, 29.2, 23.5; ESI m/z $C_{30}H_{53}N_7O_{14}$ 735.37. found 736.5;

Compound 9b. Quantitative yield from compound 8b following the general procedure; $[\alpha]_D$+5.4° (c 0.6, $H_2O$); $^1H$ NMR (400 MHz, $D_2O$) δ 7.70-7.30 (m, 4H), 5.71 (m, 1H), 5.38 (m, 1H), 5.16 (m, 1H), 4.55 (m, 1H), 4.20-4.00 (m, 4H), 3.95-3.50 (m, 15H), 3.45-3.15 (m, 8H), 2.32 (m, 1H), 1.81 (s, 18H), 1.65-1.40 (m, 1H); $^{13}C$ NMR (125 MHz, $D_2O$) δ 181.4, 150.5, 140.0, 133.9, 132.8, 129.8, 129.1, 128.9, 128.2, 125.5, 109.0, 96.6, 95.7, 85.7, 81.4, 78.5, 74.3, 73.7, 71.1, 69.9, 68.5, 68.1, 61.0, 60.1, 54.6, 51.6, 50.8, 49.6, 46.6, 41.1, 31.8, 29.7, 23.5; ESI m/z $C_{31}H_{55}N_7O_{14}$ 749.38. found 750.4;

Compound 9c. Quantitative yield from compound 8c following the general procedure; $[\alpha]_D$+5.7° (c 0.4, $H_2O$); $^1H$ NMR (400 MHz, $D_2O$) δ 5.72 (m, 1H), 5.44 (m, 1H), 5.21 (m, 1H), 4.59 (m, 1H), 4.20-4.00 (m, 4H), 3.95-3.50 (m, 13H), 3.45-2.7 (m, 14H), 2.26 (m, 1H), 1.87 (s, 21H), 1.59 (m, 1H); $^{13}C$ NMR (125 MHz, $D_2O$) δ 182.2, 108.9, 96.8, 96.0, 86.0, 81.8, 79.8, 74.5, 74.3, 71.3, 71.2, 70.1, 68.6, 68.2, 67.5, 61.0, 54.8, 51.8, 51.1, 50.3, 49.8, 48.8, 45.5, 43.7, 41.1, 37.3, 31.1, 27.4, 24.5, 24; ESI m/z $C_{28}H_{57}N_7O_{14}$ 715.40. found 716.4;

Compound 9d. Quantitative yield from compound 8d following the general procedure; $[\alpha]_D$+8.1° (c 0.6, $H_2O$); $^1H$ NMR (400 MHz, $D_2O$) δ 5.75 (m, 1H), 5.44 (m, 1H), 5.20 (m, 1H), 4.30-4.00 (m, 4H), 3.85-3.50 (m, 13H), 3.40-3.15 (m, 8H), 3.00-2.55 (m, 4H) 2.31 (m, 1H), 1.91 (s, 21H), 1.63 (m, 1H); ESI m/z $C_{27}H_{55}N_7O_{14}$ 701.38. found 702.6;

Compound 9e. Quantitative yield from compound 8e following the general procedure; $[\alpha]_D$+8.6° (c 0.7, $H_2O$); $^1H$ NMR (400 MHz, $D_2O$) δ 7.80-7.40 (m, 4H), 5.81 (m, 1H), 5.44 (m, 1H), 5.24 (m, 1H), 4.35-4.10 (m, 4H), 3.95-3.50 (m, 14H), 3.45-3.15 (m, 8H), 2.42 (m, 1H), 1.91 (s, 18H), 1.61 (m, 1H); ESI m/z $C_{33}H_{56}N_8O_{14}$ 788.39. found 789.5;

Compound 9f. Quantitative yield from compound 8f following the general procedure; $[\alpha]_D$+10.6° (c 0.7, H$_2$O); $^1$H NMR (400 MHz, D$_2$O) δ 5.78 (m, 1H), 5.46 (m, 1H), 5.26 (m, 1H), 4.30-4.00 (m, 6H), 3.95-3.50 (m, 14H), 3.45-3.00 (m, 6H), 2.35 (m, 1H), 1.91 (s, 21H), 1.71 (m, 1H); ESI m/z C$_{25}$H$_{50}$N$_6$O$_{14}$ 658.33. found 659.4;

Compound 9g. Quantitative yield from compound 8g following the general procedure; $[\alpha]_D$+7.3° (c 0.6, H$_2$O); $^1$H NMR (400 MHz, D$_2$O) δ 5.76 (m, 1H), 5.46 (m, 1H), 5.26 (m, 1H), 4.62 (m, 1H), 4.41-4.04 (m, 5H, 3.90-3.50 (m, 14H), 3.45-3.20 (m, 6H), 2.9 (s, 6H) 2.33 (m, 1H), 1.88 (s, 18H), 1.70 (m, 1H); $^{13}$C NMR (125 MHz, D$_2$O) δ 182.0, 108.8, 96.7, 95.6, 85.8, 81.4, 81.2, 78.9, 74.3, 74.2, 73.9, 71.2, 69.9, 69.8, 68.5, 68.0, 64.9, 60.9, 59.9, 57.5, 54.7, 51.7, 50.9, 49.6, 43.6 (2C), 41.1, 30.2, 23.9; ESI m/z C$_{27}$H$_{54}$N$_6$O$_{14}$ 686.4. found 687.4;

Compound 9h. Quantitative yield from compound 8h following the general procedure; $[\alpha]_D$+21.5° (c 0.6, H$_2$O); $^1$H NMR (400 MHz, D$_2$O) δ 5.55 (m, 1H), 5.16 (m, 1H), 5.08 (m, 1H), 4.49 (m, 1H), 4.30-4.00 (m, 5H, 3.95-3.40 (m, 14H), 3.45-3.15 (m, 6H), 2.58 (m, 8H) 2.18 (m, 1H), 1.92 (s, 24H), 1.30 (m, 1H); ESI m/z C$_{29}$H$_{60}$N$_8$O$_{14}$ 744.42. found 745.6;

Compound 9i. Quantitative yield from compound 8i following the general procedure; $[\alpha]_D$+14.5° (c 0.7, H$_2$O); NMR (400 MHz, D$_2$O) δ 5.70 (m, 1H), 5.35 (m, 1H), 5.12 (m, 1H), 4.49 (m, 1H), 4.30-4.00 (m, 5H, 3.95-3.40 (m, 14H), 3.45-3.05 (m, 10H), 2.68 (m, 4H), 2.26 (m, 1H), 1.87 (s, 21H), 1.62 (m, 1H); $^{13}$C NMR (125 MHz, D$_2$O) δ 181.6, 108.9, 96.6, 95.9, 87.5, 81.9, 81.6, 78.5, 74.6, 74.5, 73.7, 71.2, 70.0, 69.8, 68.5, 68.1, 68.0, 61.0, 60.6, 57.2, 54.7, 51.8, 51.1, 50.8, 50.2 (2), 49.7, 43.6 (2C), 41.1, 31.1, 23.6; ESI m/z C$_{29}$H$_{58}$N$_7$O$_{14}$ 728.40. found 728.3;

Compound 9j. Prepared by extened hydrogenation via 9a. quantitative; $[\alpha]_D$+7.8° (c 1.0, H$_2$O); $^1$H NMR (400 MHz, D$_2$O) δ 5.66 (m, 1H), 5.30 (m, 1H), 5.11 (m, 1H), 4.46 (m, 1H), 4.20-4.00 (m, 5H, 3.95-3.50 (m, 14H), 3.40-2.95 (m, 11H), 2.37 (m, 1H), 2.1-1.9 (m, 4H) 1.79 (s, 18H), 1.70 (m, 1H); $^{13}$C NMR (125 MHz, D$_2$O) δ 181.0, 108.9, 96.6, 95.7, 90.9, 85.5, 81.5, 77.7, 74.5, 74.3, 73.3, 71.1, 69.9, 69.5, 68.4, 68.3, 68.0, 61.0, 54.5, 52.4, 51.5, 50.6, 49.4, 44.7, 44.2, 41.0, 40.1, 34.5, 28.9, 23.3 20.9, 20.2; ESI m/z C$_{30}$H$_{59}$N$_7$O$_{14}$ 741.41. found 742.7;

Compound 9k. Prepared by extened hydrogenation via 9b. quantitative; $[\alpha]_D$+12.4° (c 1.1, H$_2$O); $^1$H NMR (400 MHz, D$_2$O) δ, 5.67 (m, 1H), 5.32 (m, 1H), 5.25 (m, 1H), 4.48 (m, 1H), 4.20-4.00 (m, 5H), 3.95-3.30 (m, 18H), 3.30-3.00 (m, 12H), 2.21 (m, 1H), 1.81 (s, 21H), 1.62 (m, 1H); $^{13}$C NMR (125 MHz, D$_2$O) δ 180.3, 108.5, 96.2, 95.2, 85.0, 81.1, 80.8, 77.2, 74.1 (2C), 72.9, 70.7, 69.4, 69.1, 67.9, 67.5, 60.5, 60.1, 54.1, 51.1, 50.3, 50.2, 49.1, 48.9, 46.1, 44.2, 44.1, 40.6, 30.3, 28.6, 22.75, 22.1, 21.4, 18.2; ESI m/z C$_{31}$H$_{61}$N$_7$O$_{14}$ 755.42. found 756.7.

Compound 9l. 80% yield from compound 8l following the general procedure; ESI m/z C$_{31}$H$_{54}$N$_6$O$_{14}$ 734.79. found 735.5; $^1$H NMR is consistent with the structure.

Compound 9m. 85% yield from compound 8m following the general procedure; ESI m/z C$_{34}$H$_{55}$N$_7$O$_{14}$ 785.84. found 786.5; $^1$H NMR is consistent with the structure.

Compound 9n. 85% yield from compound 8n following the general procedure; ESI m/z C$_{31}$H$_{60}$N$_6$O$_{14}$ 740.84. found 741.5; $^1$H NMR is consistent with the structure.

Compound 9o. 85% yield from compound 8o following the general procedure; ESI m/z C$_{32}$H$_{57}$N$_7$O$_{14}$ 763.83. found 764.7; $^1$H NMR is consistent with the structure.

Compound 9p. 80% yield from compound 8p following the general procedure; ESI m/z C$_{33}$H$_{58}$N$_6$O$_{14}$ 762.85. found 763.6; $^1$H NMR is consistent with the structure.

Compound 9q. 85% yield from compound 8q following the general procedure; ESI m/z C$_{32}$H$_{56}$N$_6$O$_{14}$ 748.82. found 749.6; $^1$H NMR is consistent with the structure.

Compound 9r. 85% yield from compound 8r following the general procedure; ESI m/z C$_{31}$H$_{54}$N$_6$O$_{15}$ 750.79. found 751.6; $^1$H NMR is consistent with the structure.

Compound 9s. 60% yield from compound 8s following the general procedure; ESI m/z C$_{31}$H$_{56}$N$_8$O$_{14}$ 764.82. found 765.6; $^1$H NMR is consistent with the structure.

Compound 9t. 65% yield from compound 8t following the general procedure; ESI m/z C$_{31}$H$_{56}$N$_8$O$_{14}$ 764.82. found 765.6; $^1$H NMR is consistent with the structure.

Compound 9u. 75% yield from compound 8u following the general procedure; ESI m/z C$_{30}$H$_{53}$N$_7$O$_{14}$ 735.78. found 736.5; $^1$H NMR is consistent with the structure.

Compound 9v. 80% yield from compound 8v following the general procedure; ESI m/z C$_{31}$H$_{62}$N$_6$O$_{14}$ 742.86. found 743.4; $^1$H NMR is consistent with the structure.

Compound 9w. 80% yield from compound 8w following the general procedure; ESI m/z C$_{35}$H$_{64}$N$_6$O$_{15}$ 808.91. found 809.4; $^1$H NMR is consistent with the structure.

Compound 9x. 90% yield from compound 8x following the general procedure; ESI m/z C$_{34}$H$_{60}$N$_6$O$_{14}$ 776.87. found 777.6; $^1$H NMR is consistent with the structure.

Compound 9y. 90% yield from compound 8y following the general procedure; ESI m/z C$_{35}$H$_{62}$N$_6$O$_{16}$ 822.90. found 823.5; $^1$H NMR is consistent with the structure.

Compound 9z. 90% yield from compound 8z following the general procedure; ESI m/z C$_{35}$H$_{62}$N$_6$O$_{14}$ 790.90. found 791.7; $^1$H NMR is consistent with the structure.

Compound 9aa. 85% yield from compound 8aa following the general procedure; ESI m/z C$_{39}$H$_{62}$N$_6$O$_{14}$ 838.94. found 839.5; $^1$H NMR is consistent with the structure.

Compound 9ab. 80% yield from compound 8ab following the general procedure; ESI m/z C$_{34}$H$_{64}$N$_6$O$_{14}$ 780.90. found 781.5; $^1$H NMR is consistent with the structure.

Compound 9ac. 90% yield from compound 8ac following the general procedure; ESI m/z C$_{35}$H$_{60}$N$_6$O$_{14}$ 788.88. found 789.5; $^1$H NMR is consistent with the structure.

Compound 9ad. 80% yield from compound 8ad following the general procedure; ESI m/z C$_{52}$H$_{96}$N$_6$O$_{14}$ 1029.35. found 1029.7; $^1$H NMR is consistent with the structure.

Compound 9ae. 75% yield from compound 8ae following the general procedure; ESI m/z C$_{39}$H$_{59}$N$_7$O$_{16}$ 881.92. found 882.5; $^1$H NMR is consistent with the structure.

Compound 9af. 90% yield from compound 8af following the general procedure; ESI m/z C$_{35}$H$_{56}$F$_6$N$_6$O$_{14}$ 898.84. found 899.4; $^1$H NMR is consistent with the structure.

Compound 9ag. 90% yield from compound 8ag following the general procedure; ESI m/z C$_{48}$H$_{68}$N$_6$O$_{14}$ 881.02. found 883.8; $^1$H NMR is consistent with the structure.

Compound 9ah. 85% yield from compound 8ah following the general procedure; ESI m/z C$_{34}$H$_{57}$F$_3$N$_6$O$_{14}$ 830.84. found 831.5; $^1$H NMR is consistent with the structure.

Compound 9ai. 80% yield from compound 8ai following the general procedure; ESI m/z C$_{41}$H$_{82}$N$_6$O$_{14}$ 883.12. found 883.9; $^1$H NMR is consistent with the structure.

Compound 9aj. 90% yield from compound 8aj following the general procedure; ESI m/z C$_{34}$H$_{60}$N$_6$O$_{15}$ 792.87. found 793.7; $^1$H NMR is consistent with the structure.

Compound 9ak was prepared from compound 8ak following the general procedure.

Example 9

Preparation of Compounds 10 and 11

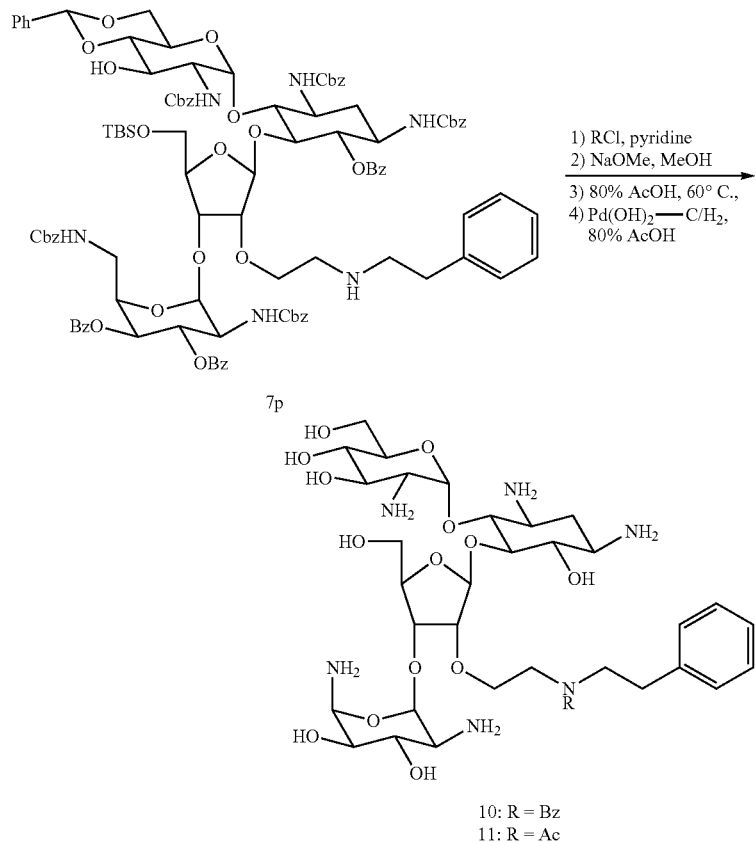

Compound 7p is treated with the appropriate acyl chloride (1.2 equiv) and then deprotected according to the general procedure to give 10 (benzoyl chloride) and 11 (acetyl chloride).

Compound 10. 75% yield from compound 7p and benzoyl chloride following the general procedure; ESI m/z $C_{40}H_{62}N_6O_{15}$ 866.97. found 867.5; $^1$H NMR is consistent with the structure.

Compound 11. 80% yield from compound 7p and acetyl chloride following the general procedure; ESI m/z $C_{35}H_{60}N_6O_{15}$ 804.88. found 806.3; $^1$H NMR is consistent with the structure.

Example 10
Preparation of C2''-Alkoxy Ether Paromomycin

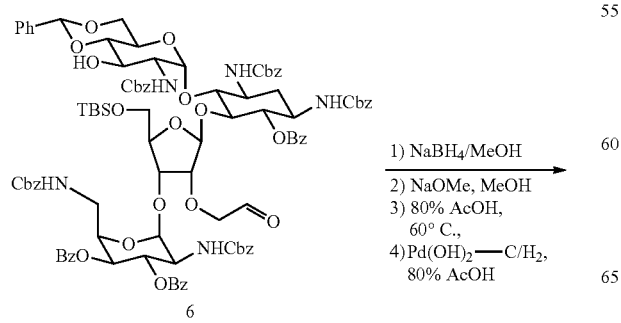

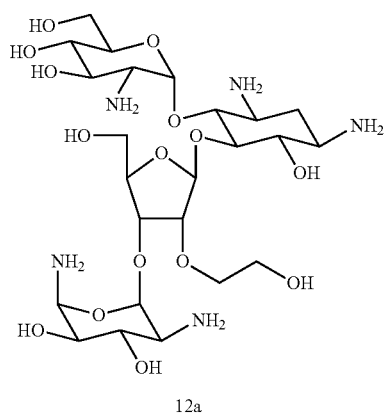

Compound 6 is treated with 5-10 equivalents of sodium borohydride in methanol, and then deprotected according to the general procedure to give compound 12a.

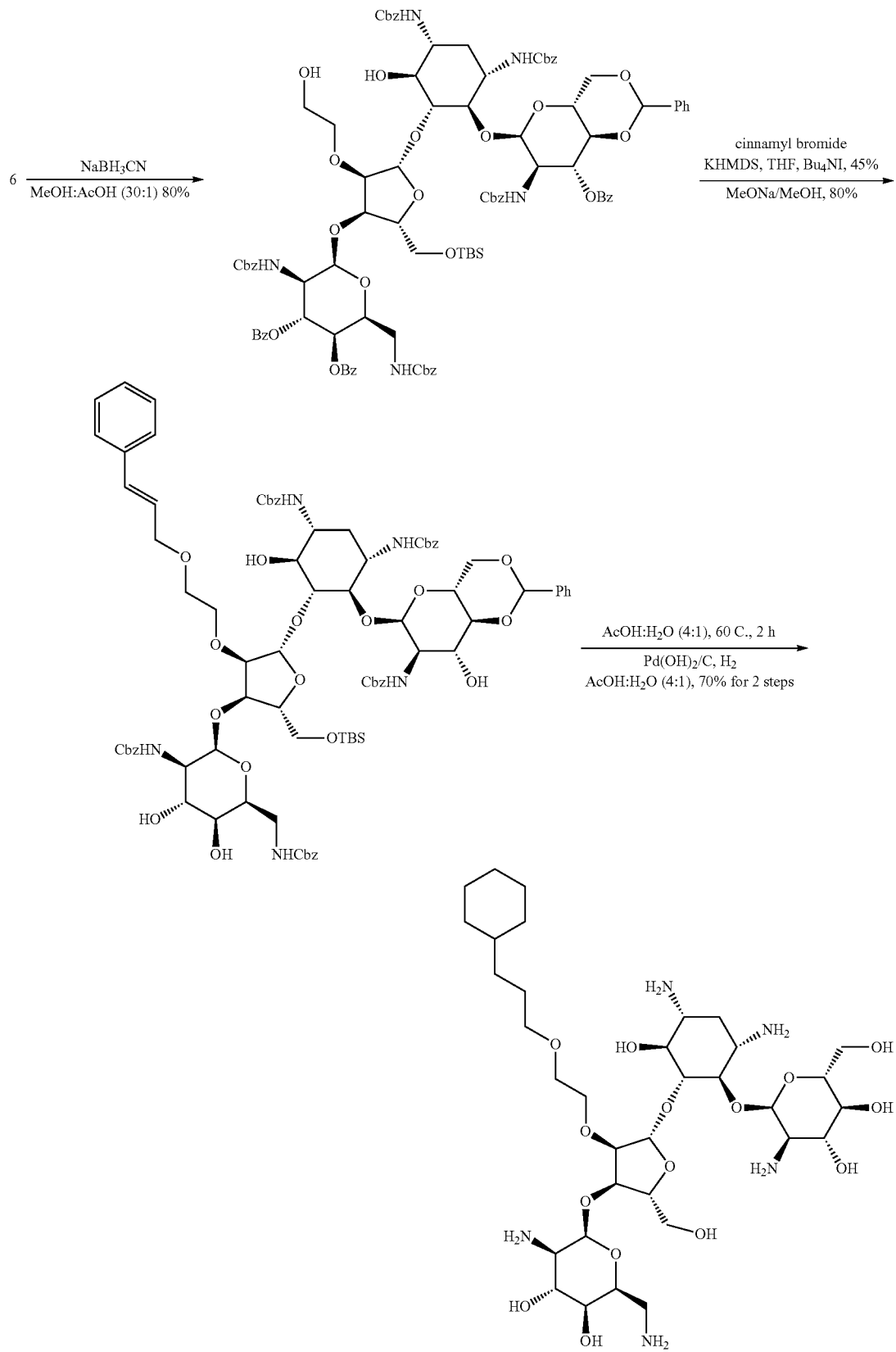

Compound 12a. 80% yield; ESI m/z $C_{25}H_{49}N_5O_{15}$ 659.68. found 660.51; $^1$H NMR is consistent with the structure.

Compound 12b was prepared according to the above reaction scheme. Reduction of 6 led to the first intermediate. Standard alkylation of the first intermediate with cinnamyl bromide gave the expected second intermediate, which upon deprotection afforded 12b in which the phenyl ring had undergone overreduction to a cyclohexyl moiety.

Example 11

Preparation of Compound 13

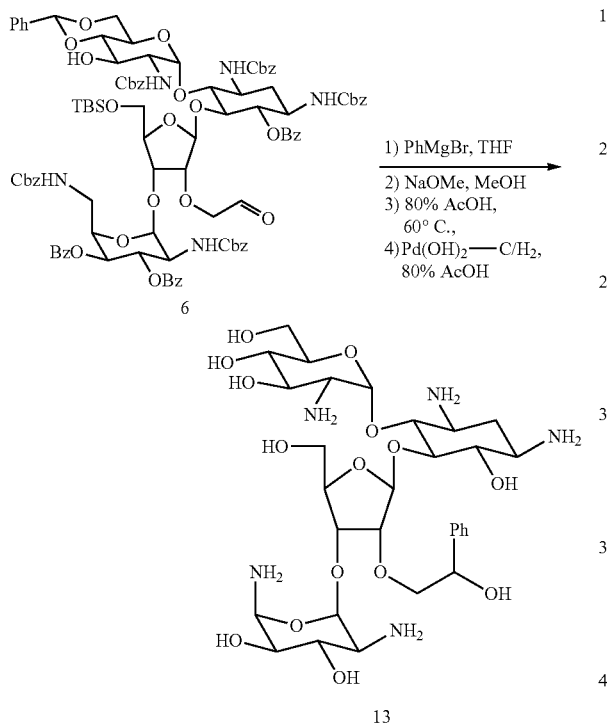

Compound 6 is treated with 1-2 equivalents of phenylmagnesiumbromide or diphenyl zinc in THF, and then deprotected according to the general procedure to give compound 13.

Compound 13. 65% yield; ESI m/z $C_{31}H_{53}N_5O_{15}$ 735.78. found 736.8; $^1$H NMR is consistent with the structure.

Example 12

Preparation of 2″-Alkyl/Aryl Ether Paromomycin

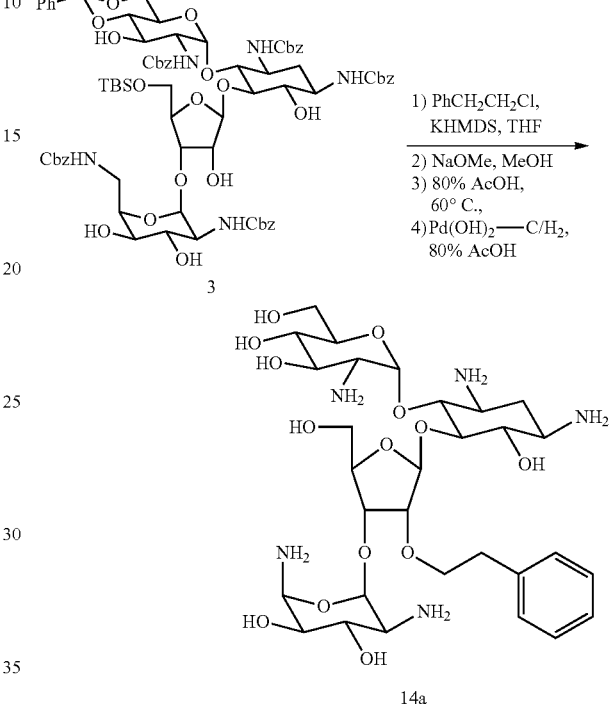

Compound 3 (2.10 g, 1.411 mmol) was dissolved in dry THF (70 mL) and phenethyl chloride (10 equiv) was added followed by the dropwise addition of 0.5 M KHMDS solution in toluene (1.411 mL, 0.706 mmol). The mixture was stirred for overnight at room temperature, and then deprotected according to the general procedures to provide phenethyl ether 14a.

Compound 14a. 85% yield; ESI m/z $C_{31}H_{53}N_5O_{14}$ 719.78. found 720.9; $^1$H NMR is consistent with the structure.

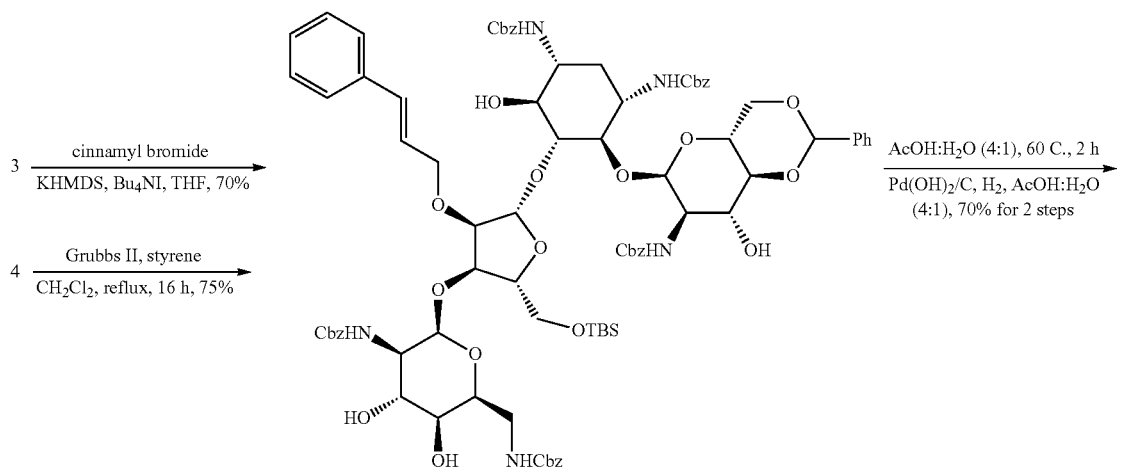

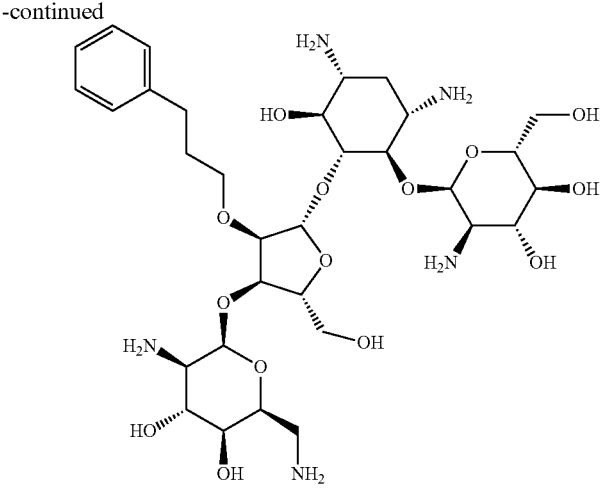

14b

Compound 14b was prepared according to the above reaction scheme. Direct alkylation of Compound 3 with cinnamyl bromide in the presence of KHMDS and Bu$_4$NI at 0° C. gave the intermediate product in 70% yield. Alternatively, the intermediate product could also be obtained by performing a cross-metathesis reaction of Compound 4 with styrene in the presence of the Grubbs second generation catalyst in 75% yield (see Scholl, M.; Ding, S.; Lee, C. W.; Grubbs, R. H. *Org. Lett.* 1999, 1, 953). Cleavage of the benzylidene acetal as well as the OTBS ether followed by catalytic hydrogenolysis gave Compound 14b.

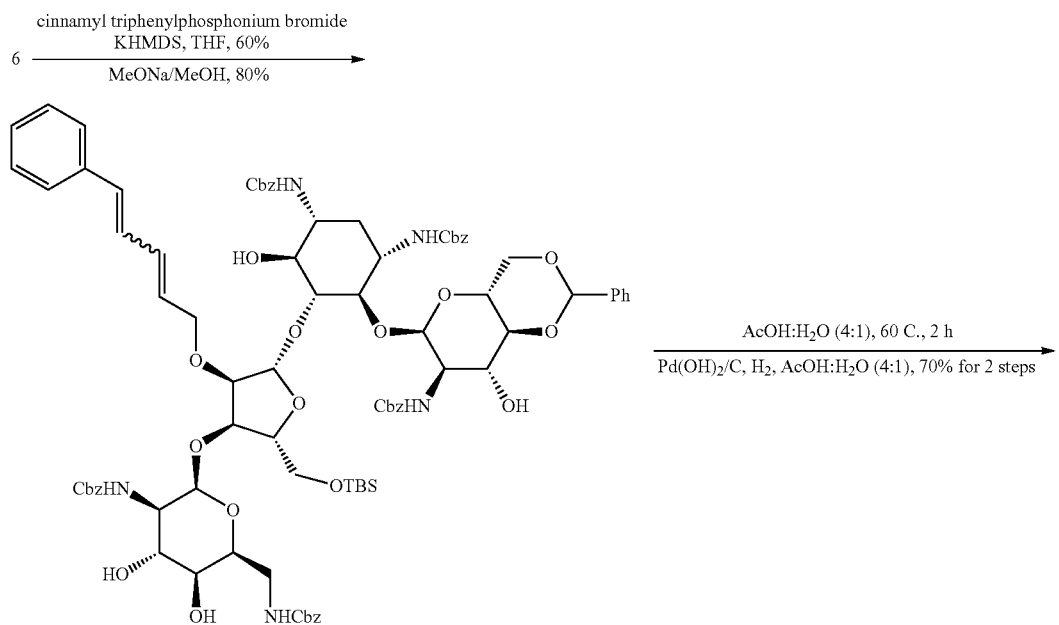

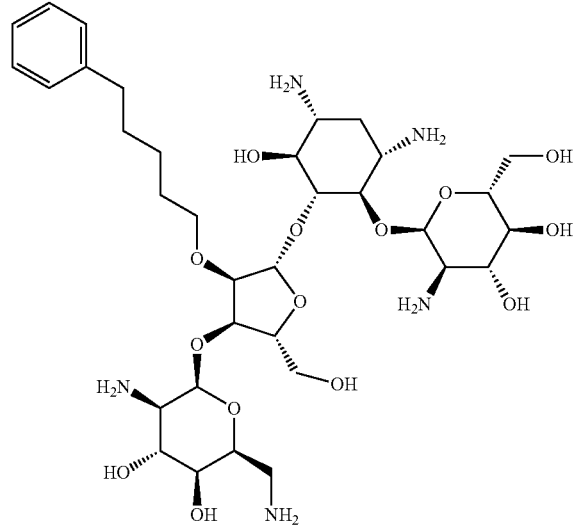

14c

Compound 14c was prepared according to the above reaction scheme. A Wittig reaction of 6 gave the intermediate as a mixture of isomeric olefins. Deprotection and hydrogenation afforded the 5-phenylpentyl ether analogue 14c.

Example 13

Preparation of N-Protected Paromomycin

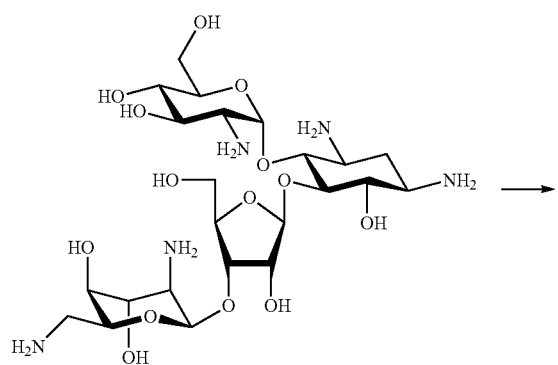

The exocyclic amino groups of Paromomycin were converted into the corresponding azido groups according to the procedure of Wong (Greenberg, W. A.; Priestley, E. S.; Sears, P. S.; Alper, P. B.; Rosenbohm, C. et al. Design and Synthesis of New Aminoglycoside Antibiotics Containing Neamine as an Optimal Core Structure: Correlation of Antibiotic Activity with in Vitro Inhibition of Translation. *J. Am. Chem. Soc.* 1999, 121, 6527-6541) using paromomycin instead of neomycin.

$^1$H NMR (300 MHz, DMSO) δ 1.36 (q, J=12 Hz, 1H), δ 1.99-2.06 (m, 1H) δ 3.37-3.73 (m, 1H) δ 2.97-3.02 (m, 1H), δ 3.19-3.27 (m, 1H), δ 3.37-3.73 (m, 15H), δ 3.88-3.95 (m, 2H), δ 4.16-4.25 (m, 2H), δ 4.44 (t, J=5.7 Hz, 1H) δ 4.75 (t, J=4.8 Hz, 1H), δ 4.93 (d, J=5.2 Hz, 1H), δ 5.03 (d, J=1.6 Hz, 1H), δ 5.15 (d, J=5.1 Hz, 1H) δ 5.22 (d, J=4.6 Hz, 1H), δ 5.28 (s, 1H), δ 5.39 (d, J=5.7 Hz, 1H), δ 5.59 (t, J=4.8 Hz, 2H), δ 5.67 (d, J=3.7 Hz, 1H); $^{13}$C NMR δ 106.97, 97.64, 95.89, 83.22, 81.67, 75.60, 74.66, 74.13, 72.98, 72.80, 70.30, 70.00, 69.81, 66.99, 63.0261.50, 60.40, 59.85, 59.66, 59.21, 50.77, 31.46 LCMS m/z 768.0 (M+Na), (>99% purity).

Example 14

Selective Protection of the 6'-Position with Tips

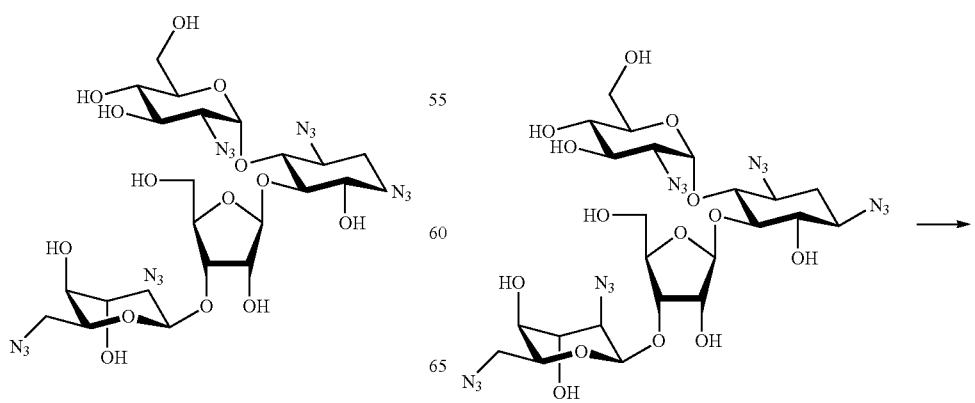

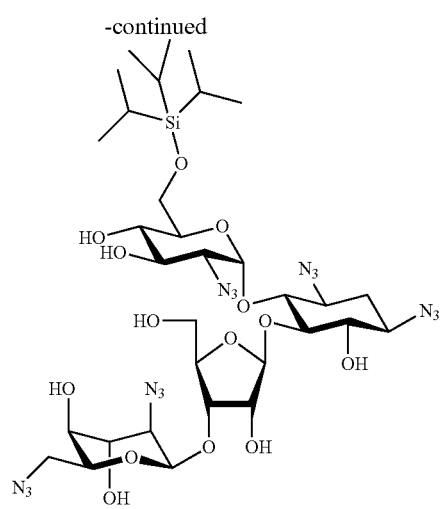

To an oven dried 50.0 mL bottom flask equipped with magnetic stirrer was added per-azidoparomomycin from the above reaction (2.63 g, 3.5 mmol), 4-DMAP (1.25 g, 10.2 mmol) and anhydrous DMF (28.0 mL). The resulting clear solution was cooled to 0° C. in ice-bath while stirring under nitrogen. Triisopropylsilylchloride (0.89 mL, 42.3 mmol) was added dropwise to the stirred reaction mixture via syringe. The reaction was continued stirred for two hours maintaining the temperature at 0° C. The reaction mixture was then partitioned between ethyl acetate and 10% aqueous $NaHCO_3$ solution. The organic layer was separated and washed with saturated brine solution and dried over $Na_2SO_4$, filtered and evaporated to dryness to afforded clear oil. The product was obtained after purification by flash chromatography (1.57 g, 50% yield) using gradients of $CHCl_3$/MeOH (97:3).

$^1$H NMR (300 MHz, DMSO) δ 1.36 (q, J=12 Hz, 1H), δ 1.90-1.22 (m, 21H) δ 2.06-2.10 (m, 1H) δ 2.97-3.03 (m, 7H), δ 3.08-3.98 (m, 13H), δ 4.15 (s, 2H), δ 4.6 (t, J=60.4 Hz, 1H), δ 4.94 (d, J=5.0 Hz, 1H), δ 4.99-5.03 (m, 1H), δ 5.14 (d, J=3.73 Hz, 1H), δ 5.20 (d, J=4.6 Hz, 1H), δ 5.27 (s, 1H), δ 5.44 (d, J=5.5 Hz, 1H), δ 5.59 (d, J=3.90 Hz, 1H), δ 5.68 (d, J=6.2 1H), δ 5.79 (d, J=3.73 Hz. 1H), δ 6.62 (dd, J=5.09, 1.5 Hz, 2H), δ 8.10 (d, J=6.56 Hz, 1H); $^{13}$C NMR δ 154.19, 148.11, 108.18, 106.63, 97.56, 95.38, 83.08, 81.62, 75.87, 75.52, 74.00, 73.79, 73.10, 72.76, 70.41, 70.26, 69.76, 66.96, 63.31, 62.91, 62.20, 59.79, 59.58, 59.15, 50.77, 38.64, 31.72, 17.81, 17.79, 11.37, 0.00 LCMS m/z 924 (M+Na), (>99% purity).

Example 15

Benzyl Protection of Hydroxyl Groups

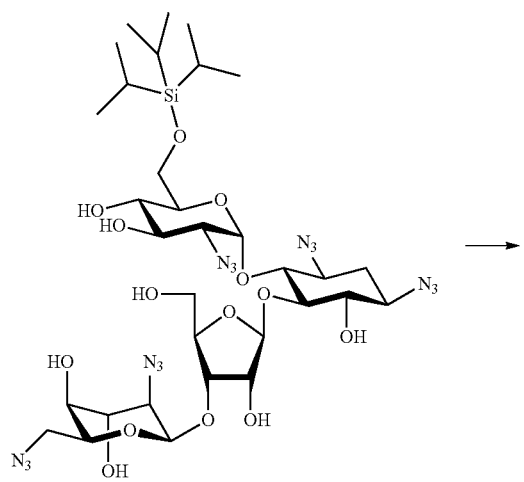

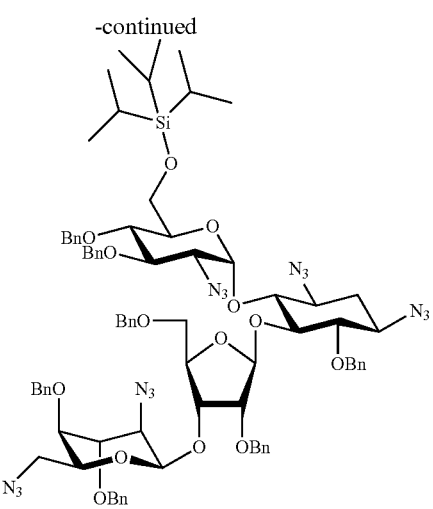

To a 50.0 mL bottom flask equipped with magnetic stirrer was added the tips protected compound from the previous example (3.77 g, 4.18 mmol) dissolved in anhydrous DMF (20.0 mL). The resulting clear solution was cooled to 0° C. in ice-bath while stirring under nitrogen. 60% NaH (2.34 g, 58.5 mmol) was then added slowly and stirred for 20 minutes. BnBr (4.97 mL, 41.87 mmol) was added dropwise to the stirred reaction mixture via syringe. Temperature of 0° C. was maintained for 1 h followed by 3h at room temperature. The reaction was then cooled at 0° C. and quenched with saturated $NaHCO_3$ solution (2.0 mL) dropwise. The reaction mixture was then partitioned between DCM and 10% aqueous $NaHCO_3$ solution. The organic layer was separated and washed with saturated brine solution and dried over $Na_2SO_4$, filter and evaporated to dryness to afforded clear oil which was purified by silica gel chromatography using gradients of Hexane/EtOA (9:1) to afford the title compound (6.02 g, 93% yield) which was used as is in the next step.

Example 16

Selective Deprotection of the 6'-Position of Perbenzylated 6'-O-Tips-Perazido-Paromomycin and Oxidation to the Aldehyde -continued

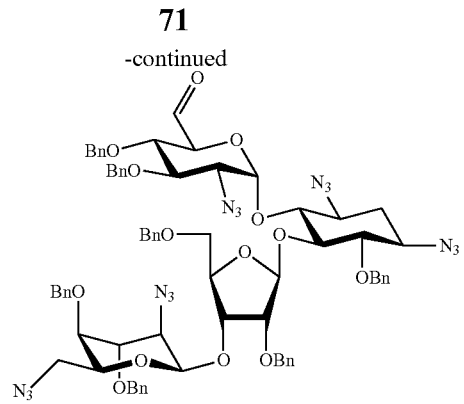

-continued

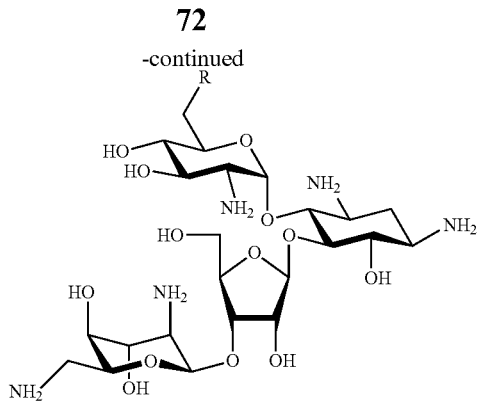

To a 50.0 mL bottom flask equipped with magnetic stirrer was added the benzyl protected 6'-O-Tips-perazidoparomomycin (6.0 g, 3.92 mmol) dissolved in anhydrous THF (20 mL). The resulting clear solution was cooled to 0° C. in ice-bath while stirring under nitrogen. 1.0M TBAF•THF (8.63 mL, 7.84 mmol) was added dropwise to the stirred reaction mixture via syringe and the reaction was then allowed to proceed at room temperature. The reaction was quenched with saturated $NH_4CO_3$ solution (30.0 mL), extracted with EtOAc and evaporated to dryness to afforded the product as a yellow oil which could be purified by silica gel chromatography using gradients of Hexane/EtOA (8:2) to afforded the title compound (5.4 g, 83% yield) as a white foam. This product (470 mg) was treated with IBX in DMSO (1.2 mL) and THF (1.0 mL) at room temperature for 2.5 hours. At that time, DCM (15 mL) and $H_2O$ (10 mL) were added and the aqueous layer was separated and extracted twice more (15 mL). The combined organic layers were dried ($Na_2SO_4$), filtered and evaporated to give crude product which could be purified by silica gel chromatography using gradients of Hexane/EtOA (7:3) to afford the title compound (409 mg, 50% yield).

General Procedure for Reductive Amination and Deprotection

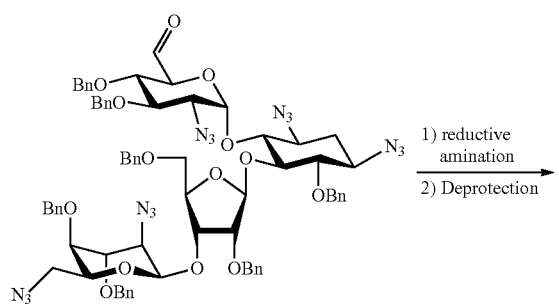

The crude aldehyde (36:moles) was dissolved in dry MeOH (2 mL) and dry THF (1 mL). To this solution was added the appropriate amine (5 equivalents) in MeOH (2 mL) with the pH adjusted to 5 with AcOH. $NaCNBH_3$ (4 equivalents) was then added and the mixture was allowed to stir for 16 hours, at which time the reaction was quenched with $NaHCO_3$. The reaction was evaporated to dryness, and then the crude mixture was partitioned between DCM and 10% aqueous $NaHCO_3$ solution. The organic layer was separated and washed with saturated brine solution and dried over $Na_2SO_4$, filter and evaporated to dryness to affored clear oil which was purified by silica gel chromatography using gradients of DCM:MeOH (96:4) to afford the protected amine, which was used as is in the next step. To the protected amine was added 2 mL of EtOH, Raney nickel (25-50 mg) and hydrazine (7-14 equivalents). After the reaction had gone to completion as determined by LCMS, the reaction was filtered and evaporated to give the crude perbenzylated product. This was treated with hydrogen (1 atm), palladium (II) hydroxide (2.5 mg) in AcOH (1 mL) and THF (1 mL) to give, after 24 hours, the title compound 15 after lyophilization.

Example 18

Preparation of Compound 15a

Using 4M dimethylamine in methanol in the general procedure above gave the title compound. LCMS m/z 643 (M+H), (>95% purity). $^1$H NMR was consistent with the structure.

R=$N(CH_3)_2$, see Example 17.

Example 19

Preparation of Compound 15b

Using 1,3-diaminopropane in the general procedure above gave the title compound. LCMS m/z 672 (M+H), (>95% purity). $^1$H NMR was consistent with the structure.

R=$N(H)(CH_2)_3NH_2$ see Example 17.

Example 20

Preparation of Compound 15c

Using morpholine in the general procedure above gave the title compound. LCMS m/z 685 (M+H), (>95% purity). $^1$H NMR was consistent with the structure.

R=

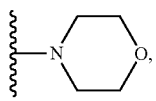

see Example 17.

Example 21

Preparation of Compound 15d

Using N-Boc-hydrazine in the general procedure above gave the title compound. LCMS m/z 730 (M+H), (>95% purity). $^1$H NMR was consistent with the structure.

R=N(H)N(H)—BOC, see Example 17.

Example 22

Preparation of Compound 15e

Using 2.0 M methylamine in methanol in the general procedure above gave the title compound. LCMS m/z 629 (M+H), (>95% purity). $^1$H NMR was consistent with the structure.

R=N(H)CH$_3$, see Example 17.

Example 23

Preparation of Compound 15f

Using 1,4-diaminobutane in the general procedure above gave the title compound. LCMS m/z 686 (M+H), (>95% purity). $^1$H NMR was consistent with the structure.

R=N(H)(CH$_2$)$_4$NH$_2$ see Example 17.

Example 24

Preparation of Compound 15g

Using p-Methylphenethylamine in the general procedure above gave the title compound. LCMS m/z 733 (M+H), (>95% purity). $^1$H NMR was consistent with the structure.

R=

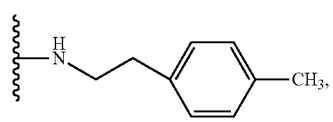

see Example 17.

Example 25

Preparation of Compound 15h

Using isopropylamine in the general procedure above gave the title compound. LCMS m/z 657 (M+H), (>95% purity). $^1$H NMR was consistent with the structure.

R=N(H)C(H)(CH$_3$)$_2$, see Example 17.

Example 26

Preparation of Compound 15i

Using hydrazine in the general procedure above gave the title compound. This compound can also be prepared from the protected hydrazinyl compound of Example 21. LCMS m/z 630 (M+H), (>95% purity). $^1$H NMR was consistent with the structure.

R=N(H)NH$_2$, see Example 17.

Example 27

Preparation of Compound 15j

Using phenethylamine in the general procedure above gave the title compound. LCMS m/z 719 (M+H), (>95% purity). $^1$H NMR was consistent with the structure.

R=N(H)(CH$_2$)$_2$Ph, see Example 17.

Example 28

Preparation of Compound 15k

Using N-methyl-phenethylamine in the general procedure above gave the title compound. LCMS m/z 733 (M+H), (>95% purity). $^1$H NMR was consistent with the structure.

R=N(CH$_3$)(CH$_2$)$_2$Ph, see Example 17.

Example 29

Preparation of Compound 15l

Using phenpropylamine in the general procedure above gave the title compound. LCMS m/z 733 (M+H), (>95% purity). $^1$H NMR was consistent with the structure.

R=N(H)(CH$_2$)$_3$Ph, see Example 17.

Example 30

Preparation of Compound 15m

Using p-cyclohexenyl phenethylamine in the general procedure above gave the title compound. LCMS m/z 801 (M+H), (>95% purity). $^1$H NMR was consistent with the structure.

R=

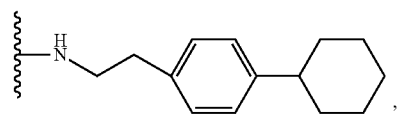 [SMILES: *NCCc1ccc(C2CCCCC2)cc1]

see Example 17.

Example 31

Preparation of Compound 15n

Using o-methoxyphenethylamine in the general procedure above gave the title compound. LCMS m/z 749 (M+H), (>95% purity). $^1$H NMR was consistent with the

R=

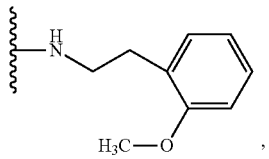

see Example 17.

Example 32

Preparation of Compound 15o

Using p-fluorophenethylamine in the general procedure above gave the title compound. LCMS m/z 737 (M+H), (>95% purity). $^1$H NMR was consistent with the structure.

R=

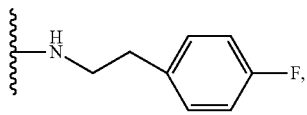 [SMILES: *NCCc1ccc(F)cc1]

see Example 17.

Example 33

Preparation of Compound 15p

Using β-methylphenethylamine in the general procedure above gave the title compound. LCMS m/z 733 (M+H), (>95% purity). $^1$H NMR was consistent with the structure.

R=N(H)C(H)(CH$_3$)CH$_2$Ph, see Example 17.

Example 34

Preparation of Compound 15q

Using p-(trifluoromethyl)phenethylamine in the general procedure above gave the title compound. LCMS m/z 787 (M+H), (>95% purity). $^1$H NMR was consistent with

R=

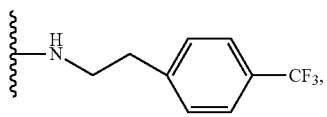 [SMILES: *NCCc1ccc(C(F)(F)F)cc1]

see Example 17.

Example 35

Preparation of Compound 15r

Using p-methoxyphenethylamine in the general procedure above gave the title compound. LCMS m/z 749 (M+H), (>95% purity). $^1$H NMR was consistent with the structure.

R=

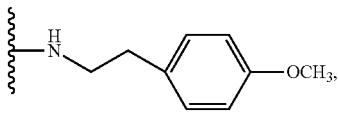 [SMILES: *NCCc1ccc(OC)cc1]

see Example 17.

Example 36

Preparation of Compound 15s

Using indoline in the general procedure above gave the title compound. LCMS m/z 723 (M+H), (>95% purity). $^1$H NMR was consistent with the structure.

R=

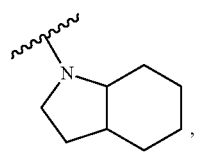 [SMILES: *N1CCC2CCCCC21]

see Example 17.

Example 37

Preparation of Compound 15t

Using β-hydroxy-N-methylphenethylamine in the general procedure above gave the title compound. LCMS m/z 749 (M+H), (>95% purity). $^1$H NMR was consistent with the structure.

R=N(CH$_3$)C(H)(OH)(CH$_2$)Ph, see Example 17.

Example 38

Preparation of Compound 15u

Using m-(trifluoromethyl)phenethylamine in the general procedure above gave the title compound. LCMS m/z 787 (M+H), (>95% purity). $^1$H NMR was consistent with the structure.

R=

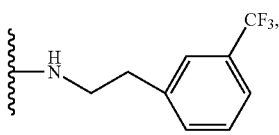 [SMILES: *NCCc1cccc(C(F)(F)F)c1]

see Example 17.

Example 39

Preparation of Compound 15v

Using m-methoxyphenethylamine in the general procedure above gave the title compound. LCMS m/z 749 (M+H), (>95% purity). $^1$H NMR was consistent with the structure.

R=

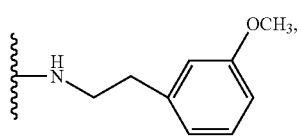 [SMILES: *NCCc1cccc(OC)c1]

see Example 17.

Example 40

Preparation of Compound 15w

Using tryptamine in the general procedure above gave the title compound. LCMS m/z 766 (M+H), (>95% purity). ¹H NMR was consistent with the structure.

R=

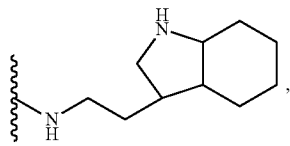 [SMILES: *NCCC1CNC2CCCCC12]

see Example 17.

Example 41

Preparation of Compound 15x

Using 1-napthylethylamine in the general procedure above gave the title compound. LCMS m/z 773 (M+H), (>95% purity). ¹H NMR was consistent with the

R=

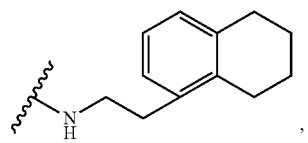 [SMILES: *NCCc1cccc2c1CCCC2]

see Example 17.

Example 42

Preparation of Compound 15y

Using 4-(aminoethyl)pyridine in the general procedure above gave the title compound. LCMS m/z 726 (M+H), (>95% purity). ¹H NMR was consistent with the structure.

R=

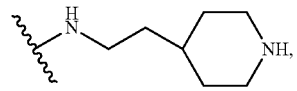 [SMILES: *NCCC1CCNCC1]

see Example 17.

Example 43

Preparation of Compound 15z

Using 3-(aminoethyl)pyridine in the general procedure above gave the title compound. LCMS m/z 726 (M+H), (>95% purity). ¹H NMR was consistent with the structure.

R=

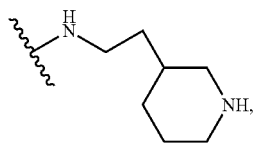 [SMILES: *NCCC1CCCNC1]

see Example 17.

Example 44

Preparation of Compound 15aa

Using 2-(aminoethyl)pyridine in the general procedure above gave the title compound. LCMS m/z 726 (M+H), (>95% purity). ¹H NMR was consistent with the

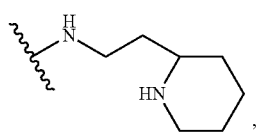

see Example 17.

Example 45

Synthesis of Compound 16

Synthesis of Compound 16a

2 ⟶

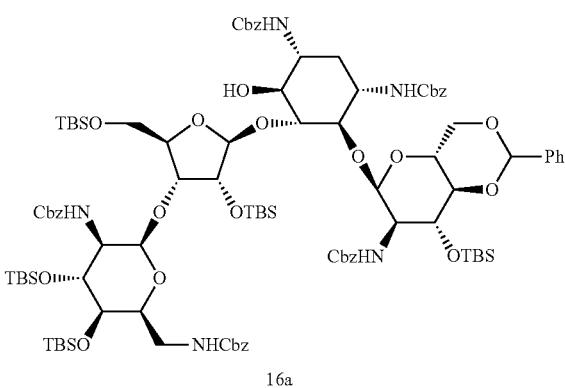

16a

To a stirred solution of Compound 2 (1.35 g, 0.98 mmol) in dry dichloromethane (20 mL) was added 2,4,6-collidine (1.07 g, 8.82 mmol) and TBDMSOTf (1.811 g, 6.86 mmol) at 0° C. The reaction mixture was slowly brought to room temperature and stirred for 12 hours. A few drops of water was added to quench the excess TBSOTf, followed by extraction with dichloromethane. The organic layer was washed with brine and dried over anhydrous $Na_2SO_4$, followed by concentration of the solvent to give the corresponding crude product. The crude product was purified by flash column chromatography to give Compound 16a (1.048 g, 55%).

$[\alpha]_D$=+16° (c 0.6, $CHCl_3$). ESI/MS calcd for $C_{100}H_{149}N_5O_{24}Si_5$ (M+H$^+$) 1944.94. found 1946.

Synthesis of Compound 16b

16a ⟶

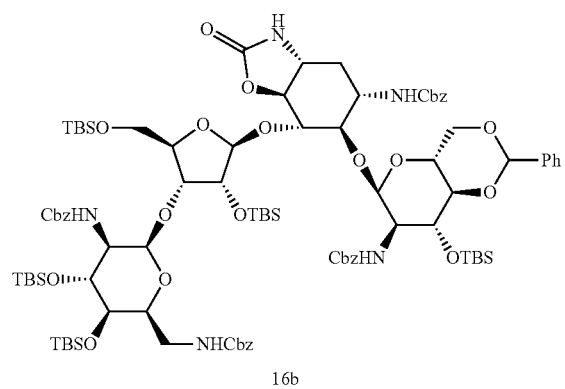

16b

To a stirred solution of Compound 16a (330 mg, 0.17 mmol) in dry DMF (6 mL) was added 60% NaH in mineral oil (8 mg) at 0° C. with stirring continued for an additional 6 hours at 0° C. A few drops of saturated ammonium chloride solution were added, followed by extraction with ethyl acetate. The organic layer was washed with brine and dried over anhydrous $Na_2SO_4$, followed by concentration of the solvent yielded the corresponding crude product. The crude product was purified by flash column chromatography to yield the Compound 16b (180 mg, 58%) and 120 mg (36%) of Compound 16a was also recovered.

$[\alpha]_D$=+18° (c 0.5, $CHCl_3$). ESI/MS calcd for $C_{93}H_{141}N_5O_{23}Si_5$ (M+H$^+$) 1836.89. found 1837.6

Synthesis of 4',6'-O-benzylidene-penta-O-tert-butyldimethylsilanyloxy-tetra-N-benzyloxycarbonyl paromomycin (16c)

16b ⟶

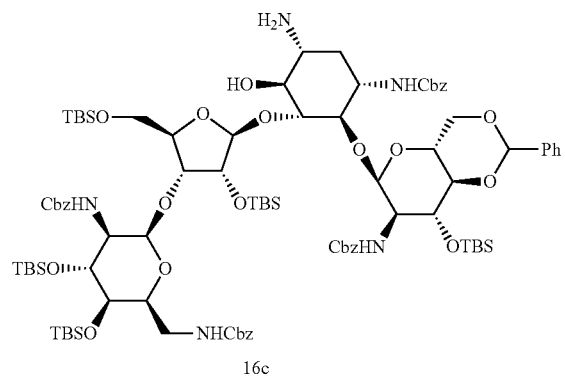

16c

To a stirred solution of Compound 16b (190 mg, 0.1 mmol) in DMF (7 mL) was added 0.7 mL of aqueous LiOH (9 mg, 0.21 mmol) with stirring continued for an additional 3 hours at room temperature. A few drops of saturated ammonium chloride solution was added, followed by extraction with ethyl acetate. The organic layer was washed with brine and dried over anhydrous $Na_2SO_4$, followed by concentration of the solvent yielded the corresponding crude product. The crude product was purified by flash column chromatography to Compound 16c (100 mg, 53%) and 50 mg (26%) of Compound 16b was also recovered.

$[\alpha]_D$=+13° (c 0.3, $CHCl_3$), ESI/MS calcd for $C_{92}H_{143}N_5O_{22}Si_5$ (M+H$^+$) 1810.91. found 1811.3.

Synthesis of 4',6'-O-Benzylidene-penta-O-tert-butyldimethylsilanyloxy-tetra-N-benzyloxycarbonyl-N-1-haba paromomycin (16d)

16c ⟶

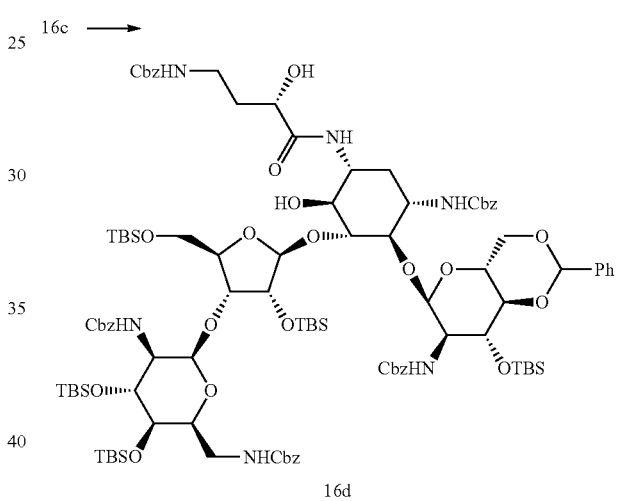

16d

To a stirred solution of benzyloxy 4-hydroxy aminobutric acid (27 mg, 0.11 mmol), N-Hydroxy succinimide (12 mg, 0.11 mmol) in dry THF (2 mL) was added DCC (22 mg, 0.11 mmol) with stirring continued for an additional 1 hour at room temperature. To this reaction mixture the free amine, Compound 16c (95 mg, 0.053 mmol) in dry THF (2 mL) and triethyl amine (15 µL, 0.11 mmol) was added with stirring for 12 hours at room temperature. Evaporation of the solvent followed by purification by flash column chromatography gave Compound 16d (80 mg, 74%).

$[\alpha]_D$=+19° (c 0.4, $CHCl_3$).

Synthesis of 4',6'-O-benzylidene-tetra-N-benzyloxycarbonyl-N-1-haba paromomycin (16e)

16d ⟶

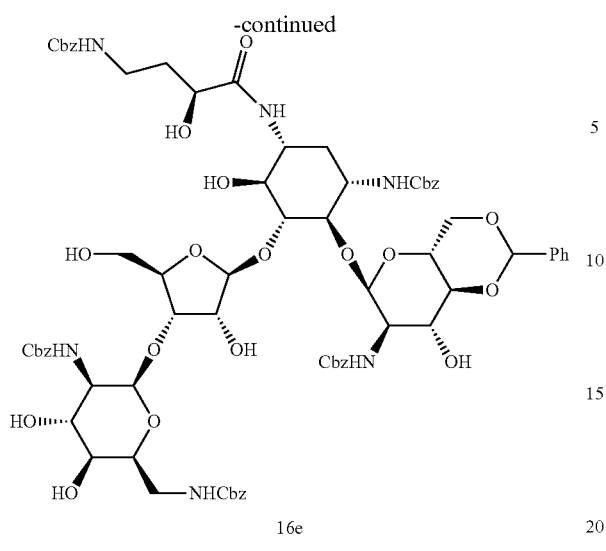

16e

Compound 16d (90 mg, 0.044 mmol) was dissolved in dry pyridine (2 mL), HF.Py (2 mL) was added at 0° C., the reaction was slowly brought to room temperature and stirred for 2 days. Water was added and the reaction mixture was extracted with ethyl acetate followed by washing with brine. The organic layer was dried over $Na_2SO_4$ and evaporated to give the crude product. The crude product was purified by column chromatography to give Compound 16e (50 mg, 77%).

$[\alpha]_D$=+20° (c 0.6, $CHCl_3$). ESI/MS calcd for $C_{74}H_{86}N_6O_{26}$ (M+H$^+$); 1475.56. found 1475.7.

Synthesis of Compound 16

16e →

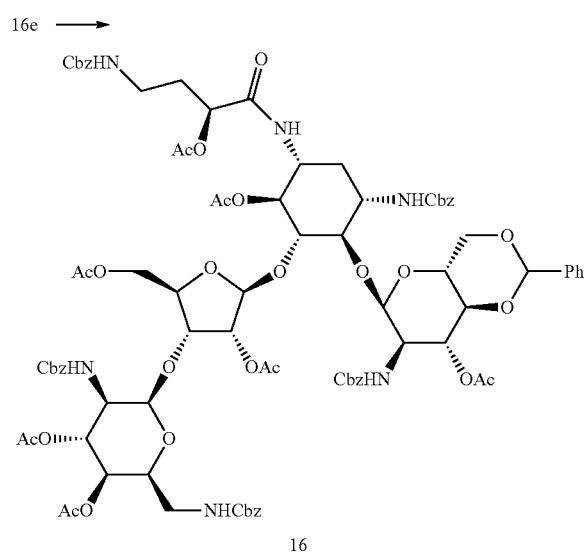

16

To a solution of Compound 16e (270 mg, 0.183 mmol) in pyridine (2 mL) was added acetic anhydride (1 mL) with stirring maintained for 24 hours at room temperature. Water (10 mL) was added and the precipitated product was filtered. The aqueous layer was extracted with ethyl acetate, washed with saturated $CuSO_4$, brine and the organic layer was dried over anhydrous $Na_2SO_4$. The organic layer was combined with the precipitated product and evaporated to provide the crude material, which yielded Compound 16 (300 mg, 93%) after column chromatography.

$[\alpha]_D$=+7.5° (c 0.2, $CHCl_3$). ESI/MS calcd for (M+H$^+$) 1768.63. found 1769.8.

Example 46

Synthesis of Compound 17

16 →

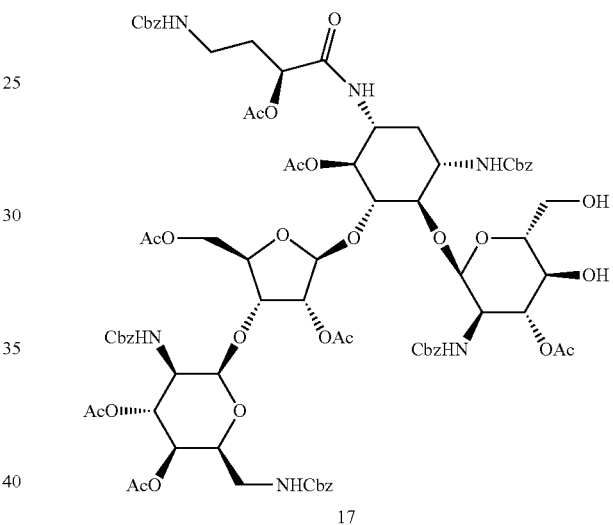

17

Compound 16 (300 mg, 0.17 mmol) was stirred in 20 mL of acetic acid/water mixture (4:1) at room temperature for 4 days. Water was added and the precipitated product was filtered. The aqueous layer was extracted with ethyl acetate, washed with water, brine and the organic layer was dried over anhydrous $Na_2SO_4$. The organic layer was combined with the precipitated product and evaporated to yield the crude material, which yielded Compound 17 (280 mg, 98%) after column chromatography.

$[\alpha]_D$=+10.7° (c 0.3, $CHCl_3$). HRMS calcd for (M+H$^+$) 1681.60911. found 1681.60830.

Example 47

Synthesis of Compound 18

17 →

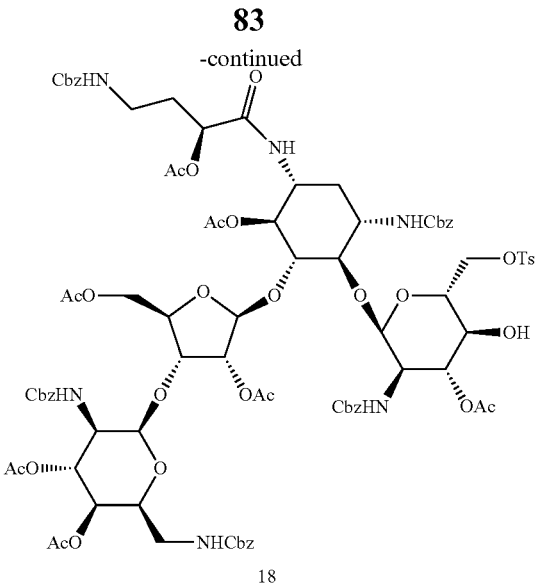

18

To a solution of Compound 17 (290 mg, 0.17 mmol) in pyridine (2 mL) was added TsCl (36 mg, 0.19 mmol), DMAP (5 mg, 0.041 mmol) with stirring maintained for 12 hours at room temperature. An additional 1.1 equivalent of TsCl (36 mg, 0.19 mmol) was added and the reaction was stirred for additional 8 hours at room temperature. Water was added and the precipitated product was filtered. The aqueous layer was extracted with ethyl acetate, washed with water, brine and the organic layer was dried over anhydrous $Na_2SO_4$. The organic layer was combined with the precipitated product and evaporated to yield the crude material. Compound 18 (300 mg, 96%) was obtained after column chromatography.

$[\alpha]_D$=+14.8° (c 0.25, $CHCl_3$). HRMS calcd for $C_{88}H_{102}N_6O_{35}S$ (M+H$^+$) 1835.61796. found 1835.61976.

Example 48

Synthesis of Compound 19

18 ⟶

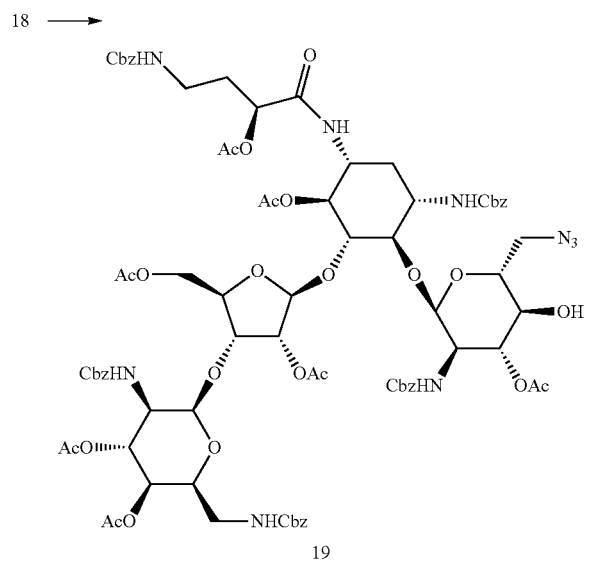

19

To a solution of Compound 18 (320 mg, 0.175 mmol) in dry DMF (3 mL) was added $NaN_3$ (113 mg, 1.74 mmol) with stirring maintained for 24 hours 70° C. Water was added and the resulting mixture was extracted with ethyl acetate followed by washing with water and then brine. The organic layer was dried over anhydrous $Na_2SO_4$ and evaporated under reduced pressure. Compound 19 (252 mg, 84%) was obtained following column chromatography.

$[\alpha]_D$=+11.3° (c 0.3, $CHCl_3$). ESI/MS calcd for $C_{81}H_{95}N_9O_{32}$ (M+H$^+$) 1705.61. found 1707.0.

Example 49

Synthesis of Compound 20

19 ⟶

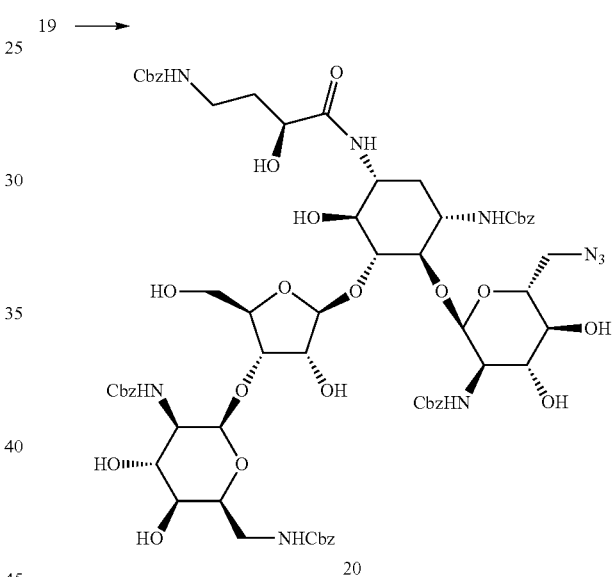

20

Very small piece of sodium was added into methanol (10 mL) and pH was adjusted to 10. This solution was transferred to Compound 19 in methanol (1 mL) and stirred overnight (12 hours). Dry ice was added to quench the reaction followed by evaporation of the methanol. The resultant crude material was purified by column chromatography to yield Compound 20 (52 mg, 66%).

$[\alpha]_C$=+16° (c 0.15, $CHCl_3$). HRMS calcd for $C_{67}H_{81}N_9O_{25}$ (M+H$^+$) 1412.54164. found 1412.53764.

Example 50

Synthesis of Compound 21

20 ⟶

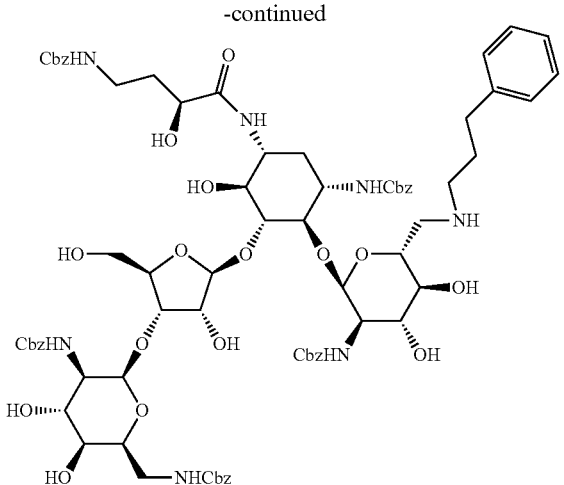

21

To a solution of Compound 20 (30 mg, 0.021 mmol) in dry THF (3 mL) was added 1M PMe₃ in THF (26 µL, 0.026 mmol) with stirring maintained for 1 hour at room temperature. Water (0.2 mL) was added and stirring was continued for an additional hour. Another 26 µL of PMe₃ (1M in THF) was added and stirred for 12 hours. Evaporation of the reaction mixture followed dissolving in ethyl acetate and washing with water gave the crude product which was pure enough to use in the next step. To this crude amine in dry methanol was added phenylproyl aldehyde (3 mg, 0.022 mmol) and a drop of glacial acetic acid with stirring for 5 minutes followed by addition of 1M NaBH₃CN in THF (42 µL, 0.042 mmol) with stirring for 12 hours at room temperature. Evaporation of the solvent followed by column purification gave Compound 21 (12 mg, 38%, 2 steps).

$[\alpha]_C$=+16.7° (c 0.15, CHCl₃). ESI/MS calcd for $C_{76}H_{93}N_7O_{25}$ (M+H⁺) 1503.62. found 1504.7.

Example 51

Synthesis of Compound 22
(N-1-haba-6'-phenylpropyl neomycin)

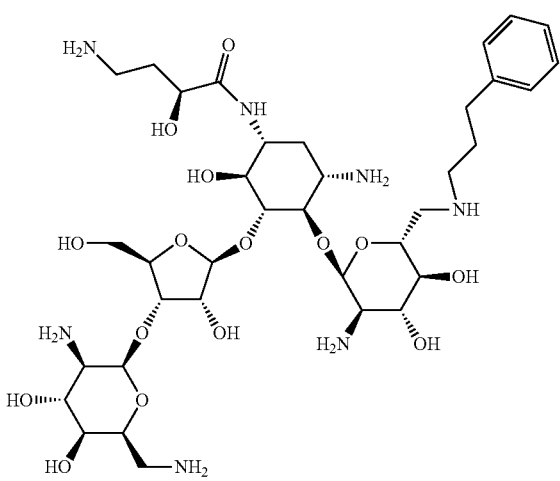

22

To a solution of Compound 21 (11 mg, 0.0073 mmol) in 2 mL of acetic acid/water mixture (4:1) and 0.5 mL of methanol was added 20% Pd(OH)₂ (22 mg) at room temperature with stirring for 6 hours under an atmosphere of hydrogen(balloon). The material was filtered over celite and lypholized to give Compound 22 as the acetic acid salt (8 mg, 99%).

$[\alpha]_D$=+39.2° (c 0.12, H₂O). NMR (400 MHz, D₂O) δ 7.28-7.17 (m, 5H), 5.89 (d, J=3.7 Hz, 1H), 5.29 (s, 1H), 5.16 (s, 1H), 4.45-4.37 (m, 1H), 4.32-4.25 (m, 1H), 4.25-4.15 (m, 2H), 4.1 (br s, 2H), 3.95-3.72 (m, 6H), 3.7-3.45 (m, 4H), 3.4-3.2 (m, 6H), 3.19-3.1 (m, 1H), 3.01-2.94 (m, 4H), 2.6 (t, J=7.4 Hz, 2H), 2.15-1.8 (m, 6H). ¹³C NMR (125 MHz, D₂O) δ 175.2, 140.2, 128.4, 128.0, 126.1, 109.9, 95.1, 94.9, 85.3, 80.8, 75.4, 74.6, 73.3, 73.2, 70.5, 69.6, 69.1, 68.8, 67.5, 67.2, 66.9, 59.4, 53.0, 50.4, 48.4, 48.2, 47.8, 47.7, 40.0, 36.2, 31.4, 30.4, 29.5, 26.5. HRMS calcd for $C_{36}H_{63}N_7O_{15}$ (M+H⁺) 834.44549. found 834.44463.

Example 52

Synthesis of Compound 23

20 →

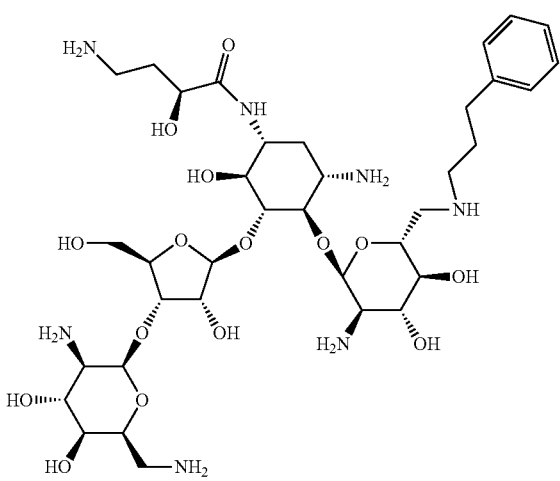

23

To a solution of Compound 20 (18 mg, 0.0127 mmol) in 2 mL of acetic acid/water mixture (4:1) and 0.2 mL of methanol was added 20% Pd(OH)₂ (18 mg) at room temperature with stirring maintained for 2 hours under an atmosphere of hydrogen (balloon). The material was filtered over celite and lypholized to give Compound 23 as the acetic acid salt (13 mg, 95%).

$[\alpha]_D$=+27.4° (c 0.23, H₂O). ¹H NMR (400 MHz, D₂O) δ 5.89 (s, 1H), 5.28 (s, 1H), 5.15 (s, 1H), 4.38 (br s, 1H), 4.27 (br s, 1H), 4.17 (br s, 2H), 4.1 (br s, 2H), 3.9-3.75 (m, 6H), 3.69-3.62 (m, 2H), 3.5-3.4 (m, 2H), 3.4-3.2 (m, 6H), 3.8-3.1 (m, 1H), 3.0 (br s, 2H), 2.18-1.98 (m, 2H), 1.7-1.6 (m, 2H). ¹³C NMR (125 MHz, D₂O) δ 175.2, 109.9, 95.1, 94.9, 85.2, 80.8, 75.5, 74.6, 73.3, 73.1, 70.3, 69.7, 69.0, 68.9, 67.6, 67.2, 66.9, 59.4, 53.1, 50.4, 48.4, 48.2, 40.0, 39.7, 36.2, 30.4, 29.5. HRMS calcd for $C_{27}H_{53}N_7O_{15}$ (M+H⁺) 716.367; 24 found 716.36662.

Example 53

Synthesis of N-1-aloc-4',6'-O-benzylidene-penta-O-tert-butyldimethylsilanyloxy-penta-N-benzyloxycarbonyl paromomycin (25)

16c ⟶

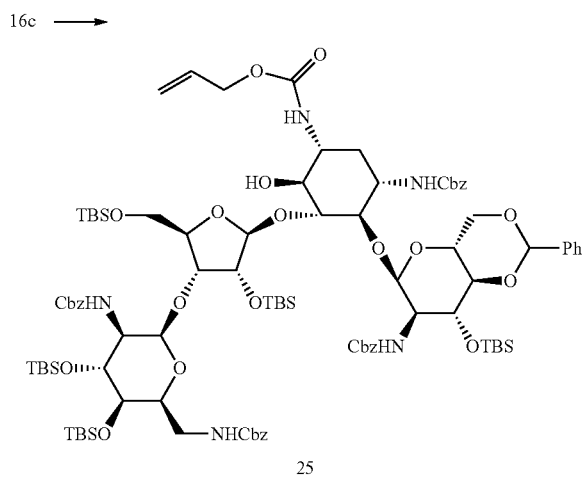

25

To a stirred solution of Compound 16c (Example 45, 1.125 g, 0.62 mmol) in dry dichloromethane (20 mL) was added Et$_3$N (0.11 mL, 1.24 mmol) and aloc-Cl (83 μL, 0.78 mmol) at 0° C. The reaction mixture was slowly brought to room temperature and stirred for 6 hours. Evaporation of the solvent followed by purification by flash column chromatography yielded Compound 25 (600 mg, 51%).

$[\alpha]_D$=+5.25° (c 0.4, CHCl$_3$). ESI/MS calcd for C$_{96}$H$_{147}$N$_5$O$_{24}$Si$_5$ (M+H$^+$) 1894.93. found 1895.3.

Example 54

Synthesis of N-1-aloc-6-O-allyl-4',6'-O-benzylidene-penta-O-tert-butyldimethylsilanyloxy-penta-N-benzyloxycarbonyl paromomycin (26)

25 ⟶

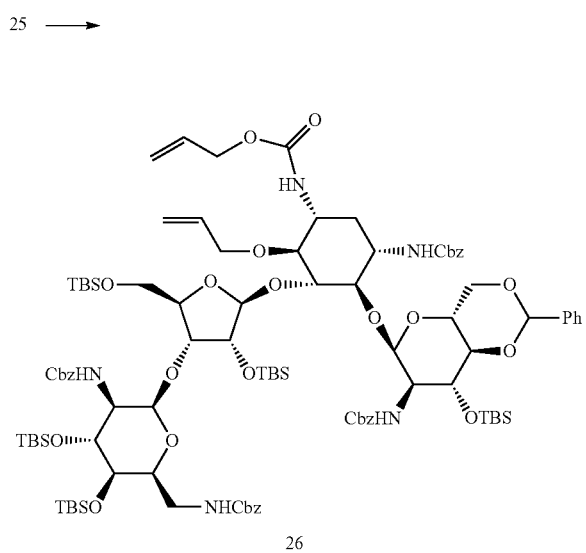

26

To a stirred solution of Compound 25 (558 mg, 0.3 mmol) in dry THF (15 mL) were added 0.5M KHMDS in toluene (0.66 mL, 0.33 mmol) and allyl iodide (0.11 mL, 1.2 mmol) at 0° C. The reaction mixture was slowly brought to room temperature and stirred for 12 hours. The reaction mixture was quenched with saturated NH$_4$Cl solution followed by extraction with ethyl acetate. The organic layer was washed with brine and dried over anhydrous Na$_2$SO$_4$ and evaporated under reduced pressure to give the crude product. The crude material was purified by flash column chromatography to yield Compound 26 (480 mg, 83%).

$[\alpha]_D$=+10.1 (c 0.6, CHCl$_3$).

Example 55

Synthesis of 6-O-allyl-4',6'-O-benzylidene-penta-O-tert-butyldimethylsilanyloxy-N-1-haba-penta-N-benzyloxycarbonyl paromomycin (27)

26 ⟶

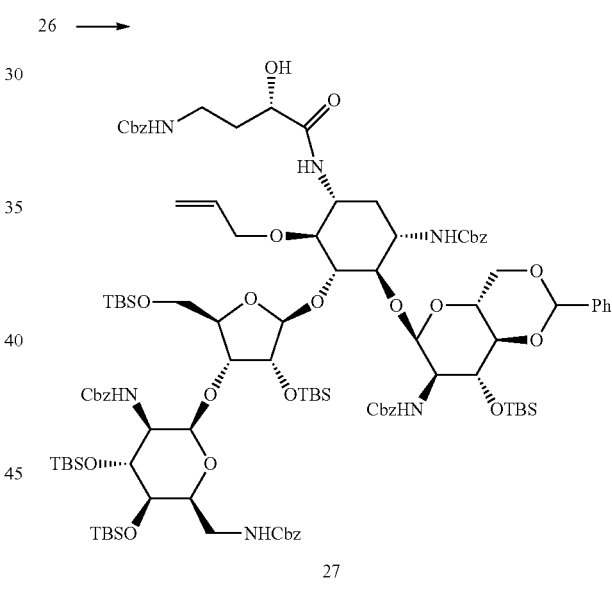

27

To a solution of Compound 26 (1.125 g, 0.62 mmol) and morpholine in dry THF (20 mL) was added Pd(PPh$_3$)$_4$ (29 mg, 0.025 mmol) at room temperature with stirring for 3 hours. Evaporation of the solvent yielded the crude free amine and this was used in the next step without purification.

To a solution of benzyloxy 4-hydroxy aminobutric acid (253 mg, 1 mmol), N-hydroxy succinimide (115 mg, 1 mmol) in dry THF (2 mL) was added DCC (201 mg, 1 mmol) with stirring maintained for 2 hours at room temperature. To this reaction mixture the crude free amine (from above) in dry THF (2 mL) and triethyl amine (0.11 mL, 0.76 mmol) was added with stirring for 12 hours at room temperature. Evaporation of the solvent followed by purification by flash column chromatography yielded Compound 27 (160 mg, 31%).

$[\alpha]_D$=+11.0° (c 0.1, CHCl$_3$).

Example 56

Synthesis of 4',6'O-benzylidene-N-1-haba-6-O-phenylethylaminoethyl-penta-N-benzloxycarbonyl paromomycin (28a)

27 ⟶

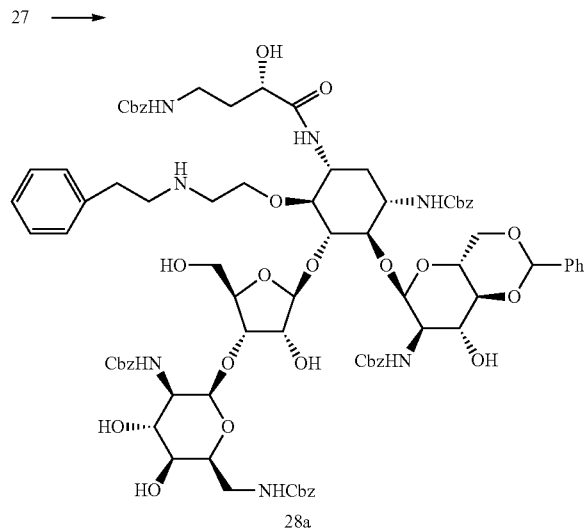

28a

Ozone gas was passed through a stirred solution of Compound 27 (78 mg, 0.037 mmol) in dry dichloromethane (3 mL) at −78° C. for 2 hours. Ozone was degassed by passing nitrogen gas for 10 minutes followed by the addition of excess dimethyl sulfide (0.2 mL). This solution was stirred for 2 hours at room temperature. The solvent was reduced under reduced pressure and the remaining mixture was extracted with ethyl acetate. The organic layer was washed with $NaHCO_3$, brine and dried over anhydrous $Na_2SO_4$. Evaporation of the solvent gave the crude material (75 mg). This material was dissolved in McOH. To this reaction mixture phenylethyl amine (10 mg, 0.083 mmol) and one drop of AcOH were added and stirred for 5 minutes. Then $NaBH_3CN$ (5 mg, 0.08 μmol) was added and stirred for 12 hours at room temperature. Evaporation of the solvent followed gave the crude product (58 mg). This material was dissolved in dry pyridine (1 mL) followed by the addition of HF.Py (1 mL) at 0° C. The reaction was slowly brought to room temperature and stirred for 2 days. Water was added to the reaction mixture followed by extraction with ethyl acetate. The organic layer was washed with brine and dried over $Na_2SO_4$. Evaporation of the solvent gave the crude material and this crude product was purified by column chromatography to give Compound 28a (23 mg, 38%, 3 steps).

$[\alpha]_D$=+15.8° (c 0.3, $CHCl_3$). ESI/MS calcd for $C_{84}H_{99}N_7O_{26}$ (M+H$^+$) 1622.66. found 1623.1.

Example 57

Synthesis of N-1-haba-6-O-phenylethylaminoethyl-paromomycin (29a)

28a ⟶

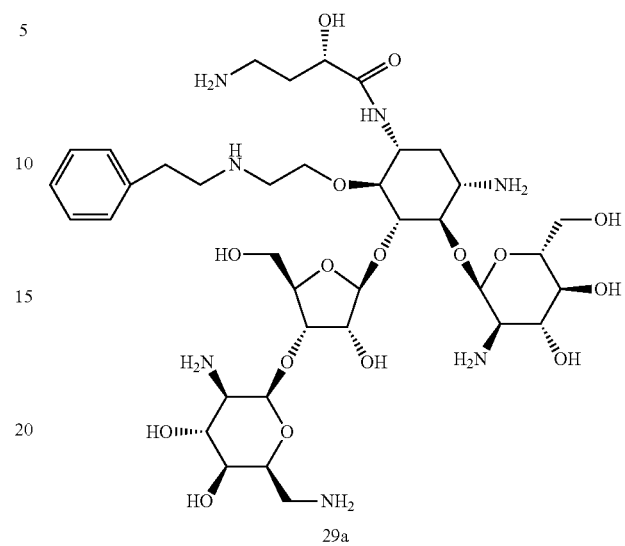

29a

Compound 28a (22 mg, 0.014 mmol) in 2 mL of acetic acid/water mixture (4:1) was stirred at room temperature for 12 hours and then for an additional 6 hours at 55° C. To this reaction mixture 20% $Pd(OH)_2$ (22 mg) was added and stirred under an atmosphere of hydrogen (balloon) for 3 hours. The mixture was filtered over celite and lypholized to give the pure acetate salt of Compound 29a (14 mg, 81%).

$[\alpha]_D$=+40.33° (c 0.25, $H_2O$). $^1$H NMR (400 MHz, $D_2O$) δ 7.29-7.20 (m, 5H), 5.65 (d, J=3.8 Hz, 1H), 5.24 (s, 1H), 5.14 (s, 1H), 4.39-4.37 (m, 1H), 4.5-4.23 (m, 3H), 4.1-4.0 (m, 2H), 3.9-3.71 (m, 6H), 3.65-3.58 (m, 5H), 3.56-3.23 (m, 12H), 3.01-2.97 (m, 2H), 2.92-2.9 (m, 2H), 2.11-2.0 (m, 2H), 1.68-1.6 (m, 2H). $^{13}$C NMR (125 MHz, $D_2O$) δ 176.4, 136.8, 129.9, 129.6, 128.3, 110.9, 96.8, 96.1, 86.0, 81.9, 78.4, 75.9, 74.5, 74.2, 71.0, 70.3, 70.0, 69.6, 68.3, 67.9, 61.0, 60.8, 54.6, 51.6, 50.0, 49.9, 49.7, 49.3, 44.7, 44.1, 37.9, 32.5, 31.6, 30.7. ESI/MS calcd for $C_{37}H_{65}N_7O_{16}$ (M+H$^+$) 864.45. found 864.8.

Example 58

Synthesis of 4',6'-O-benzylidene-N-1-haba-6-O-(1,3-diaminoethyl)-penta-N-benzyloxycarbonyl paromomycin (28b)

27 ⟶

91
-continued

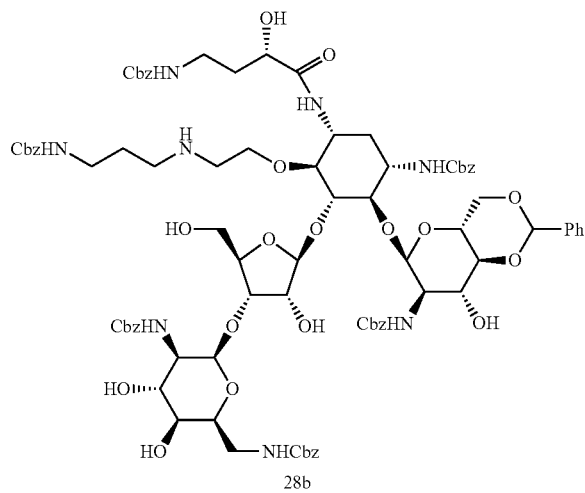

28b

Ozone gas was passed to a stirred solution of Compound 27 (78 mg, 0.037 mmol) in dry dichloromethane (3 mL) at −78° C. for 2 hours. Ozone was degassed by passing nitrogen gas for 10 minutes. To this solution was added excess dimethyl sulfide (0.2 mL). with stirring for 2 hours at room temperature. Then the solvent was evaporated under reduced pressure and the material was extracted with ethyl acetate. The organic layer was washed with NaHCO$_3$ and brine then dried over anhydrous Na$_2$SO$_4$. Evaporation of the solvent gave the crude material (75 mg). This material was dissolved in MeOH and NH-Cbz-(CH$_2$)$_2$CH$_2$NH$_2$ (15 mg, 0.072 mmol) and one drop of AcOH were added with stirring for 5 minutes. NaBH$_3$CN (5 mg, 0.081 mmol) was added with stirring for 12 hours at room temperature. Evaporation of the solvent followed by usual work up gave the crude product (58 mg). This material was dissolved in dry pyridine (1 mL) followed by the addition of HF.Py (1 mL) at 0° C. and the reaction was slowly brought to room temperature and stirred for 2 days. Water was added to the reaction mixture and extracted with ethyl acetate followed by washing with brine and the organic layer was dried over Na$_2$SO$_4$. Evaporation of the solvent gave the crude material and this crude product was purified by column chromatography to give Compound 28b (20 mg, 31%, 3 steps).

$[\alpha]_D$=+15.2° (c 0.4, CHCl$_3$). ESI/MS calcd for C$_{87}$H$_{104}$N$_8$O$_{28}$ (M+H$^+$) 1709.7. found 1710.4.

Example 59

Synthesis of N-1-haba-6-O-(1,3-diaminoethyl) paromomycin (29b)

28b ⟶

92
-continued

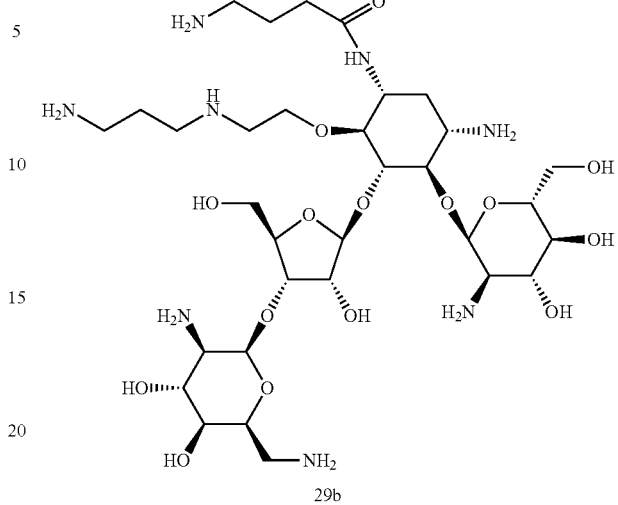

29b

Compound 28b (20 mg, 0.012 mmol) in 2 mL of acetic acid/water mixture (4:1) was stirred at room temperature for 12 hours followed by an additional 6 hours at 55° C. To this reaction mixture 20% Pd(OH)$_2$ (20 mg) was added under an atmosphere of hydrogen (balloon) for 3 hours. The material was filtered over celite and lypholized to give the acetate salt of Compound 29b (13 mg, 87%).

$[\alpha]_D$=+27.33° (c 0.5, H$_2$O). $^1$H NMR (400 MHz, D$_2$O) δ 5.66 (s, 1H), 5.24 (s, 1H), 5.15 (s, 1H), 4.38-4.37 (m, 1H), 4.29-4.08 (m, 6H), 3.84-3.75 (m, 8H), 3.67-3.64 (m, 5H), 3.5-3.26 (m, 7H), 3.19-2.93 (m, 6H), 2.08-1.94 (m, 4H), 1.68-1.59 (m, 2H). $^{13}$C NMR (125 MHz, D$_2$O) δ 176.4, 110.8, 96.8, 96.3, 85.9, 82.0, 78.5, 76.2, 74.5, 74.4, 74.3, 71.0, 70.3, 70.0, 69.6, 68.3, 68.0, 61.0, 60.9, 54.6, 51.6, 50.1, 49.8, 49.3, 45.8, 44.8, 44.2, 37.4, 37.2, 31.7, 30.7, 24.7. ESI/MS calcd for C$_{32}$H$_{64}$N$_8$O$_{16}$ (M+H$^+$) 817.44. found 817.8.

Example 60

General Procedure for the Synthesis of Aminoglycoside Compounds with Ring IV Removed (30a-c)

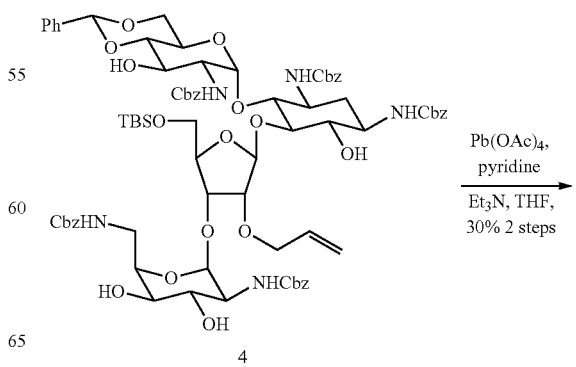

4

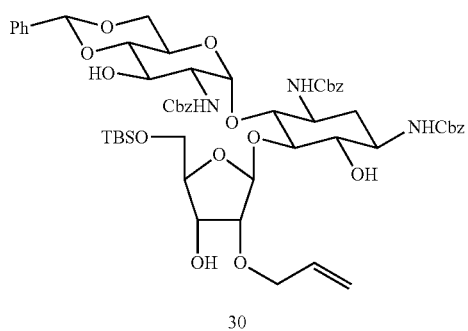

30

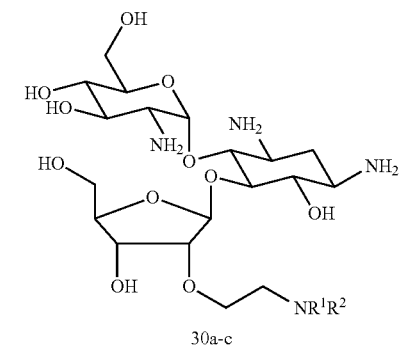

30a-c

Ring IV was eliminated from the common intermediate, Compound 4, using lead tetraacetate (see Hanessian, S.; Takamoto, T. *J. Antibiotics,* 1974, 46, 4009-4012 and Hanessian S.; Takamoto T.; Masse R.; Patil G. Can. *J. Chem.* 1978, 56, 1482). Following the procedures illustrated in the previous examples (protection, generation of an aldehyde, reductive amination and deprotection) such as examples 1-8, a wide variety of 2"-modified derivatives can then be prepared. In particular the 2"-substituted derivatives as described in examples 4-8 can be prepared. Three of the derivatives (30a, 30b and 30c) were prepared and have assay data in subsequent examples.

| Compound# | $R^1$ | $R^2$ |
|---|---|---|
| 30a | H | H |
| 30b | H | $(CH_2)_3NH_2$ |
| 30c | H | $(CH_2)_2Ph$ |

See Example 8 for additional $R^1R^2$ groups.

Example 61

5",6'-O-bis-tert-butyldimethylsilanyloxy-penta-N-benzyloxycarbonyl-3',4'-dideoxy paromomycin (32)

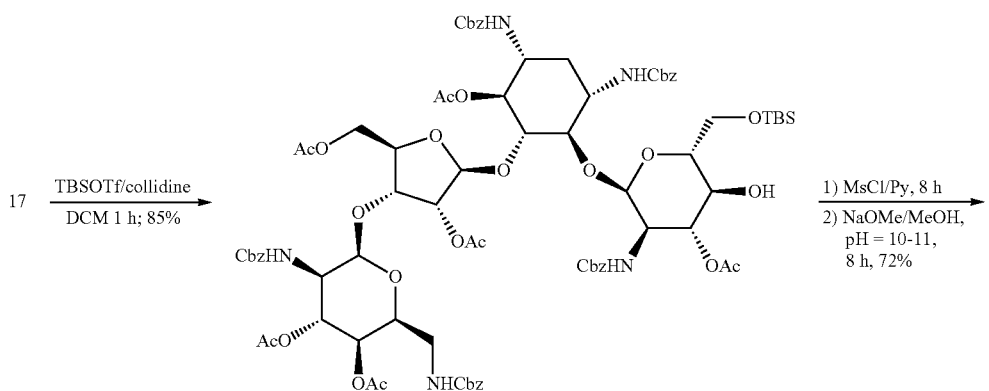

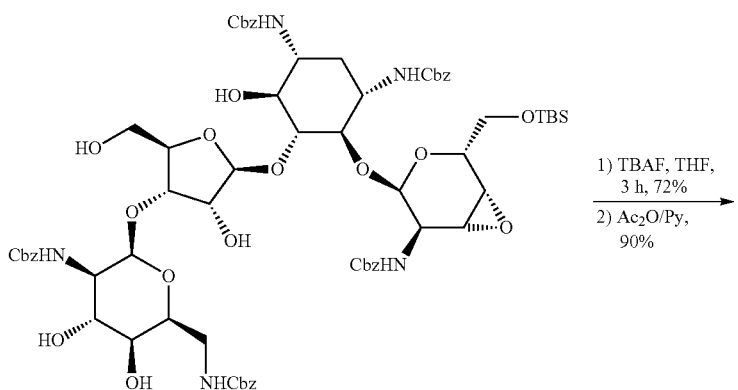

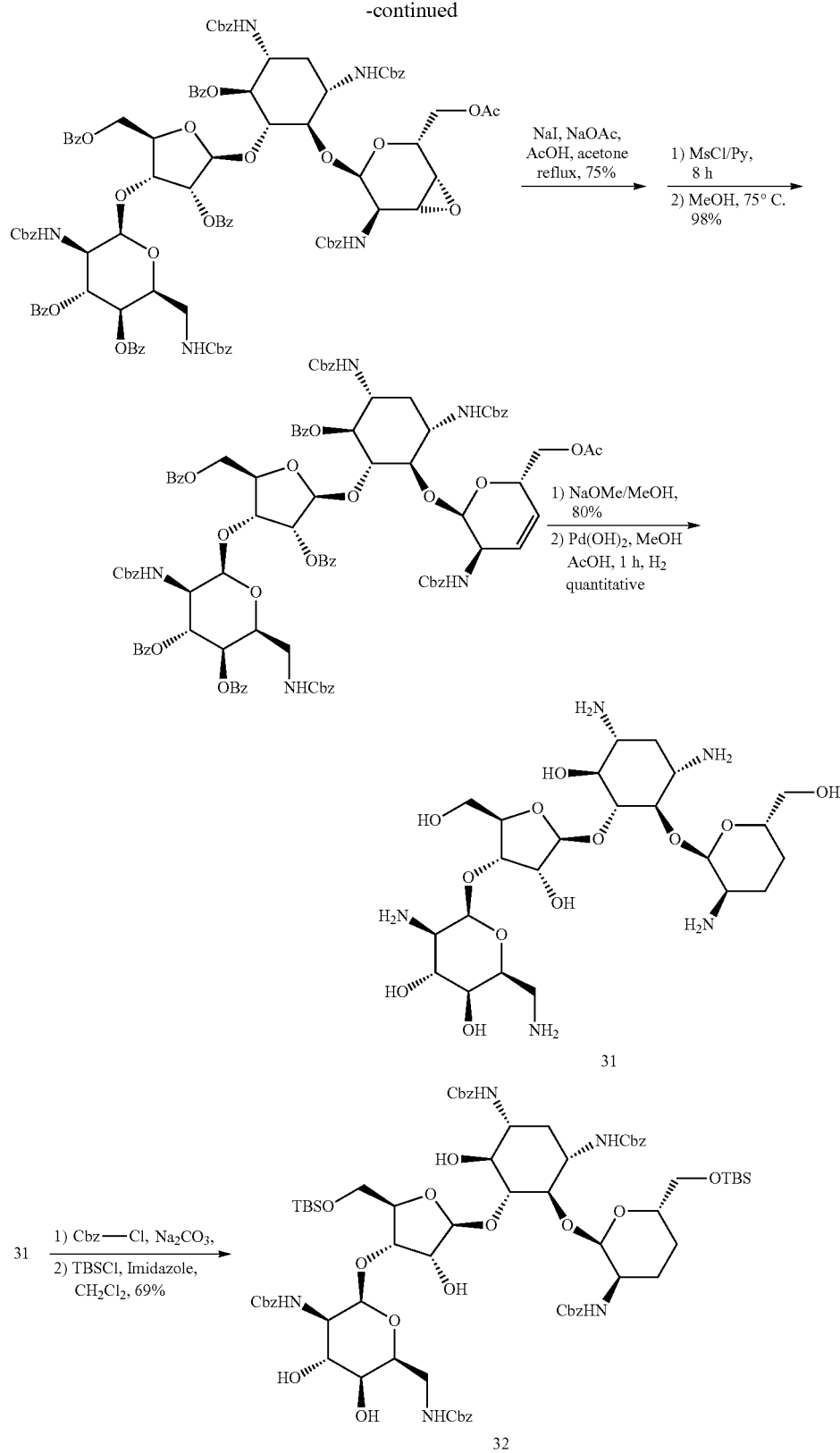
Compound 31 is prepared as per Battistini et al., Semisynthetic aminoglycoside antibiotics, IV, 3',4'-Dideoxyparomomycin and analogs. *J. Antibiotics* 1982, 35, 98-101. Alternatively, Compound 31 is prepared according to the scheme of this example from Compound 17, then protected with Cbz groups as described in Example 1. To a solution of Compound 31 (272 mg, 0.22 mmol) and imidazole (64 mg, 0.91 mmol) in dry dichloromethane (5 mL) was added TBSCl (77 mg, 0.51 mmol) at room temperature with stirring for 24 hours. A few drops of water were added to quench the excess TBSCl and the mixture was extracted with ethyl acetate. The organic layer was washed with saturated brine and dried over anhydrous $Na_2SO_4$, followed by concentration of the solvent to give the crude product. The crude product was purified by flash column chromatography to yield Compound 32 (225 mg, 68%).

$[\alpha]_D$=+29° (c 0.7, $CHCl_3$). HRMS calcd for $C_{75}H_{103}N_5O_{22}Si_2$ (M+H$^+$): 1482.67060. found: 1482.66832.

Example 62

2″-O-allyl-5″,6′-O-bis-tert-butyldimethylsilanyloxy-penta-N-benzyloxycarbonyl-3′,4′-dideoxy paromomycin (33)

32 ⟶

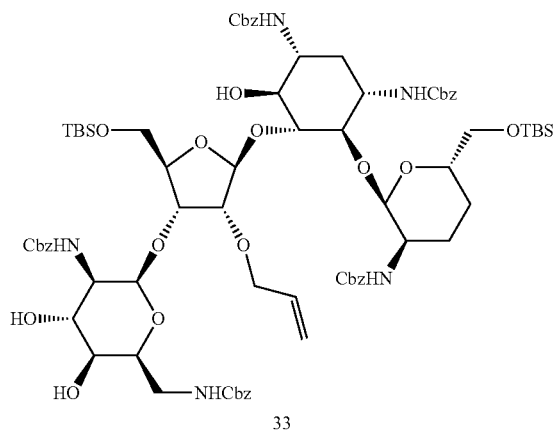

33

To a stirred solution of Compound 32 (222 mg, 0.15 mmol) and allyl iodide (70 μL, 0.75 mmol) in dry THF (5 mL) was added 0.5 M KHMDS in THF (300 μL, 0.15 mmol) at 0° C. The reaction mixture was slowly brought to room temperature and stirred for 12 hours. A few drops of saturated $NH_4Cl$ solution were added to quench the reaction and the mixture was extracted with ethyl acetate. The organic layer was washed with saturated brine, dried over anhydrous $Na_2SO_4$ and concentrated to give the corresponding crude product. The crude product was purified by flash column chromatography to give Compound 33 (155 mg, 68%).

$[\alpha]_D$=+18.75° (c 0.4, $CHCl_3$). ESI/MS calcd for $C_{78}H_{107}N_5O_{22}Si_2$ (M+H$^+$): 1522.69. found: 1522.7.

Example 63

2″-O-allyl-tetra-tert-butyldimethylsilanyloxy-penta-N-benzyloxycarbonyl-3′,4′-dideoxy paromomycin (34)

33 ⟶

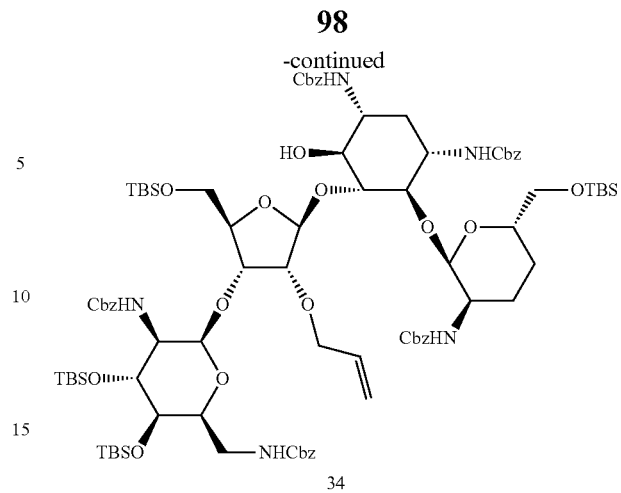

34

To a stirred solution of Compound 33 (800 mg, 0.53 mmol) in dry dichloro-methane (15 mL) was added 2,4,6-collidine (321 mg, 2.65 mmol) and TBSOTf (693 mg, 2.65 mmol) at 0° C. The reaction mixture was slowly brought to room temperature and stirred for 12 hours. A few drops of water were added to quench the excess TBSOTf, followed by extraction with dichloromethane. The organic layer was washed with saturated brine, dried over anhydrous $Na_2SO_4$ and concentrated to give the crude product. The crude product was purified by flash column chromatography to yield Compound 34 (715 mg, 77%).

$[\alpha]_D$=+10.33° (c 0.6, $CHCl_3$). ESI/MS calcd for $C_{90}H_{135}N_5O_{22}Si_4$ (M+H$^+$): 1750.87. found: 1751.4.

Example 64

Cyclic Carbamate (35)

34 ⟶

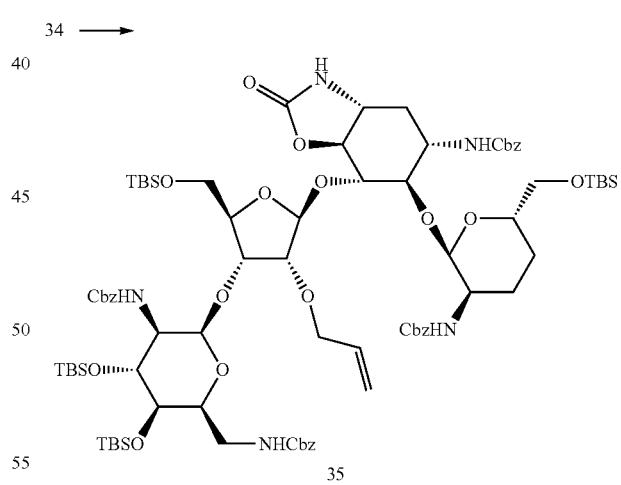

35

To a solution of Compound 34 (692 mg, 0.4 mmol) in dry DMF (10 mL) was added 60% NaH in mineral oil (19 mg) at 0° C. with stirring continued 6 hours at 0° C. A few drops of saturated ammonium chloride solution were added, followed by extraction with ethyl acetate. The organic layer was washed with saturated brine, dried over anhydrous $Na_2SO_4$ and concentrated to give the crude product. The crude product was purified by flash column chromatography to yield Compound 35 (323 mg, 49%) and 180 mg (26%) of the starting material Compound 34 was also recovered.

$[\alpha]_D$=+18.33° (c 0.3, CHCl$_3$). ESI/MS calcd for C$_{83}$H$_{127}$N$_5$O$_{21}$Si$_4$ (M+H$^+$): 1642.81. found: 1643.5.

Example 65

2"-O-allyl-tetra-tert-butyldimethylsilanyloxy-tetra-N-benzyloxycarbonyl-3',4'-dideoxy paromomycin (36)

35 ⟶

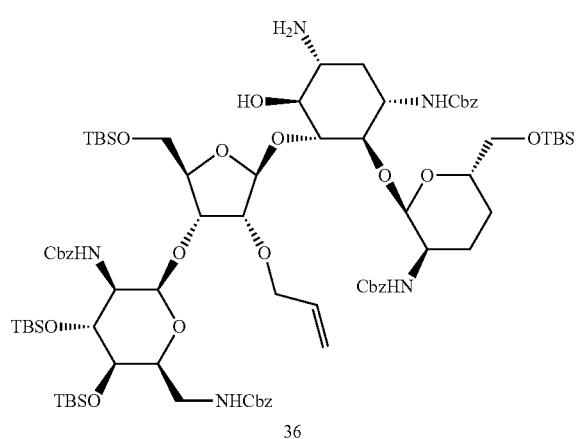

36

To a solution of Compound 35 (350 mg, 0.21 mmol) in DMF (5 mL) was added 0.5 mL of aqueous LiOH (18 mg, 0.43 mmol) with stirring continued for 4 hours at room temperature. A few drops of saturated ammonium chloride solution were added, followed by extraction with ethyl acetate. The organic layer was washed with saturated brine, dried over anhydrous Na$_2$SO$_4$ and concentrated to give the crude product. The crude product was purified by flash column chromatography to give Compound 36 (300 mg, 88%).

$[\alpha]_D$=+20.33° (c 0.5, CHCl$_3$). ESI/MS calcd for C$_{82}$H$_{129}$N$_5$O$_{20}$Si$_4$ (M+H$^+$):1616.83. found: 1617.4.

Example 66

2"-O-allyl-tetra-tert-butyldimethylsilanyloxy-penta-N-benzyloxycarbonyl-3',4'-dideoxy-N-1-haba paromomycin (37)

36 ⟶

-continued

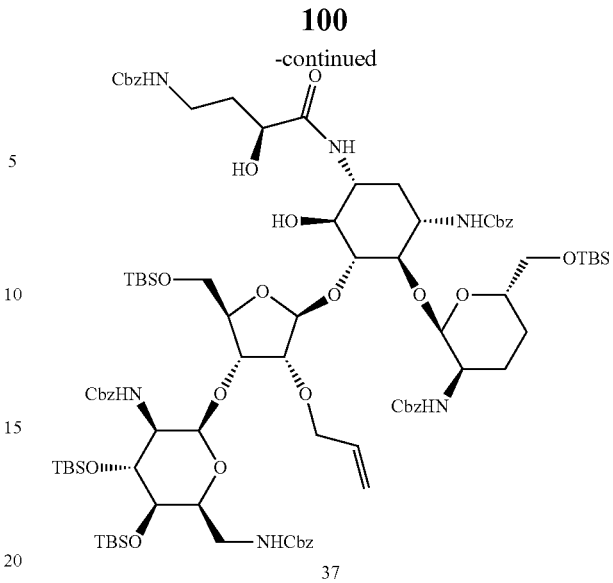

37

To a solution of benzyloxy 4-hydroxy aminobutric acid (66 mg, 0.26 mmol), N-hydroxy succinimide (121 mg, 1.05 mmol) in dry THF (10 mL) was added DCC (216 mg, 1.05 mmol) with stirring continued for 1 hour at room temperature. To this reaction mixture the free amine, Compound 36 (340 mg, 0.21 mmol) in dry THF (2 mL) and triethyl amine (0.2 mL, 0.42 mmol) were added with stirring for 12 hours at room temperature. Evaporation of the solvent and purification of the residue by flash column chromatography gave Compound 37 (290 mg, 75%).

$[\alpha]_D$=+16.67° (c 0.12, CHCl$_3$). ESI/MS calcd for C$_{94}$H$_{142}$N$_6$O$_{24}$Si$_4$ (M+H$^+$): 1851.91. found: 1852.8.

Example 67

2"-O-phenylethylaminoethyl-penta-N-benzyloxycarbonyl-3',4'-dideoxy-N-1-haba paromomycin (38)

37 ⟶

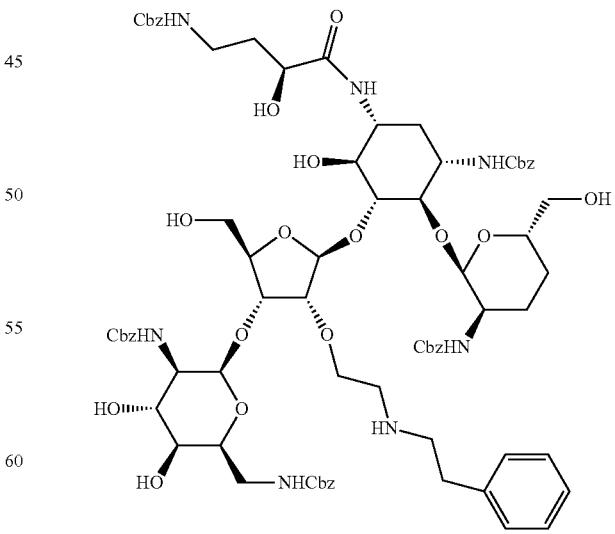

38

Ozone gas was passed through a stirred solution Compound 37 (135 mg, 0.073 mmol) in dry dichloromethane (5 mL) at −78° C. for 2 hours. Then the excess ozone was degassed by passing nitrogen gas for 10 minutes followed by the addition of excess dimethyl sulfide (0.1 mL). This solution was stirred for 2 hours at room temperature. The solvent was removed under reduced pressure and the resulting material was extracted with ethyl acetate, washed with NaHCO$_3$ and brine and the organic layer was dried over anhydrous Na$_2$SO$_4$. Evaporation of the solvent gave the crude material (125 mg). This material was dissolved in MeOH and phenyl ethyl amine (16 mg, 0.13 mmol) and one drop of AcOH was added with stirring for 5 minutes. NaBH$_3$CN (9 mg, 0.15 mmol) was added and stirred for 12 hours at room temperature. Evaporation of the solvent gave the crude product (70 mg). This material was dissolved in dry pyridine (1 mL) followed by the addition of HF.Py (1 mL) at 0° C. and the reaction was slowly brought to room temperature and stirred for 2 days. Water was added and the mixture was extracted with ethyl acetate, washed with brine and the resulting organic layer was dried over Na$_2$SO$_4$. Evaporation of the solvent gave the crude material which was further purified by silica gel flash column chromatography to give Compound 38 (33 mg, 30%).

[α]$_D$=+20.7° (c 0.2, CHCl$_3$). ESI/MS calcd for C$_{77}$H$_{95}$N$_7$O$_{24}$ (M+H$^+$):1502.64. found: 1504.1.

Example 68

2''-O-phenylethylaminoethyl-3',4'-dideoxy-N-1-haba paromomycin (39)

38 ⟶

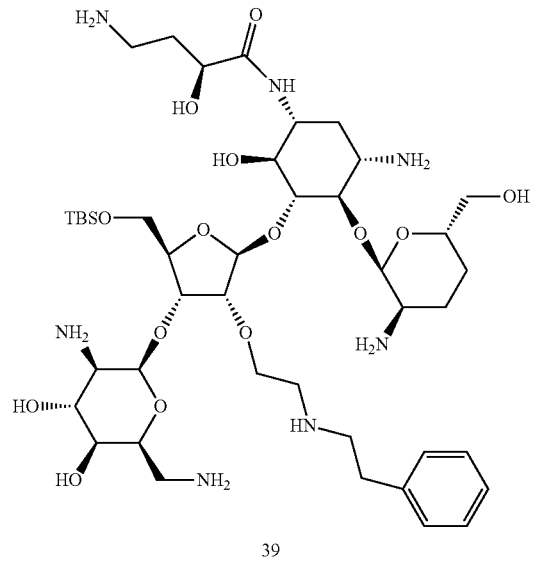

39

To a stirred solution of Compound 38 (20 mg, 0.013 mmol) in AcOH/water (4:1) mixture was added 20% Pd(OH)$_2$ (20 mg) and stirred under an atmosphere of hydrogen using a hydrogen balloon for 2 hours. Filteration over celite followed by lypholyzation gave Compound 39 (16 mg, quantitative).

[α]$_D$=+33.33° (c 0.15, H$_2$O). $^1$H NMR (400 MHz, D$_2$O) δ 7.4-7.1 (m, 5H), 5.5 (s, 1H), 5.28 (s, 1H), 5.08 (s, 1H), 4.5-4.4 (m, 1H), 4.2-4.0 (m, 5H), 3.9-3.6 (m, 9H), 3.5-3.1 (m, 12H), 3.0-2.8 (m, 4H), 2.1-1.4 (m, 8H); $^{13}$C NMR (125 MHz, D$_2$O) δ 175.9, 136.6, 129.4, 129.1, 127.7, 108.6, 95.5, 95.0, 86.0, 81.0, 80.8, 77.5, 74.0, 73.8, 71.1, 70.7, 70.0, 68.0, 67.6, 65.6, 63.6, 59.9, 51.1, 49.7, 49.2, 49.1, 48.8, 47.2, 40.6, 37.0, 31.9, 31.2, 30.32, 24.25, 21.36; ESI/MS calcd for C$_{37}$H$_{65}$N$_7$O$_{14}$ (M+H$^+$): 832.45895. found: 832.46627.

Example 69

2''-O-allyl-4',6'-O-benzylidene-tetra-O-tert-butyldimethylsilanyloxy-penta-N-benzyloxycarbonyl paromomycin (40)

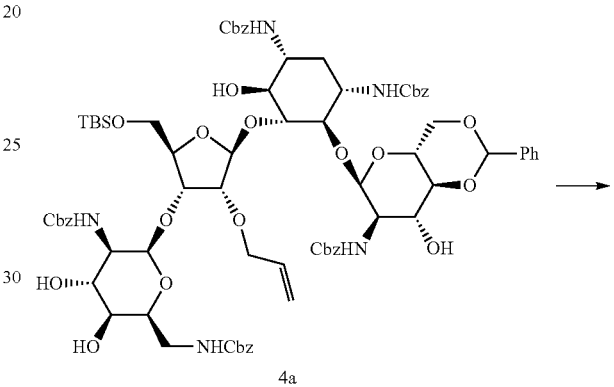

4a

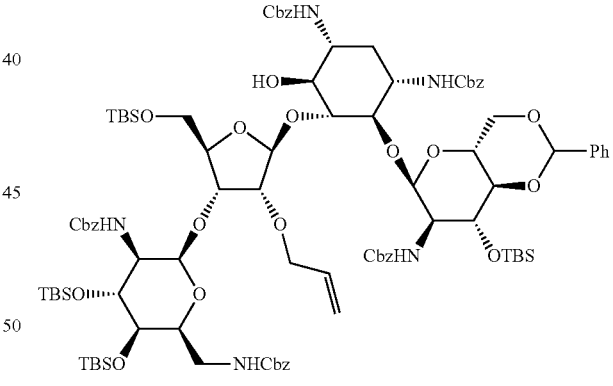

40

To a stirred solution of Compound 4a (3.8 g, 2.49 mmol) in dry dichloromethane (80 mL) was added 2,4,6-collidine (1.8 g, 1.97 mmol) and TBSOTf (3.94 g, 14.92 mmol) at 0° C. The reaction mixture was slowly brought to room temperature and stirred for 12 hours. A few drops of water were added to quench the excess TBSOTf and the mixture was extracted with dichloromethane. The organic layer was washed with saturated brine, dried over anhydrous Na$_2$SO$_4$ and the solvent was removed under reduced pressure to give the crude product. The crude product was purified by flash column chromatography to give Compound 40 (1.6 g, 35%) and 1 g of (20%) the corresponding fully TBS protected compound.

$[α]_D$=+11.0° (c 1, CHCl$_3$). ESI/MS calcd for C$_{97}$H$_{139}$N$_5$O$_{24}$Si$_4$ (M+H$^+$): 1870.89. found: 1871.6.

Example 70

Synthesis of the Cyclic Carbamate (41)

40 →

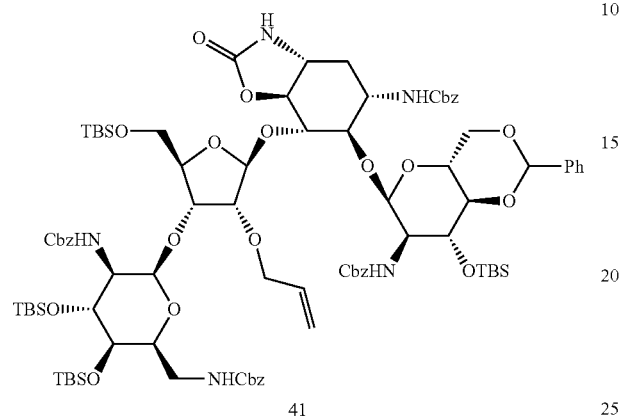

41

To a solution of Compound 40 (1.47 g, 0.783 mmol) in dry DMF (20 mL) was added 60% NaH in mineral oil (36 mg) at 0° C. with stirring continued for an additional 6 hours at 0° C. A few drops of saturated ammonium chloride solution were and the mixture was extracted with ethyl acetate. The organic layer was washed with saturated brine, dried over anhydrous Na$_2$SO$_4$ and concentrated under reduced pressure to give crude product. The crude product was purified by flash column chromatography to give Compound 41 (650 mg, 47%) and 560 mg (38%) of starting material Compound 40 was also recovered. $[α]_D$=+20° (c 1, CHCl$_3$). ESI/MS calcd for C$_{90}$H$_{131}$N$_5$O$_{23}$Si$_4$ (M+H$^+$): 1762.83. found: 1763.2.

Example 71

2"-O-allyl-4',6'-O-benzylidene-tetra-O-tert-butyldimethylsilanyloxy-tetra-N-benzyloxycarbonyl paromomycin (42)

41 →

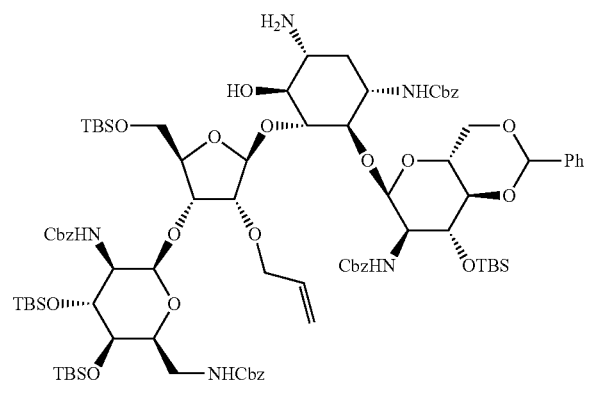

42

To a solution of Compound 41 (730 mg, 0.41 mmol) in DMF (10 mL) was added 1 mL of aqueous LiOH (35 mg, 0.83 mmol) with stirring continued for an additional 6 hours at room temperature. A few drops of saturated ammonium chloride solution were added and the mixture was extracted with ethyl acetate. The organic layer was washed with saturated brine, dried over anhydrous Na$_2$SO$_4$ and concentrated to give crude product. The crude product was purified by flash column chromatography to give Compound 42 (450 mg, 63%) and Compound 41 (264 mg, 36%) was also recovered.

$[α]_D$=+3.77° (c 0.45, CHCl$_3$). ESI/MS calcd for C$_{89}$H$_{133}$N$_5$O$_{22}$Si$_4$ (M+H$^+$): 1736.85. found 1737.2.

Example 72

2"-O-allyl-4',6'-O-benzylidene-tetra-O-tert-butyldimethylsilanyloxy-penta-N-benzyloxycarbonyl-N-1-haba paromomycin (43)

42 →

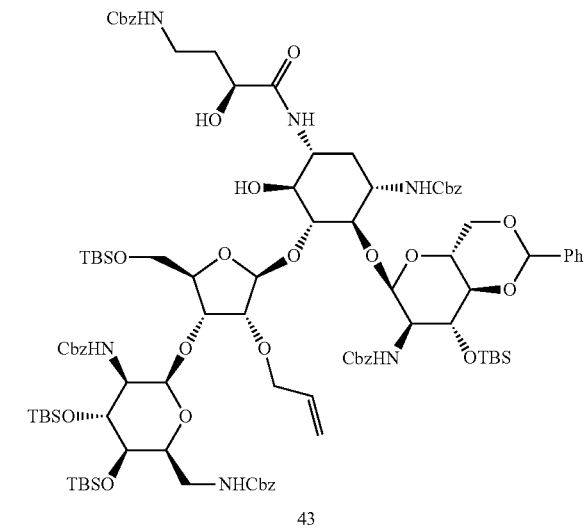

43

To a solution of benzyloxy 4-hydroxy aminobutric acid (364 mg, 1.45 mmol) and N-hydroxy succinimide (167 mg, 1.45 mmol) in dry THF (10 mL) was added DCC (299 mg, 1.45 mmol) with stirring continued for additional 2 hours at room temperature. To this reaction mixture Compound 42 (500 mg, 0.29 mmol) in dry THF (2 mL) and triethyl amine (0.2 mL, 1.45 mmol) was added with stirring for 12 hours at room temperature. Evaporation of the solvent followed by purification by flash column chromatography gave Compound 43 (400 mg, 70%).

$[α]_D$=+13.7° (c 0.5, CHCl$_3$). ESI/MS calcd for C$_{101}$H$_{146}$N$_6$O$_{26}$Si$_4$ (M+H$^+$): 1971.94. found: 1972.7.

Example 73

Synthesis of Aldehyde (44)

43 →

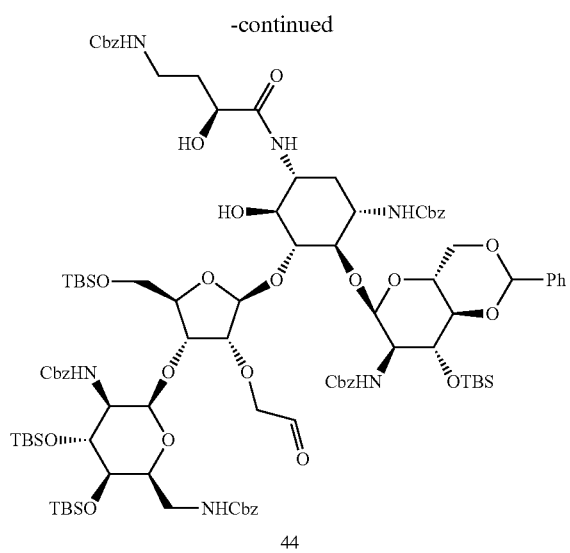

44

Ozone gas was passed through a stirred solution of Compound 43 (400 mg, 0.2 mmol) in dry dichloromethane (10 mL) at −78° C. for 2 hours. The excess ozone was degassed by passing nitrogen gas for 10 minutes followed by the addition of excess PPh$_3$ (210 mg, 0.8 mmol). This solution was stirred for 2 hours at room temperature. The solvent was removed under reduced pressure and the resulting material was extracted with ethyl acetate, washed with NaHCO$_3$ and brine and the organic layer was dried over anhydrous Na$_2$SO$_4$. Evaporation of the solvent gave the crude material, which was purified by column chromatography to give Compound 44 (270 mg, 67%).

$[\alpha]_D$=+20.7° (c 0.9, CHCl$_3$). ESI/MS calcd for C$_{100}$H$_{144}$N$_6$O$_{27}$Si$_4$ (M+H$^+$): 1973.92. found: 1974.4.

Example 74

4',6'-O-benzylidene-penta-N-benzyloxycarbonyl-N-1-haba-2''-O-phenylethylaminoethyl paromomycin (45a)

44 ⟶

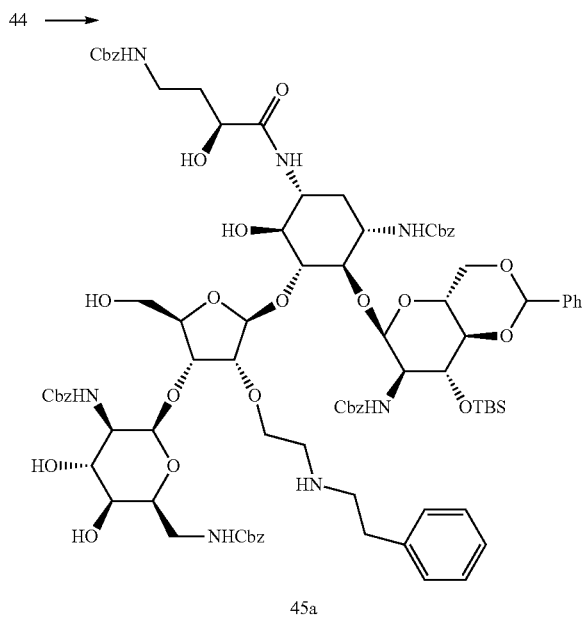

45a

To a stirred solution of Compound 44 (120 mg, 0.061 mmol) was added phenyl ethyl amine (15 mg, 0.12 mmol) and one drop of AcOH with stirring for 5 minutres. NaBH$_3$CN (8 mg, 0.12 mmol) was added with stirring maintained for an additional 12 hours at room temperature. Evaporation of the solvent gave the crude product (120 mg). The crude product was dissolved in dry pyridine (1 mL), HF.Py (1 mL) was added at 0° C. and the reaction was slowly brought to room temperature and stirred for 2 days. Water was added and the mixture was extracted with ethyl acetate. The organic phase was washed with brine and dried over Na$_2$SO$_4$. Evaporation of the solvent gave the crude material which was purified by column chromatography to give Compound 45a (60 mg, 61%).

$[\alpha]_D$=+10.5° (c 0.2, CHCl$_3$). ESI/MS calcd for C$_{84}$H$_{99}$N$_7$O$_{26}$ (M+H$^+$): 1622.66. found: 1623.1.

Example 75

N-1-haba-2''-O-phenylethylaminoethyl paromomycin (46a)

45a ⟶

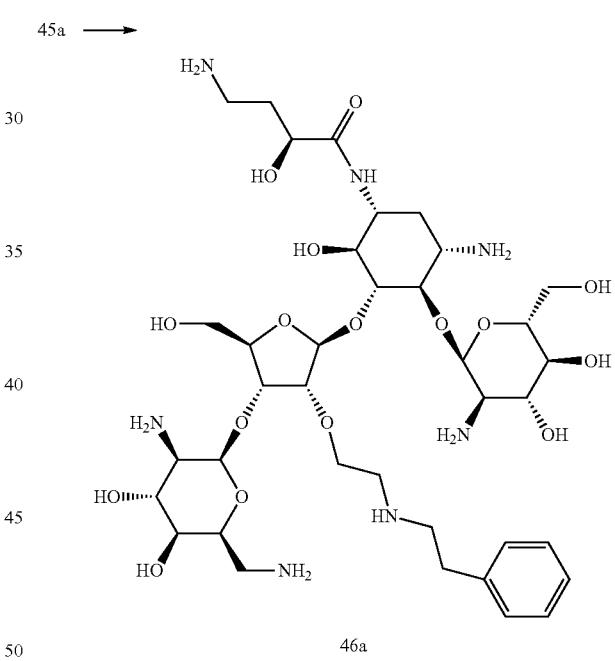

46a

Compound 45a (30 mg, 0.019 mmol) in 3 mL of acetic acid and water mixture (4:1) was stirred at room temperature for 12 hours and at 55° C. for an additional 6 hours. To this reaction mixture 20% Pd(OH)$_2$ (30 mg) was added under an atmosphere of hydrogen (balloon) for 3 hours. The reaction mixture was filtered through celite and lypholized to give Compound 46a (21 mg, 91%).

$[\alpha]_D$=+48.5° (c 0.2, H$_2$O). $^1$H NMR (400 MHz, D$_2$O) δ 7.34-7.18 (m, 5H), 5.7 (d, J=3.6 Hz, 1H), 5.33 (s, 1H), 5.1 (s, 1H), 4.5-4.49 (m, 1H), 4.2-4.03 (m, 5H), 3.9-3.76 (m, 9H), 3.66-3.61 (m, 4H), 3.5-3.4 (m, 1H), 3.38-3.18 (m, 10H), 3.0-2.97 (m, 2H), 2.92-2.89 (m, 2H), 2.1-2.0 (m, 2H), 1.61-1.58 (m, 2H); $^{13}$C NMR (125 MHz, D$_2$O) δ 175.9, 136.6, 129.4, 129.1, 127.8, 108.5, 96.3, 95.0, 86.0, 81.0, 80.7, 77.7, 74.0, 73.6, 70.7, 69.8, 69.5, 69.2, 68.0, 67.6, 65.6, 60.5, 59.4, 54.2, 51.1, 49.5, 49.1, 48.8, 47.3, 40.6, 37.0, 31.9, 31.2, 30.39, HRMS calcd for $C_{37}H_{65}N_7O_{16}$ (M+H$^+$): 864.44878. found: 864.45613.

Example 76

4',6'-O-benzylidene-penta-N-benzyloxycarbonyl-N-1-haba-2''-O-(1,3-diamino)ethyl paromomycin (45b)

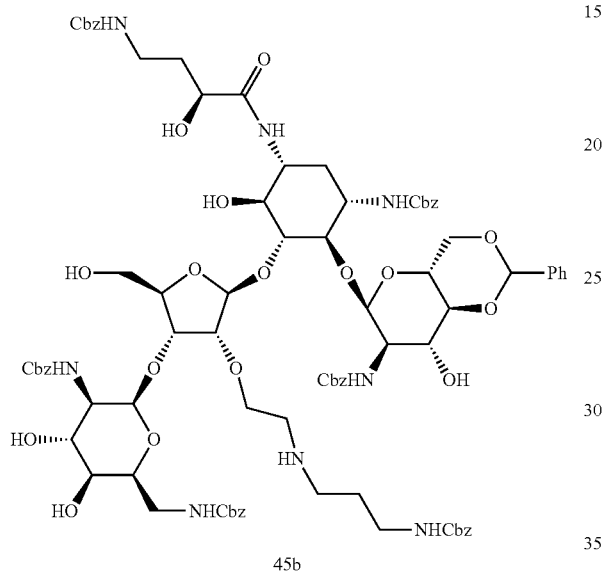

45b

To a solution of Compound 44 (50 mg, 0.025 mmol) was added N-Cbz-(CH$_2$)$_2$CH$_2$NH$_2$ (16 mg, 0.12 mmol) followed by one drop of AcOH with stirring for 5 minutes. NaBH$_3$CN (5 mg, 0.12 mmol) was added with stirring for 12 hours at room temperature. Evaporation of the solvent gave the crude product. The crude product was dissolved in dry pyridine (1 mL) and HF.Py (1 mL) was added at 0° C. The reaction mixture was slowly brought to room temperature and stirred for 2 days. Water was added and the mixture was extracted with ethyl acetate, washed with brine and dried over Na$_2$SO$_4$. Evaporation of the solvent gave the crude material which was purified by column chromatography to give Compound 45b (18 mg, 42%). [α]$_D$=+15.5° (c 0.4, CHCl$_3$). ESI/MS calcd for $C_{87}H_{104}N_8O_{28}$ (M+H$^+$): 1709.70. found: 1710.0.

Example 77

N-1-haba-2''-O-(1,3-diamino)ethyl paromomycin (46b)

45b ⟶

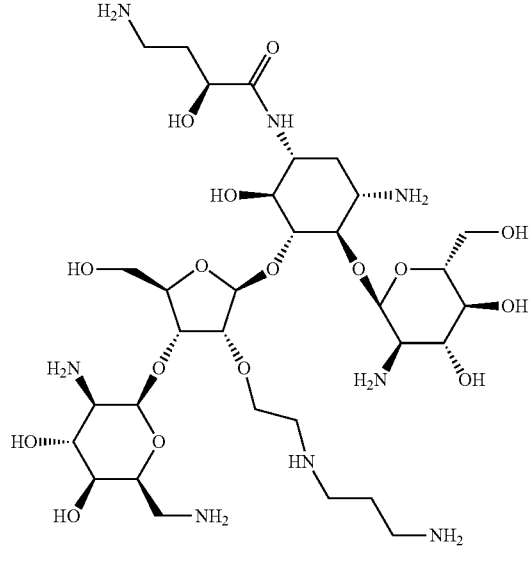

46b

Compound 45b (18 mg, 0.011 mmol) in 1 mL of acetic acid and water mixture (4:1) was stirred for 12 hours at room temperature followed by an additional 6 hours at 55° C. 20% Pd(OH)$_2$ (18 mg) was added under an atmosphere of hydrogen (balloon) with stirring for 3 hours. The mixture was filtered through celite and lypholized to give Compound 46b (14 mg, quantitative).

[α]$_D$=+30° (c 0.7, H$_2$O). $^1$H NMR (400 MHz, D$_2$O) δ 5.7 (s, 1H), 5.4 (s, 1H), 5.17 (s, 1H), 4.55-4.5 (m, 1H), 4.25-4.01 (m, 6H), 3.9-3.19 (m, 20H), 3.06-2.9 (m, 6H), 2.1-1.55 (m, 6H); $^{13}$C NMR (125 MHz, D$_2$O) δ 175.2, 107.7, 95.6, 94.2, 85.1, 81.3, 80.3, 79.8, 76.9, 73.3, 72.9, 70.0, 69.1, 68.7, 68.4, 67.2, 66.8, 59.8, 58.7, 53.4, 50.4, 48.7, 48.3, 46.9, 44.2, 42.0, 39.9, 36.3, 36.1, 30.4, 29.5, 23.1; HRMS calcd for $C_{32}H_{64}N_8O_{16}$ (M+H$^+$): 817.44403. found: 817.45229.

Example 78

Synthesis of Orthogonally Protected Paromomycin (49)

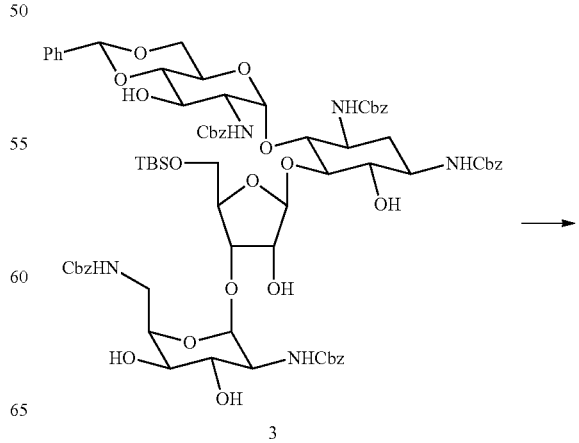

-continued

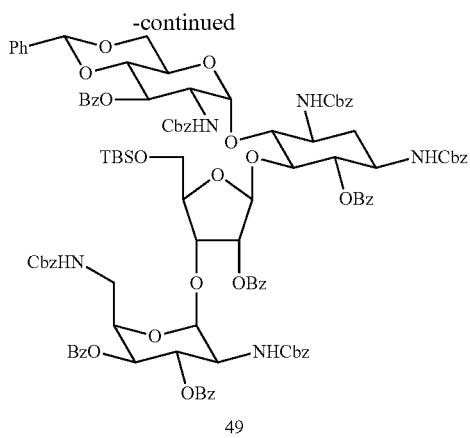

49

A solution containing Compound 3 (540 mg, 0.362 mmol) and N,N-dimethylamino pyridine (176 mg, 1.44 mmol) in dry pyridine (20 mL) was treated with benzoyl chloride (0.85 mL, 7.25 mmol) at 0° C. The reaction mixture was stirred at room temperature for 12 hours and at 70° C. for an additional 24 hours wherein the reaction was shown to hve gone to completion (tic) with the formation of two products with a 3:1 ratio. Water (1 mL) was added and after standing for 10 minutes, the solvent was removed under vacuum. The residue was dissolved in EtOAc/H$_2$O, the aqueous layer was extracted with EtOAc, and the combined organic extracts were washed with water, brine, dried over Na$_2$SO$_4$ and concentrated under vacuum. The crude product was purified by silica gel flash column chromatography (2:3 EtOAc/hexane) to yield Compound 49 (510 mg, 70%).

$[\alpha]_D$+37.91° (c 1.15, CHCl$_3$); R$_f$ 0.43 (1:1 EtOAc/hexane); FAB MS calcd for C$_{111}$H$_{113}$N$_5$O$_{29}$Si (M+H$^+$) 2008.73. found 2008.7. The product with a 3'-OH free was isolated from column with 25% yield (173 mg); $[\alpha]_D$+31.83° (c 1.2, CHCl$_3$); R$_f$ 0.29 (1:1 EtOAc/hexane); FAB MS calcd for C$_{104}$H$_{109}$N$_5$O$_{27}$ (M+H$^+$) 1904.64. found 1904.6.

Example 79

Selective Deblocking of the 5"-Position (50)

49 ⟶

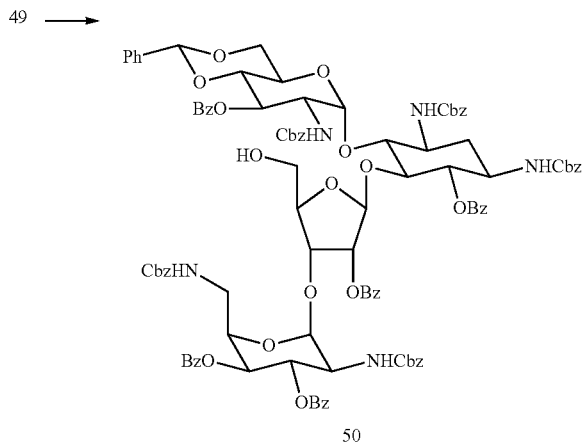

50

A solution of Compound 49 (420 mg, 0.209 mmol) in dry THF was treated with AcOH (119.6 uL, 2.09 mmol) and TBAF successively at 0° C. The reaction mixture was allowed to come to room temperature and further stirred for 24 hours wherein the reaction had gone to completion. The solvent was removed under reduced pressure and the residue was dissolved in EtOAc/H$_2$O, the aqueous layer was extracted with EtOAc, and the combined organic extracts were washed with water, brine, dried over Na$_2$SO$_4$ and concentrated under vacuum. The crude product was purified by silica gel flash chromatography (2:3 EtOAc/hexane) to yield Compound 50 (202 mg, 51%).

$[\alpha]_D$+25.16° (c 0.93, CHCl$_3$); R$_f$ 0.47 (3:2 EtOAc/hexane); LCMS calcd for C$_{105}$H$_{99}$N$_5$O$_{29}$ (M+H$^+$) 1894.93. found 1895.0. The product with 5"-OH and one more additional OH free was isolated from column with 33% yield (125 mg); R$_f$ 0.27 (3:2 EtOAc/hexane).

Example 80

Synthesis of 5"-O-Alkyl paromomycin analogues (51)

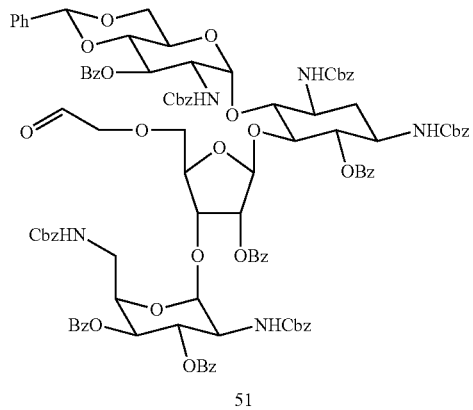

51

Compound 50 (120 mg, 0.063 mmol) was co-distilled with toluene twice and dissolved in dry THF (3 mL) in a flask covered with aluminum foil. Allyl iodide (58.2 pt, 0.63 mmol) was added at 0° C. followed by the dropwise addition of 0.5 M KHMDS solution in toluene (152 μL, 0.076 mmol). The mixture mixture was stirred for 3 hours at room temperature by careful monitoring on TLC. The reaction mixture was quenched with an aqueous solution of NH$_4$Cl (saturated, 0.1 mL) and the solvent was evaporated to dryness in vacuo. The crude product was dissolved in EtOAc, washed with water and the resultant product was purified by silica gel flash chromatography (1:2 EtOAc/hexane) to give the allyl ether (71 mg, 58%).

$[\alpha]_D$+39.64° (c 0.84, CHCl$_3$); R$_f$ 0.62 (1:1 EtOAc/hexane); LCMS calcd for C$_{108}$H$_{103}$N$_5$O$_{29}$ (M+H$^+$) 1936.54. found 1936.6.

The allyl ether (100 mg, 0.0517 mmol) in CH$_2$Cl$_2$ (4 mL) was cooled at −78° C. and ozone was bubbled through for 2 hours after which argon was bubbled through. The mixture was treated with PPh$_3$ (40.64 mg, 0.299 mmol), warmed to the room temperature, solvent was removed under vacuum and the crude aldehyde was purified by silica gel flash chromatography (2:3 EtOAc/hexane) to give the aldehyde, Compound 51 (60 mg, 60%); $R_f$ 0.38 (1:1 EtOAc/hexane).

Example 81

Synthesis of 5"-O-Alkyl paromomycin analogues (52 and 53)

51 ⟶

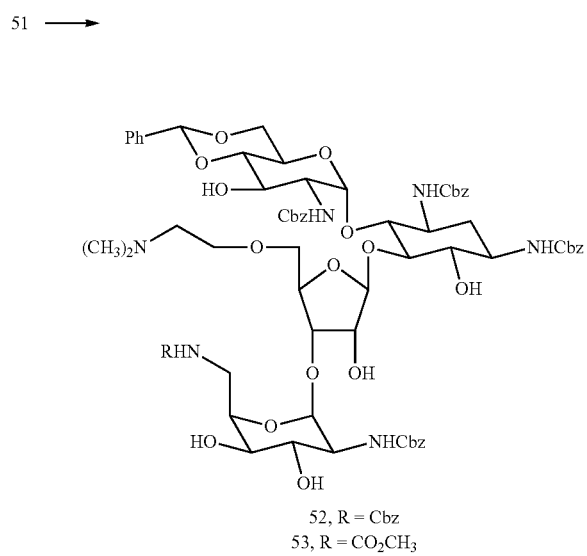

52, R = Cbz
53, R = CO$_2$CH$_3$

To a mixture Compound 51 (30 mg, 0.0155 mmol) and N,N-dimethylamine (2.0 M in THF, 80 μL, 0.155 mmol) in dry MeOH (3 mL) was added AcOH (3-4 drops) followed by NaBH$_3$CN (1.0 M in THF, 0.15 mL, 0.155 mmol). The mixture was stirred at room temperature overnight until disappearance of Compound 51. The reaction mixture was diluted with EtOAc (10 mL) and washed with a solution of NaHCO$_3$ (saturated, 2 mL) and dried over Na$_2$SO$_4$. After evaporation of the solvents, the residue was purified by silica gel flash column chromatography (48:1 CH$_2$Cl$_2$/MeOH) to give the fully protected 5"-(2-dimethylamino) ethoxy derivative as white solid (26 mg, 85%).

$[\alpha]_D$+21.97° (c 1.57, CHCl$_3$); $R_f$ 0.67 (1:19 MeOH/CH$_2$Cl$_2$); LCMS calcd for C$_{109}$H$_{108}$N$_6$O$_{29}$ (M+H$^+$) 1966.05. found 1966.4.

A solution of the fully protected 5"-(2-dimethylamino) ethoxy derivative (20 mg, 0.0102 mmol) in dry MeOH (2 mL) was treated with a catalytic amount of NaOMe in dry MeOH (1 mL, pH 8-9) and stirred at room temperature for 3 hours to completion of reaction. The reaction mixture was neutralized by addition of dry-ice, and the solvent was evaporated to dryness under vacuum. The crude product was purified by silica gel flash column chromatography (1:19 MeOH/CH$_2$Cl$_2$) to give Compound 52 (8.8 mg, 60%).

$[\alpha]_D$+18.54° (c 0.44, MeOH); $R_f$ 0.32 (1:19 MeOH/CH$_2$Cl$_2$); LCMS calcd for C$_{74}$H$_{88}$N$_6$O$_{24}$ (M+H$^+$) 1445.59. found 1445.9.

The product with 6'''-N methylcarbamate, Compound 53 was isolated from column chromatography with 20% yield (3 mg).

$[\alpha]_D$+15.6° (c 0.3, MeOH); $R_f$ 0.32 (1:19 MeOH/CH$_2$Cl$_2$); LCMS calcd for C$_{74}$H$_{88}$N$_6$O$_{24}$ (M+H$^+$) 1368.23. found 1369.3.

Example 82

Synthesis of 5"-O-(2-N,N-dimethylamino ethyl) paromomycin (54), (55)

52 ⟶
53 ⟶

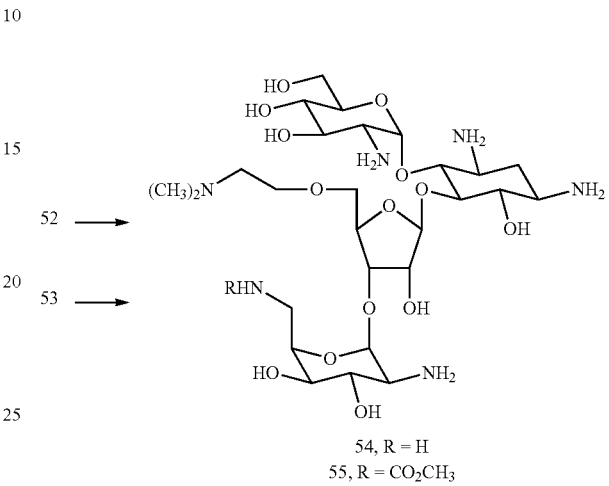

54, R = H
55, R = CO$_2$CH$_3$

Compound 52 (6 mg, 0.0041 mmol) was dissolved in AcOH—H$_2$O (4:1, 2 mL) and heated at 60° C. for 2 hours to completion of reaction. The solvent was removed under reduced pressure and the crude product was dissolved in MeOH—H$_2$O (1:1, 2 mL). 20% palladium hydroxide on carbon was added and the suspension was stirred at room temperature overnight under an atmosphere of hydrogen (hydrogen balloon). The mixture was filtered through a layer of Celite, concentrated under vacuum, and the residue was dissolved in AcOH—H$_2$O (2:1, 0.5 mL) and lyophilized to afford Compound 54 (4.1 mg, quantitative) as a white solid.

$[\alpha]_D$+33.07° (c 0.26, H$_2$O); $^1$H NMR (400 MHz, D$_2$O) δ 5.34 (s, 1H), 5.23 (s, 1H), 5.0 (s, 1H), 4.33-4.12 (m, 4H), 4.11-4.0 (m, 1H), 3.94-3.83 (m, 1H), 3.75-3.63 (m, 5H), 3.61-3.58 (m, 4H), 3.50-3.21 (m, 8H), 3.13-2.93 (m, 3H), 2.78 (s, 6H), 2.17-2.08 (m, 1H), 1.82 (s, 15H), 1.44-1.37 (m, 1H); LCMS calcd for C$_{27}$H$_{54}$N$_6$O$_{14}$) 687.37. found 687.6.

Compound 53 was also hydrogenolysed following the above procedure and lyophilized to give Compound 55 (2.3 mg, quantitative).

$^1$H NMR (400 MHz, D$_2$O) δ 5.36 (s, 1H), 5.25 (s, 1H), 5.0 (s, 1H), 4.35-4.14 (m, 4H), 4.10-4.0 (m, 1H), 3.96-3.85 (m, 1H), 3.78-3.64 (m, 5H), 3.62-3.59 (m, 4H), 3.55 (s, 3H), 3.51-3.22 (m, 8H), 3.15-2.96 (m, 3H), 2.78 (s, 6H), 2.18-2.09 (m, 1H), 1.82 (s, 15H), 1.45-1.38 (m, 1H); LCMS calcd for C$_{29}$H$_{56}$N$_6$O$_{16}$ (M+H$^+$) 745.38. found 745.6.

Example 83

Synthesis of the 5"-(2-hydroxy)ethoxy-6'''-MeO$_2$CHN intermediate (56)

51 ⟶

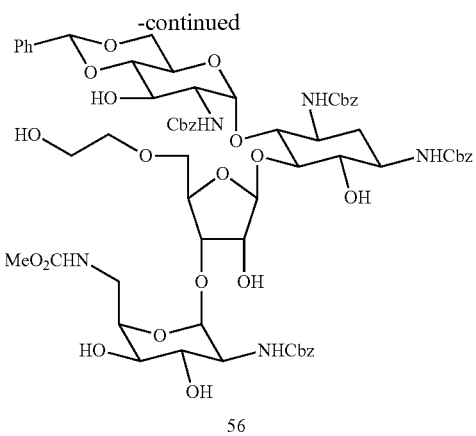

56

A mixture of Compound 51 (20 mg, 0.0103 mmol) in dry MeOH (3 mL) was treated with NaBH$_3$CN (1.0 M in THF, 41.3 µL, 0.0413 mmol). The mixture was stirred at room temperature overnight until disappearance of aldehyde. The solvent was removed under reduced pressure and the reaction mixture was diluted with EtOAc (10 mL) and washed with a solution of NaHCO$_3$ (saturated, 2 mL) and dried over Na$_2$SO$_4$. After evaporation of the solvents, the residue was purified by silica gel flash column chromatography (48:1 CH$_2$Cl$_2$/MeOH) to give the 5"-(2-hydroxy)ethoxy derivative as white solid (16 mg, 80%).

$[\alpha]_D$+19.8° (c 0.8, CHCl$_3$); R$_f$ 0.30 (1:1 EtOAc/hex); LCMS calcd for C$_{107}$H$_{103}$N$_5$O$_{30}$ (M+H$^+$) 1939.1. found 1939.2.

A solution of above 5"-(2-hydroxy)ethoxy derivative (16 mg, 0.0082 mmol) in dry MeOH (2 mL) was treated with a catalytic amount of NaOMe in dry MeOH (1 mL, pH 8-9) and stirred at room temperature for 3 hours to completion of reaction. The reaction mixture was neutralized by addition of dry-ice, and the solvent was evaporated to dryness under vacuum. The crude product was purified by silica gel flash column chromatography (1:19 MeOH/CH$_2$Cl$_2$) to give Compound 56 (8 mg, 72%) as a major product.

$[\alpha]_D$+22.0° (c 0.4, MeOH); R$_f$ 0.42 (1:19 MeOH/CH$_2$Cl$_2$); LCMS calcd for C$_{74}$H$_{88}$N$_6$O$_{24}$ (M+Na$^+$) 1364.30. found 1364.5.

Example 84

5"-O-(2-hydroxyethyl)-6'-N-methoxycarbonyl paromomycin (57)

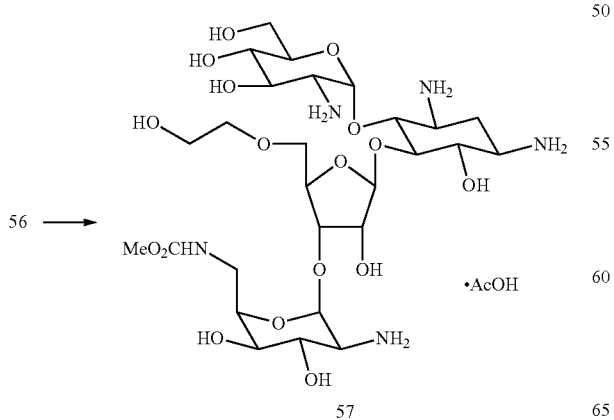

57

Compound 56 (6 mg, 0.0043 mmol) was dissolved in AcOH—H$_2$O (4:1, 2 mL) and heated at 60° C. for 2 hours to completion of reaction. The solvent was removed under reduced pressure and the crude product was dissolved in MeOH—H$_2$O (1:1, 2 mL), followed by addition of 20% palladium hydroxide on carbon with stirring under an atmosphere of hydrogen (hydrogen balloon). The mixture was filtered through a layer of Celite, concentrated under vacuum, and the residue was dissolved in AcOH—H$_2$O (2:1, 0.5 mL) and lyophilized to give Compound 57 (4.1 mg, quantitative) as a white solid.

$[\alpha]_D$+36.10° (c 0.20, H$_2$O); $^1$H NMR (400 MHz, D$_2$O) δ 5.39 (s, 1H), 5.19 (s, 1H), 4.90 (s, 1H), 4.30-4.10 (m, 3H), 4.0-3.93 (m, 2H), 3.90-3.82 (m, 1H), 3.79-3.55 (m, 12H), 3.51 (s, 3H), 3.40-3.10 (m, 5H), 3.05-2.82 (m, 3H), 2.0-1.95 (m, 1H), 1.74 (s, 12H), 1.35-1.25 (m, 1H); LCMS calcd for C$_{27}$H$_{51}$N$_5$O$_{17}$ (M+H$^+$) 718.33. found 718.5.

Example 85

6'''-N-methoxycarbonyl paromomycin (59)

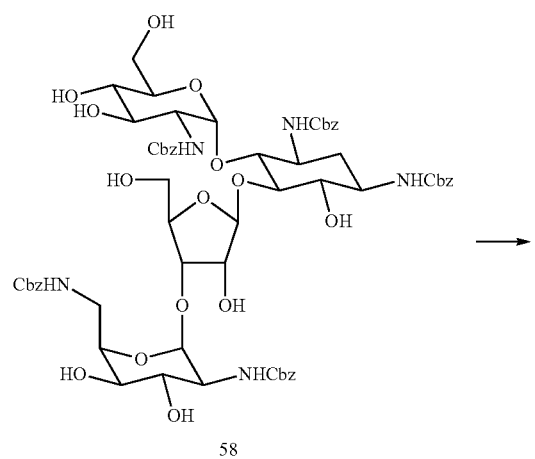

58

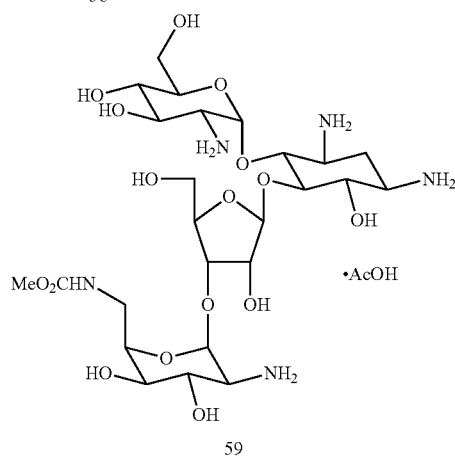

59

Following the procedures of the above examples for Compound 57, paromomycin with 6'''-N-methylcarbamate, Compound 59, was prepared for comparison starting from Compound 58. Compound 58 was obtained following the procedure of Example 1 wherein Compound 58 was isolated prior to addition of benzaldehyde.

$^1$H NMR (400 MHz, D$_2$O) δ 5.56 (s, 1H), 5.20 (s, 1H), 5.02 (s, 1H), 4.27-4.22 (m, 1H), 4.20-4.16 (m, 1H), 4.13-4.0 (m, 2H), 3.95-3.91 (m, 1H), 3.80-3.55 (m, 1H), 3.52 (s, 3H), 3.40-3.36 (m, 3H), 3.25-3.17 (m, 2H), 3.15-2.95 (m, 1H), 2.20-2.15 (m, 1H), 1.75 (s, 12H), 1.54-1.43 (m, 1H); LCMS calcd for C$_{25}$H$_{47}$N$_5$O$_{16}$ (M+H$^+$) 674.30. found 674.5. $^{13}$C NMR (125 MHz, D$_2$O) δ 181.7, 159.7, 110.0, 96.5, 96.2, 85.0, 81.9, 80.2, 76.2, 73.9, 73.7, 73.3, 73.2, 69.0, 69.5, 68.1, 66.6, 60.7, 60.5, 54.3, 52.9, 51.4, 50.4, 49.3, 41.0, 30.6, 23.5.

Example 86

5"-Substituted Partially Protected Paromomycin Analogue (60)

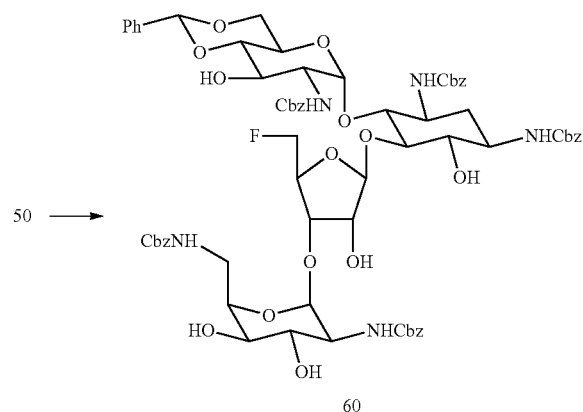

Compound 50 (44 mg, 0.0232 mmol) was dissolved in dry CH$_2$Cl$_2$ (3 mL) and cooled at −78° C. Diethylaminosulfur trifluoride (DAST, 3.4 μL, 0.0255 mmol) was added dropwise at −78° C., and the reaction mixture was allowed to come slowly to the room temperature and further stirred for 1 hour. The reaction mixture was quenched with a few drops of water at 0° C. and diluted with CH$_2$Cl$_2$. The organic layer was washed with water, brine, dried over Na$_2$SO$_4$ and concentrated under vacuum. The crude product was purified by silica gel flash column chromatography (2:3 EtOAc/hexane) to give the 5"-deoxy fluoro derivative (22 mg, 50%).

[α]$_D$+37.37° (c 0.8, CHCl$_3$); R$_f$ 0.54 (1:1 EtOAc/hexane); $^{19}$F NMR (400 MHz, CDCl$_3$) Φ 237.4-237.6 (m, F-5); LCMS calcd for C$_{105}$H$_{98}$FN$_5$O$_{28}$ (M+H$^+$) 1896.64. found 1896.8.

To a solution of the 5"-deoxy fluoro derivative (18 mg, 0.0095 mmol) in dry MeOH (2 mL) was treated with a catalytic amount of NaOMe in dry MeOH (1 mL, pH 8-9) and stirred at room temperature for 3 hours to completion of reaction. The reaction mixture was neutralized by addition of dry-ice, and the solvent was evaporated to dryness under vacuum. The crude product which was purified by silica gel flash column chromatography (1:19 MeOH/CH$_2$Cl$_2$) to give Compound 60 (12 mg, 92%).

[α]$_D$+18.0° (c 0.6, MeOH); R$_f$ 0.47 (1:19 MeOH/CH$_2$Cl$_2$); LCMS calcd for C$_{70}$H$_{78}$FN$_5$O$_{23}$ (M+H$^+$) 1376.51. found 1377.0.

Example 87

5"-deoxy-5"-fluoro paromomycin (61)

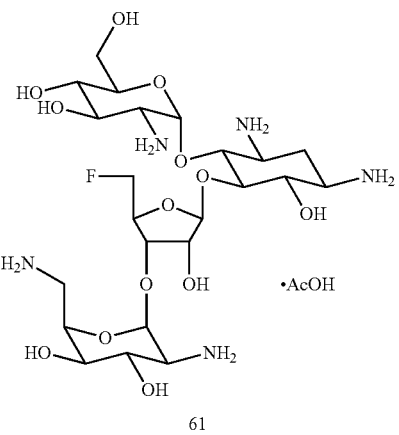

Compound 60 (12 mg, 0.0087 mmol) was dissolved in AcOH—H$_2$O (4:1, 3 mL) and heated at 60° C. for 2 hours to completion of reaction. The solvent was removed under reduced pressure and the crude material was used in the next step for hydrogenolysis without further purification.

LCMS calcd for C$_{63}$H$_{74}$FN$_5$O$_{23}$ (M+H$^+$) 1288.48. found 1288.6.

To a solution of above crude material in MeOH—H$_2$O (1:1, 2 mL) was added 20% palladium hydroxide on carbon and the suspension was stirred at room temperature overnight under an atmosphere of hydrogen (hydrogen balloon). The mixture was filtered through a layer of Celite, concentrated under vacuum. The residue was dissolved in AcOH—H$_2$O (2:1, 0.5 mL) and lyophilized to give Compound 61 (2.6 mg, 68%) as a white solid.

[α]$_D$+33.07° (c 0.26, H$_2$O); $^1$H NMR (400 MHz, D$_2$O) δ 5.57 (s, 1H), 5.30 (s, 1H), 5.17 (s, 1H), 4.54-4.42 (m, 2H), 4.30-4.21 (m, 4H), 4.21-4.17 (m, 2H), 4.07-3.91 (m, 2H), 3.82-3.61 (m, 5H), 3.6-3.54 (m, 1H), 3.49-3.40 (m, 2H), 3.38-3.16 (m, 4H), 2.38-2.22 (m, 1H), 1.82 (s, 15H), 1.70-1.60 (m, 1H); $^{13}$C NMR (125 MHz, D$_2$O) δ 182.1, 111.1, 96.8, 96.3, 85.6, 81.7, 80.4, 75.2, 74.2, 73.9, 73.6, 73.4, 71.0, 70.3, 69.9, 68.5, 68.0, 61.0, 54.7, 51.5, 50.8, 49.7, 41.0, 30.9, 23.9; LCMS calcd for C$_{23}$H$_{44}$FN$_5$O$_{13}$ (M+H$^+$) 618.29. found 618.4.

Example 88

4',6'-O-benzylidene-penta-O-tert-butyldimethylsilanyloxy-penta-N-benzyloxycarbonyl paromomycin (62)

2 ⟶

-continued

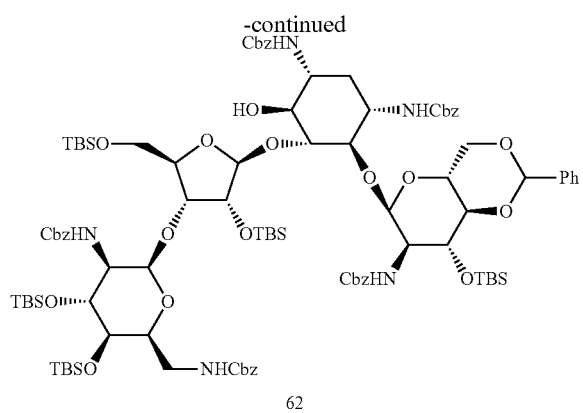

62

To a stirred solution of Compound 2 (1.35 g, 0.98 mmol) in dry dichloromethane (20 mL) was added 2,4,6-collidine (1.07 g, 8.82 mmol) and TBDMSOTf (1.811 g, 6.86 mmol) at 0° C. Then the reaction mixture was slowly brought to room temperature and stirred for 12 hours. Few drops of water were added to quench the excess TBSOTf and the mixture was extracted with dichloromethane. The organic layer was washed with brine, dried over anhydrous $Na_2SO_4$ and concentrated. The corresponding crude product was purified by silica gel flash column chromatography to give Compound 62 (1.048 g, 55%).

$[\alpha]_D = +16°$ (c 0.6, $CHCl_3$). ESI/MS calcd for $C_{100}H_{149}N_5O_{24}Si_5$ (M+H$^+$) 1944.94. found 1946.

Example 89

Synthesis of the Cyclic Arbamate (63)

62 →

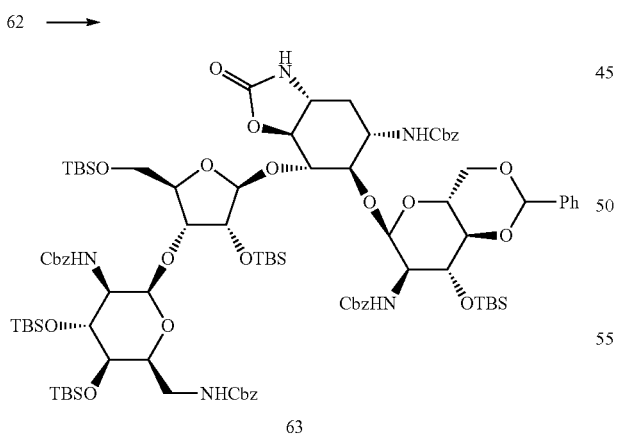

63

To a stirred solution of Compound 62 (330 mg, 0.17 mmol) in dry DMF (6 mL) was added 60% NaH in mineral oil (8 mg) at 0° C. with stirring continued 6 hours at 0° C. A few drops of saturated ammonium chloride solution were added, followed by extraction with ethyl acetate. The organic layer was washed with brine, dried over anhydrous $Na_2SO_4$ and concentrated. The corresponding crude product was purified by silica gel flash column chromatography to give Compound 63 (180 mg, 58%) and 120 mg (36%) of starting material, Compound 62.

$[\alpha]_D = +18°$ (c 0.5, $CHCl_3$). ESI/MS calcd for $C_{93}H_{141}N_5O_{23}Si_5$ (M+H$^+$) 1836.89. found 1837.6

Example 90

4',6'-O-benzylidene-penta-O-tert-butyldimethylsilanyloxy-tetra-N-benzyloxycarbonyl paromomycin (64)

63 →

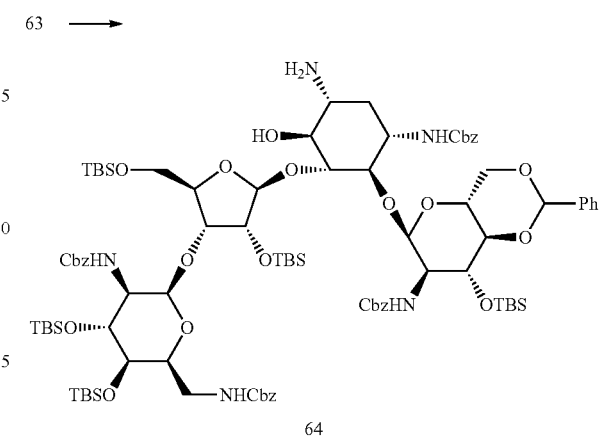

64

To a solution of Compound 63 (190 mg, 0.1 mmol) in DMF (7 mL) was added 0.7 mL of aqueous LiOH (9 mg, 0.21 mmol) with stirring continued for additional 3 hours at room temperature. A few drops of saturated ammonium chloride solution was added, followed by extraction with ethyl acetate. The organic layer was washed with brine, dried over anhydrous $Na_2SO_4$ and concentrated. The corresponding crude product was purified by silica gel flash column chromatography to give Compound 64 (100 mg, 53%) and 50 mg (26%) of starting material, Compound 63.

$[\alpha]_D = +13°$ (c 0.3 $CHCl_3$) ESI/MS calcd for $C_{92}H_{143}N_5O_{22}Si_5$ (M+H$^+$) 1810.91. found 1811.3.

Example 91

4',6'-O-benzylidene-penta-O-tert-butyldimethylsilanyloxy-tetra-N-benzyloxycarbonyl-N-1-haba paromomycin (65)

64 →

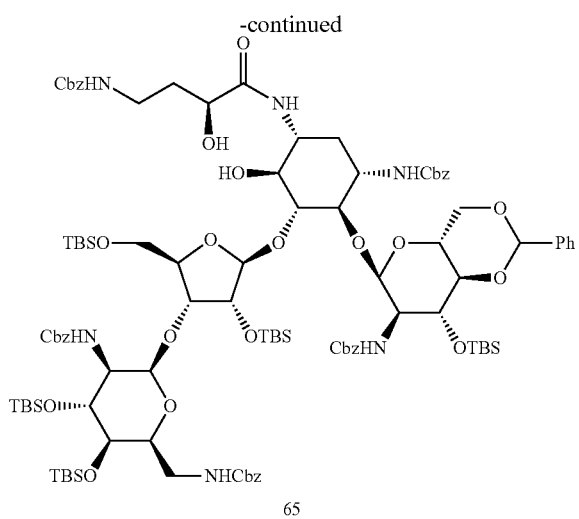

65

To a stirred solution of benzyloxy 4-hydroxy aminobutric acid (27 mg, 0.11 mmol) and N-hydroxy succinimide (12 mg, 0.11 mmol) in dry THF (2 mL) was added DCC (22 mg, 0.11 mmol) with stirring continued for 1 hour at room temperature. To this mixture Compound 64 (95 mg, 0.053 mmol) in dry THF (2 mL) and triethyl amine (15 μL, 0.11 mmol) was added and stirred for 12 hours at room temperature. Evaporation of the solvent followed by purification by silica gel flash column chromatography gave Compound 65 (80 mg, 74%).

$[\alpha]_D = +19°$ (c 0.4, CHCl$_3$).

Example 92

4',6'-O-benzylidene-tetra-N-benzyloxycarbonyl-N-1-haba paromomycin (66)

65 ⟶

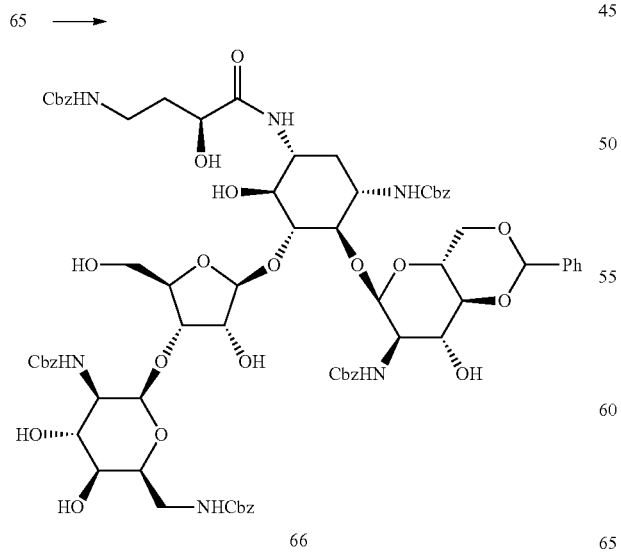

66

Compound 65 (90 mg, 0.044 mmol) was dissolved in dry pyridine (2 mL), HF.Py (2 mL) was added at 0° C. and the reaction was slowly brought to room temperature and stirred for 2 days. Water was added and the reaction mixture was extracted with ethyl acetate. The organic layers were washed with brine and dried over Na$_2$SO$_4$ Evaporation of the solvent gave the crude material which was purified by column chromatography to give Compound 66 (50 mg, 77%).

$[\alpha]_D = +20°$ (c 0.6, CHCl$_3$). ESI/MS calcd for C$_{74}$H$_{86}$N$_6$O$_{26}$ (M+H$^+$); 1475.56. found 1475.7.

Example 93

N-1-haba paromomycin (67)

66 ⟶

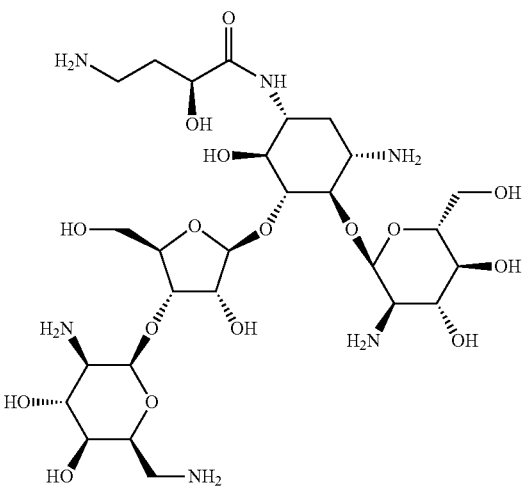

67

Compound 66 (29 mg, 0.019 mmol) was stirred in 4 mL of acetic acid/water mixture (4:1) at room temperature for 12 hours and then for an additional 6 hours at 55° C. To this reaction mixture 20% Pd(OH)$_2$ (29 mg) was added under an atmosphere of hydrogen (balloon) with stirring for 3 hours. The mixture was filtered over celite and lypholized to give the Compound 67 (20 mg, 99%).

$[\alpha]_D = +14.5°$ (c 0.2, H$_2$O). $^1$H NMR (400 MHz, D$_2$O) δ 5.84 (s, 1H), 5.44 (s, 1H), 5.21 (s, 1H), 5.35 (s, 1H), 4.61 (bs, 1H), 4.49-3.4 (m, 24H), 2.26-2.11 (m, 2H), 1.8-1.7 (m, 2H); HRMS calcd for C$_{27}$H$_{52}$N$_6$O$_{16}$ (M+H$^+$): 717.34398. found: 717.35175.

Example 94
Synthesis of 2″-O- and 6′-N-Side Chain Paromomycin Analogs
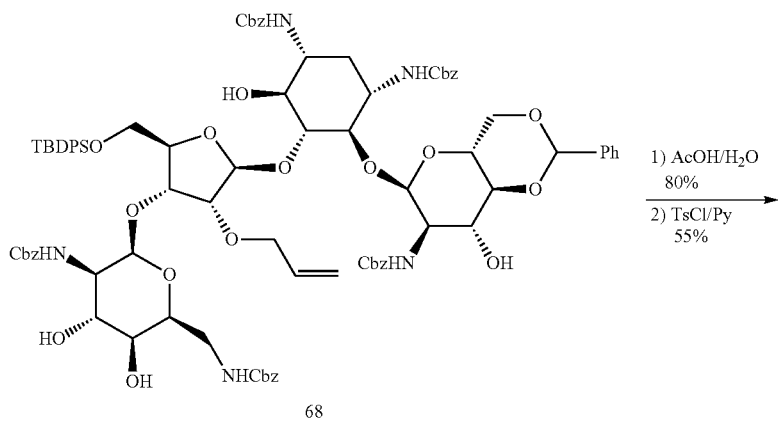
68
1) AcOH/H$_2$O 80%
2) TsCl/Py 55%
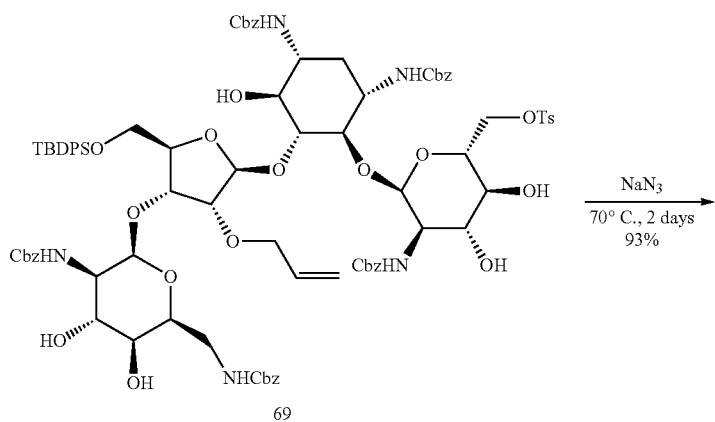
69
NaN$_3$
70° C., 2 days
93%
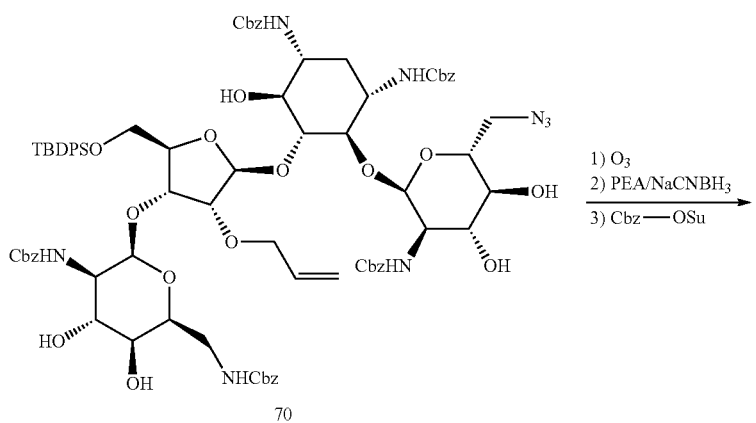
70
1) O$_3$
2) PEA/NaCNBH$_3$
3) Cbz—OSu

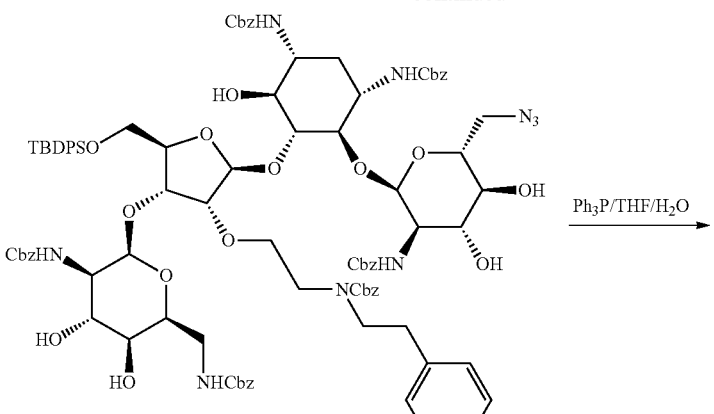
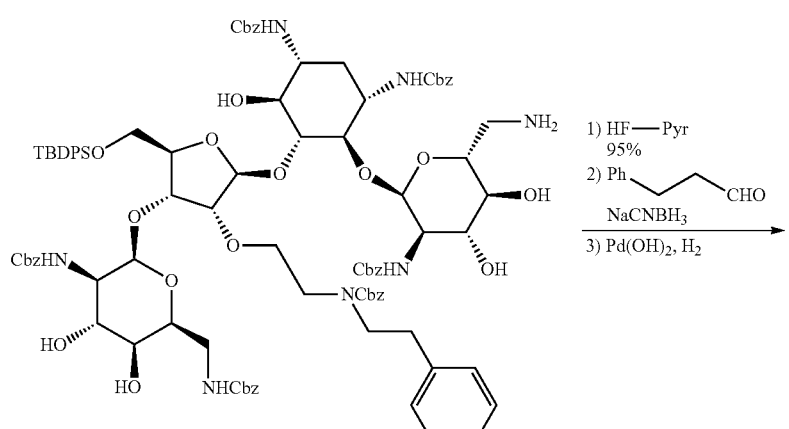
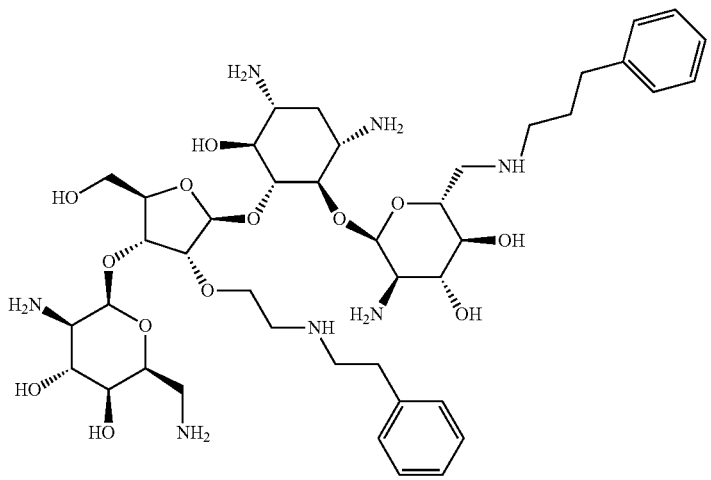

-continued
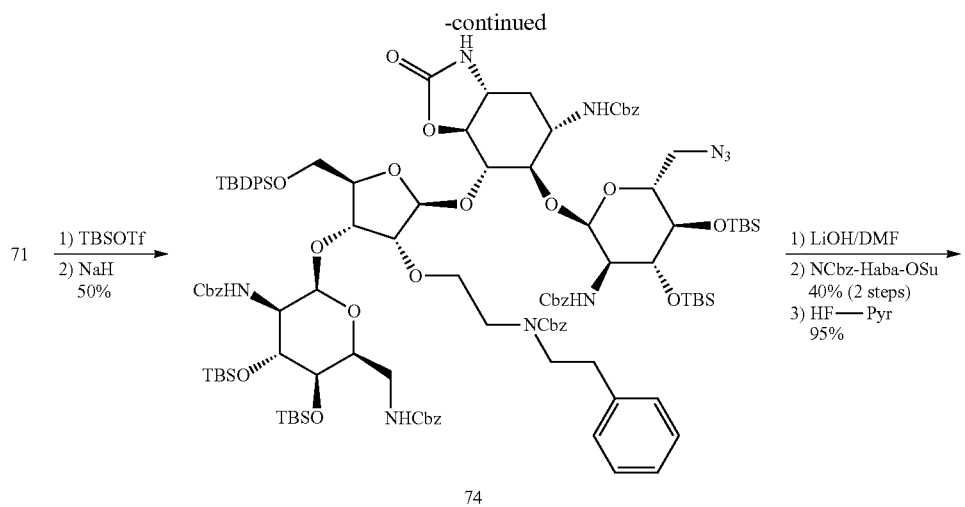
74
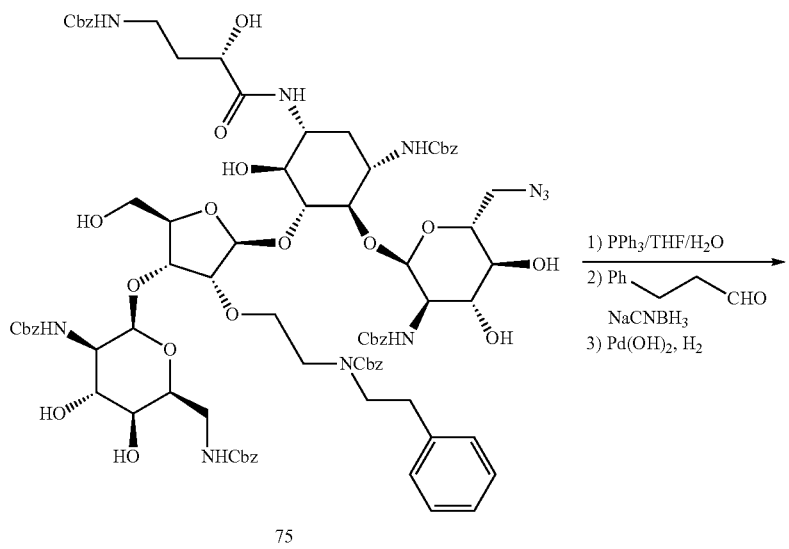
75
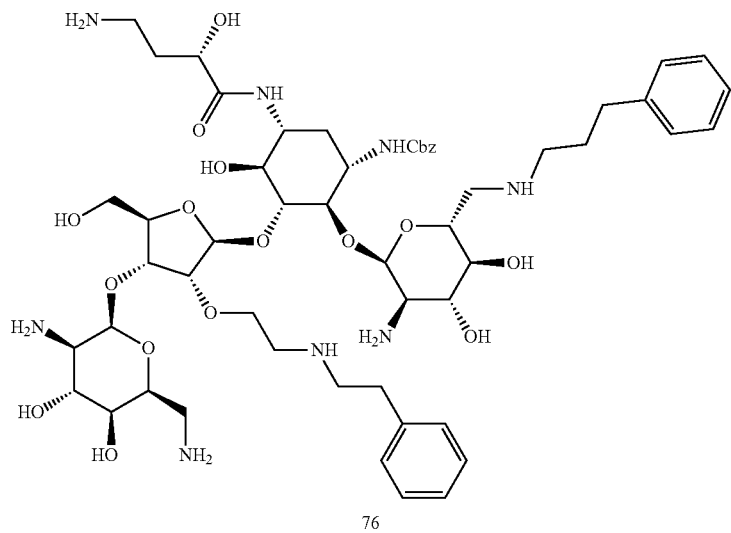
76

Starting with Compound 68 (the TBDPS protected version of Compound 4 prepared according to Examples 2-3 using TBDPS-OTf instead of TBDMS-OTf), 2"-O- and 6'-N-modified Paromomycin analogs 73 (2'-O-phenylethylaminoethyl-6'-phenylpropyl neomycin) and 76 (N-1-haba-2"-O-phenylethylaminoethyl-6'-phenylpropyl neomycin) were prepared with and without the 1-HABA group. 3'-4' dideoxy analogs (on ring I) are prepared by similar means starting from Compound 31 in Example 61. The synthetic methods illustrated in this example and in combination with other examples, particularly Examples 1-44, enable the preparation of a plurality of diverse di and tri-substituted Paromomycin analogs. Numerous modifications known in the chemical arts are amenable to the synthetic methods disclosed herein to enable even further diverse Paromomycin analogs.

Example 95

Synthesis of Paromomycin Analogs Substituted at the 1, 2" and 5" Positions

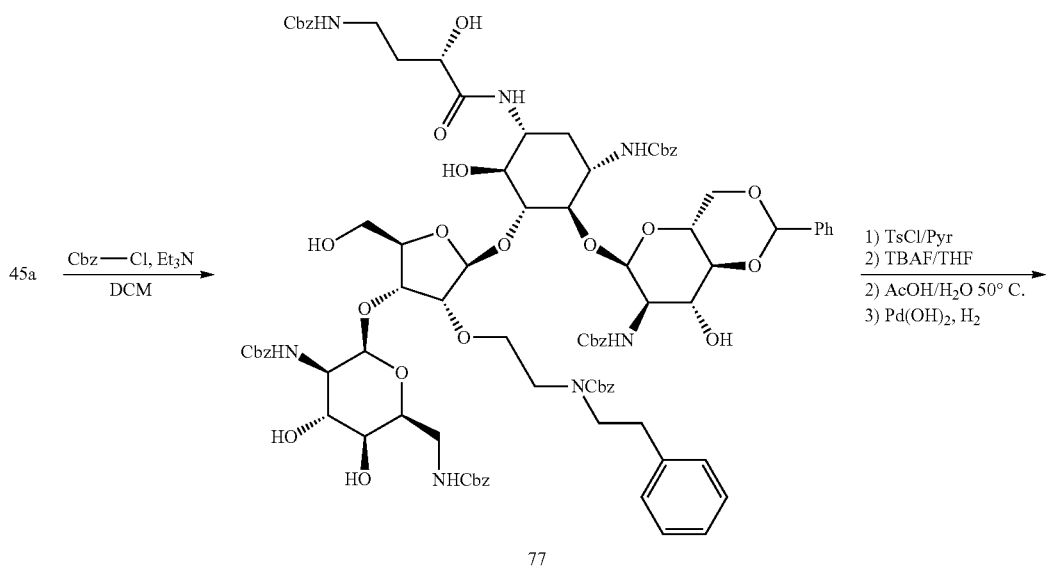

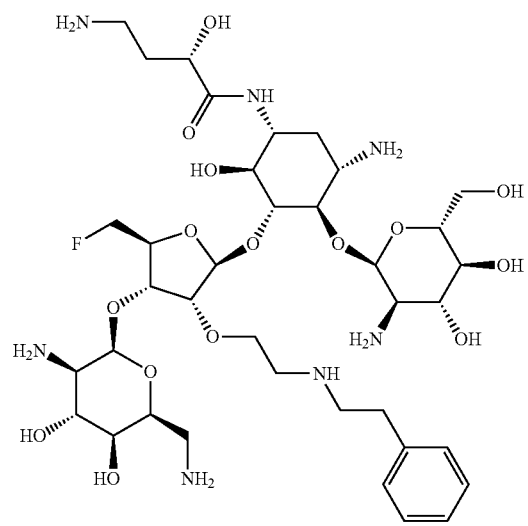

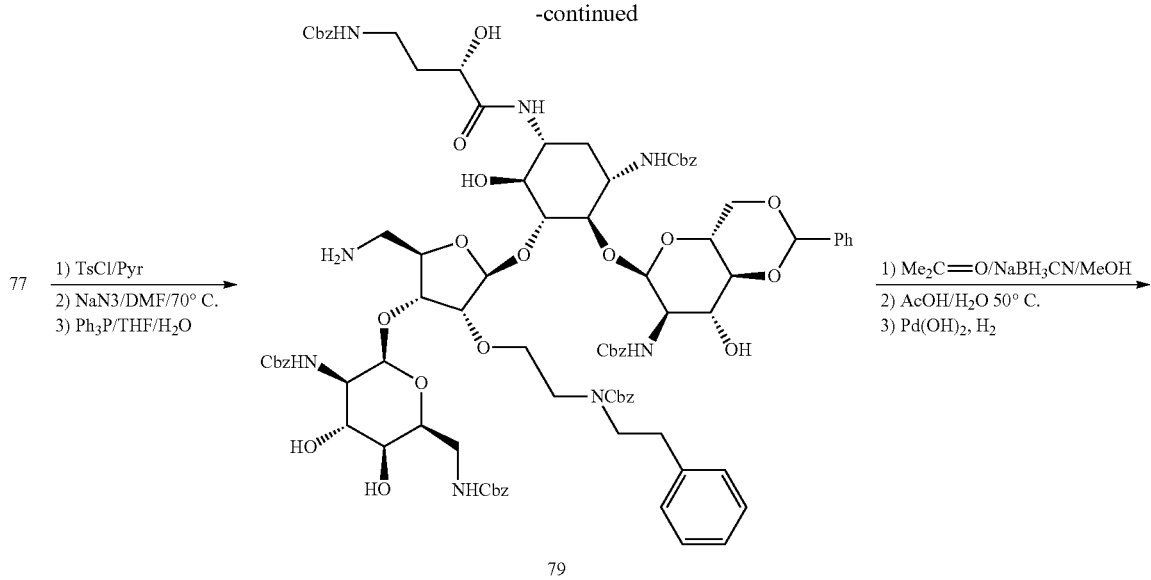

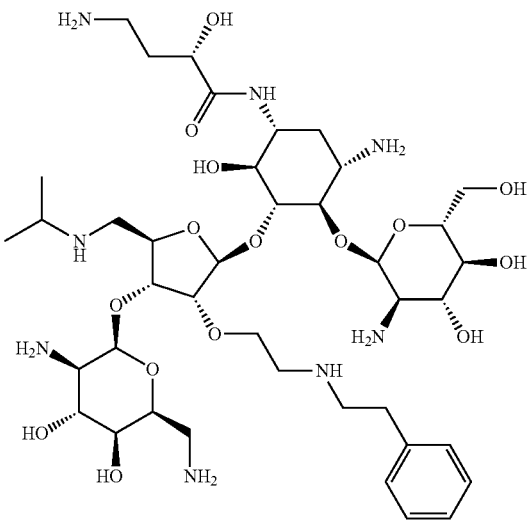

Paromomycin analogs substituted at the 1, 2″ and the 5″ positions, such as N-1-haba-2″-O-phenylethylaminoethyl-5″-fluoro paromomycin (Compound 78) and N-1-haba-2″-O-phenylethylaminoethyl-5″-isopropylamino paromomycin (Compound 80), are prepared following the synthetic methods illustrated herein and particularly Examples 1-13, 61-77, 78-84 and 86-87. Substitution in this pattern without N-1 substitution can be achieved by starting with compounds 8, then removing the TBS group with AcOH, and continuing as shown in this example. 3′-4′ dideoxy analogs (on ring I) are prepared by similar means starting from compound 31 in Example 61. Numerous modifications known in the chemical arts, such as for example variation of chemical functional groups or reaction conditions, are amenable to the synthetic methods disclosed herein. Such modifications are intended to be included in the present invention and will enable even further diverse Paromomycin analogs.

Example 96
Synthesis of Paromomycin Analogs Substituted at the 1, 6' and 5" Positions
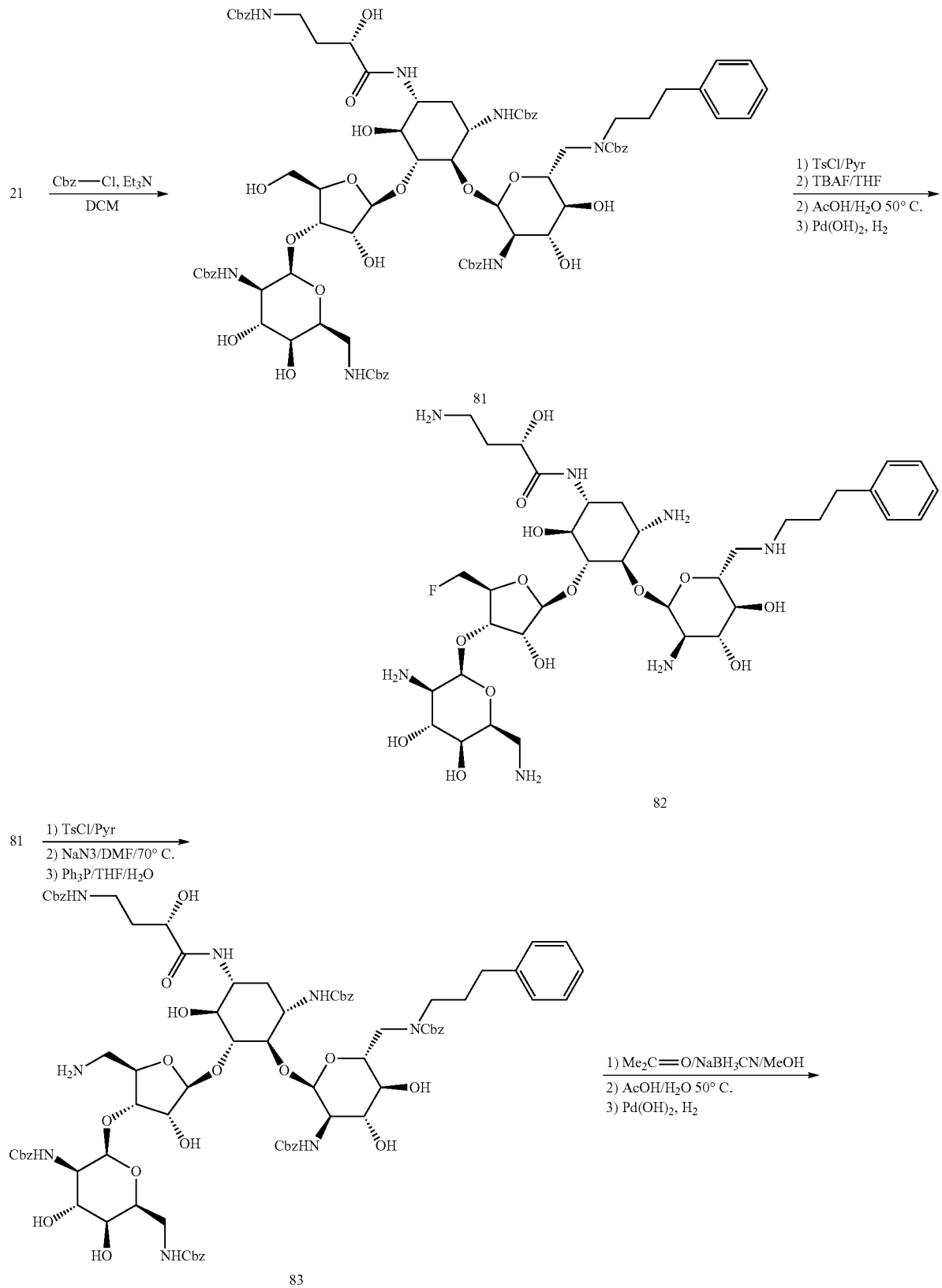

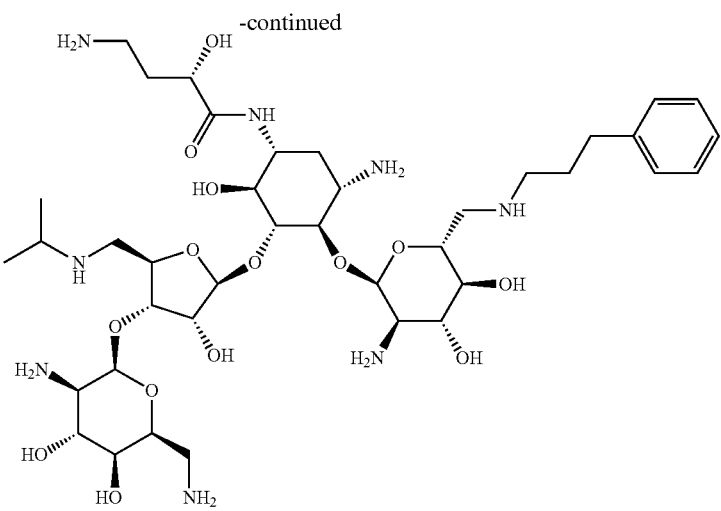

84

Paromomycin analogs substituted at the 6' and the 5" positions with or without N-1 substitution, such as N-1-haba-6'-phenylpropyl-5"-fluoro neomycin (Compound 82) and N-1-haba-6'-phenylpropyl-5"-isopropylamino neomycin (Compound 84), are prepared following the synthetic methods illustrated herein and particularly Examples 14-44, 78-84 and 86-87. 3'-4' dideoxy analogs (on ring 1) are prepared by similar means starting from Compound 31 in Example 61. Numerous modifications known in the chemical arts, such as for example variation of chemical functional groups or reaction conditions, are amenable to the synthetic methods disclosed herein. Such modifications are intended to be included in the present invention and will enable even further diverse Paromomycin analogs.

Example 97

Synthesis of N-1-haba-2"-O-phenylethylaminoethyl-3',4'-dideoxy neomycin (87)

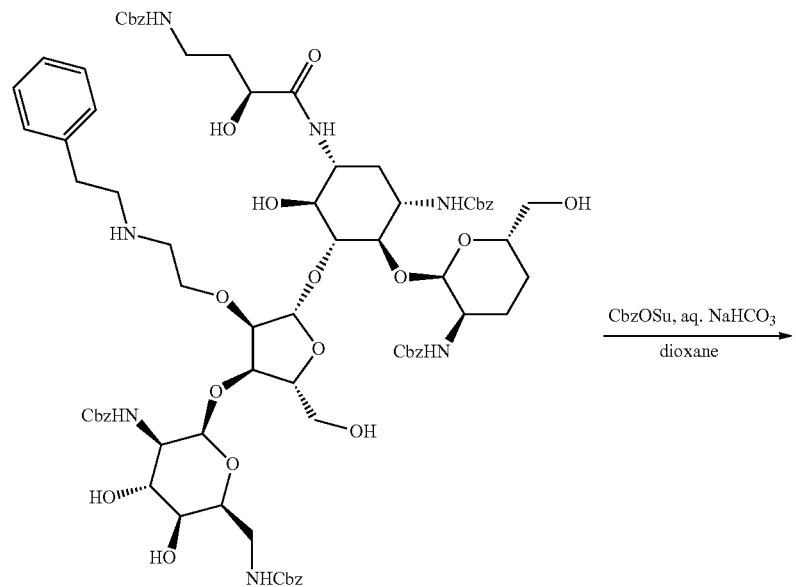

38

-continued
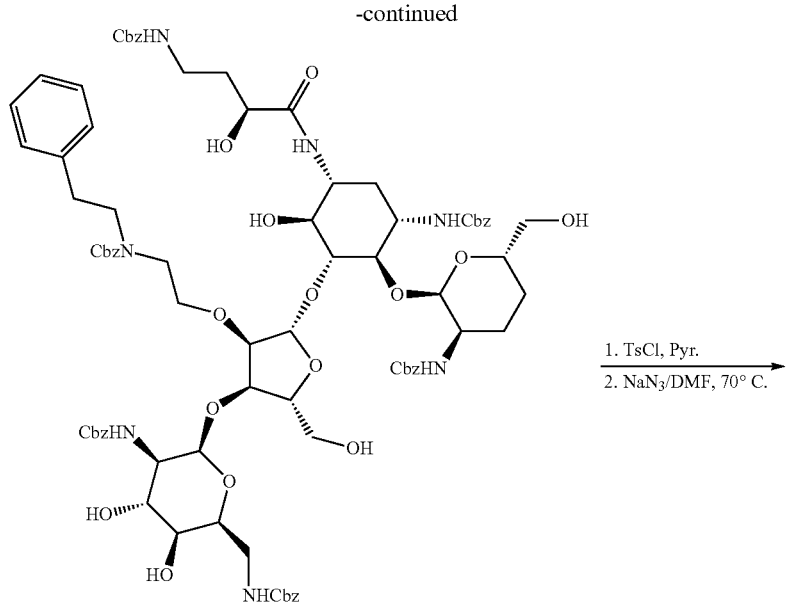
85
1. TsCl, Pyr.
2. NaN₃/DMF, 70° C.
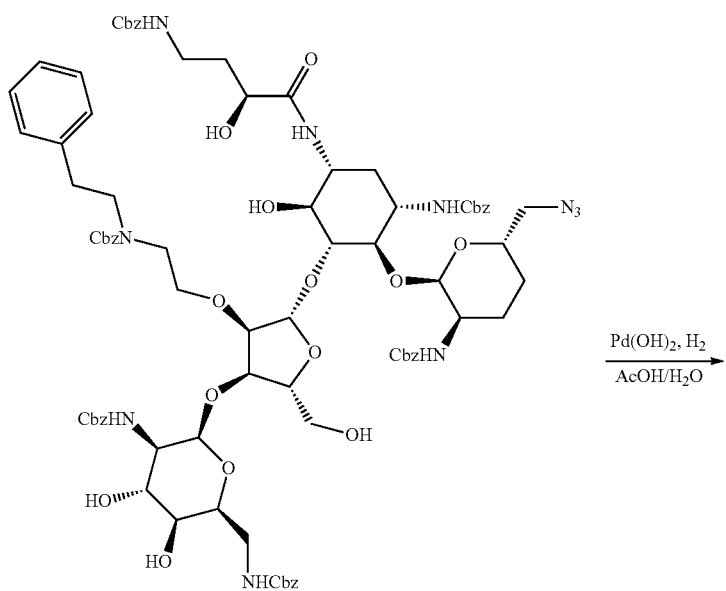
86
Pd(OH)₂, H₂
─────────────
AcOH/H₂O -continued

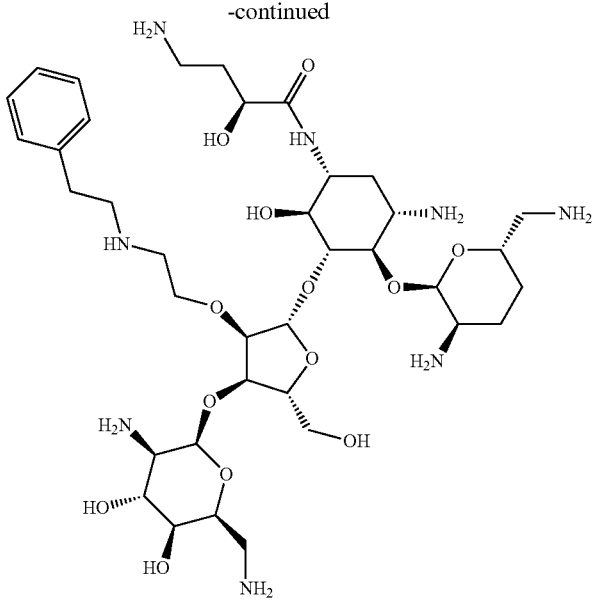

87

To a stirred solution of 38 (100 mg, 0.067 mmol) and CbzOSu (33 mg, 0.133 mmol) in dioxane (10 mL) was added aqueous saturated $NaHCO_3$ (5 mL) and continued to stir for 6 h. Saturated ammonium chloride solution was added, followed by extraction with ethyl acetate. The organic layer was washed with saturated brine and dried over anhydrous $Na_2SO_4$, followed by concentration of the solvent yielded the corresponding crude product. The crude material was purified by flash column chromatography to yield pure 85 (61 mg, 56%). ESI/MS calcd for $C_{85}H_{101}N_7O_{26}$ (M+H$^+$): 1636.74. found: 1636.7.

To a stirred solution of 85 (60 mg, 0.037 mmol) in pyridine (5 mL) was added TsCl (9 mg, 0.046) and continued to stir overnight. Few drops of water were added, followed by extraction with ethyl acetate. The organic layer was washed with saturated $CuSO_4$ solution, brine and dried over anhydrous $Na_2SO_4$, followed by concentration of the solvent yielded the corresponding crude product. This crude material in dry DMF was added $NaN_3$ (24 mg, 0.37 mmol) and heated at 70° C. for 12 h. Few drops of saturated ammonium chloride were added, followed by extraction with ethyl acetate. The organic layer was washed with water, brine and dried over anhydrous $Na_2SO_4$, followed by concentration of the solvent yielded the corresponding crude product. This material was purified by flash column chromatography to yield the pure 86 (21 mg, 34%). In addition to the product, some regioisomeric product (15 mg, 24%) and starting free hydroxyl compound (10 mg) were isolated. ESI/MS calcd for $C_{85}H_{100}N_{10}O_{25}$ (M+H$^+$): 1661.76. found: 1661.9.

To a stirred solution of 86 (20 mg, 0.012 mmol) in 2 mL of acetic acid/water mixture (4:1) and 0.5 mL of methanol was added 20% $Pd(OH)_2$ (20 mg) at room temperature and stirred for 6 h under hydrogen atmosphere (balloon). Then filtered over celite and lypholized to give 87 as acetate salt (14 mg, 93%). $[\alpha]_D$=+27.1° (c 0.2, $H_2O$). $^1$H NMR (400 MHz, $D_2O$) δ 7.4-7.1 (m, 5H), 5.5 (s, 1H), 5.28 (s, 1H), 5.08 (s, 1H), 4.5-4.4 (m, 1H), 4.2-4.0 (m, 5H), 3.9-3.6 (m, 9H), 3.5-3.1 (m, 11H), 3.0-2.8 (m, 5H), 2.1-1.4 (m, 8H); ESI/MS calcd for $C_{37}H_{66}N_8O_{13}$ (M+H$^+$): 830.47493. found: 830.48221.

Example 98

Synthesis of Paromomycin Analogs Substituted at the 1 and 5" Positions

Paromomycin analogs substituted at the 1' and the 5" positions are prepared following the synthetic methods illustrated herein and particularly Examples 45-59, 61-77, 78-84, 86-87 and 89-93. 3'-4' dideoxy analogs (on ring I) are prepared by similar means starting from Compound 31 in Example 61. Numerous modifications known in the chemical arts, such as for example variation of chemical functional groups or reaction conditions, are amenable to the synthetic methods disclosed herein. Such modifications are intended to be included in the present invention and will enable even further diverse Paromomycin analogs.

Example 99

Synthesis of Paromomycin Analogs Substituted at the 6 and 2" Positions

Paromomycin analogs substituted at the 6' and the 6 positions are prepared following the synthetic methods illustrated herein and particularly Examples 1-13, 53-59 and 61-77. 3'-4' dideoxy analogs (on ring I) are prepared by similar means starting from Compound 31 in Example 61. Numerous modifications known in the chemical arts, such as for example variation of chemical functional groups or reaction conditions, are amenable to the synthetic methods disclosed herein. Such modifications are intended to be included in the present invention and will enable even further diverse Paromomycin analogs.

Example 100

Synthesis of Paromomycin Analogs Substituted at the 6 and 5" Positions

Paromomycin analogs substituted at the 6 and the 5" positions are prepared following the synthetic methods illustrated

139 herein and particularly Examples 53-59, 78-84 and 86-87. 3'-4' dideoxy analogs (on ring I) are prepared by similar means starting from Compound 31 in Example 61. Numerous modifications known in the chemical arts, such as for example variation of chemical functional groups or reaction conditions, are amenable to the synthetic methods disclosed herein. Such modifications are intended to be included in the present invention and will enable even further diverse Paromomycin analogs.

Example 101

Synthesis of Paromomycin Analogs Substituted at the 6' and 6 Positions

Paromomycin analogs substituted at the 6' and the 6 positions are prepared following the synthetic methods illustrated herein and particularly Examples 14-44 and 53-59. 3'-4' dideoxy analogs (on ring I) are prepared by similar means starting from Compound 31 in Example 61. Numerous modifications known in the chemical arts, such as for example variation of chemical functional groups or reaction conditions, are amenable to the synthetic methods disclosed herein. Such modifications are intended to be included in the present invention and will enable even further diverse Paromomycin analogs.

Example 102

Coupled Bacterial Transcription/Translation Assay

The DNA template, pBestLuc™ (Promega), is a plasmid containing a reporter gene for firefly luciferase fused to a strong tac promoter and ribosome binding site. Messenger RNA from 1 µg pBestLuc is transcribed and translated in *E. coli* S30 bacterial extract in the presence or absence of test compound. Compounds are tested in a black 96 well microtiter plate with an assay volume of 35 µL. Each test well contains: 5 µL test compound, 13 µL S30 premix (Promega), 4 µL 10× complete amino acid mix (1 mM each), 5 µL *E. coli* S30 extract and 8 µL of 0.125 µg/µL pBestLuc™. The transcription/translation reaction is incubated for 35 minutes at 37° C. followed by detection of functional luciferase with the addition of 30 µL LucLite™ (Packard). Light output is quantitated on a Packard TopCount.

Example 103

Mass Spectrometry Based Binding Asay

Screening was performed by measuring the formation of non-covalent complexes between a single ligand or ligand mixture and the appropriate RNA target, such as for example the 16S Kd and 18S Kd ribosomal subunits, along with suitable control structured RNA target(s) simultaneously using a 9.4 T FT-ICR mass spectrometer as detector. Full experimental details of the assay for have been described in related literature (Sannes-Lowery, et al. in *TrAC, Trends Anal. Chem.* 2000, 19, 481-491; Sannes-Lowery, et al. in *Anal. Biochem.* 2000, 280, 264-271; and Griffey, R. H.; Sannes-Lowery, K. A.; Drader, J. J.; Mohan, V.; Swayze, E. E. et al. Characterization of Low Affinity Complexes Between RNA and Small Molecules Using Electrospray Ionization Mass Spectrometry. *J. Am. Chem. Soc.* 2000, 122, 9933-9938).

In a typical experiment, 10 µL of an aqueous solution containing 100 mM ammonium acetate buffer, 2.5 or 5 µM of each RNA, and 33% isopropyl alcohol (to aid ion desolvation) was prepared with different concentrations of each ligand or ligand mixture Samples were introduced into the electrospray ionization source (negative ionization mode) at 1 µL/min and ions were stored for 1 sec in an RF-only hexapole following desolvation. The abundances were integrated from the respective ions for free RNA and the ligand-RNA complex. The primary (1:1 RNA:ligand) and secondary (1:2 complex, if observed). KD values were determined by titrating a single ligand through a concentration range of 0.25-25 µM with an RNA target concentration of 0.10 µM. The peak ratios were measured at each concentration, then a plot of complex/free RNA versus concentration of ligand added was fitted to a second (or higher) order binding polynomial to determine the KD.

Example 104

In Vitro Antibacterial Activity Determination of Minimum Inhibitory Concentrations (MICs)

The MIC assays are carried out in 150 µL volume in duplicate in 96-well clear flat-bottom plates. The bacterial suspension from an overnight culture growth in appropriate medium is added to a solution of test compound in 4% DMSO in water. Final bacterial inoculum is approximately $10^5$-$10^6$ CFU/well. The percent growth of the bacteria in test wells relative to that observed for a well containing no compound is determined by measuring absorbance at 595 nm ($A_{595}$) after 24 h. The MIC is determined as a range of single compound where the complete inhibition of growth is observed at the higher concentration and cells are viable at the lower concentrations. Both ampicillin and tetracycline are used as antibiotic-positive controls in each screening assay for *S. pyogenes, E. coli* imp-, *E. coli, S. aureus, E. faecalis, K. pneumoniae* and *P. vulgaris*. Ciprofloxacin is used as an antibiotic positive control in each screening assay for *P. aeruginosa*.

Example 105

Representative Aminoglycoside Compounds

The following compounds were prepared using methods illustrated in the previous examples. The compounds were analyzed for their activity using FTICR mass spectrometry (for 16S Kd, run at 100 nM RNA, except those marked with an asterisk were run at 500 nM RNA) and a bacterial transcription/translation assay, such as described herein. The compounds were also examined in standard bacterial assays against *E. Coli* and *S. Aureus* to determine activities. Data marked with "*b*"-- initially tested MIC<1.5 uM, but retested higher.

| Compound# | 18S Kd (uM) | 16S Kd (uM) | Trans/Trans IC50 (uM) | MIC (uM) | |
|---|---|---|---|---|---|
| | | | | E. Coli. | S. Aureus |
| 9h | NA | 9.2 | 1.0 | >50 | 25-50 |
| 9i | NA | 1.3 | 0.2 | 25-50 | 2-3 |
| 9g | NA | 0.9* | 0.2 | 12-52 | 6-12 |
| 9c | NA | 0.4* | 0.3 | 25-50 | 3-6 |
| 9f | NA | 0.3 | 0.4 | 12-25 | 2-3 |
| 9d | NA | 0.7 | 0.3 | 6-12 | 2-3 |
| 61 | NA | 1.1 | 0.3 | >50 | 12-25 |
| 13 | NA | 2.7 | 0.3 | 25-50 | 3-6 |
| 14a | NA | 3.8 | 0.3 | >50 | 6-12 |
| 30a | 58 | 19 | 0.2 | 6-12 | 12-25 |
| 30b | 18 | 9.2 | 0.1 | 6-12 | 6-12 |

-continued

| Compound# | 18S Kd (uM) | 16S Kd (uM) | Trans/Trans IC50 (uM) | MIC (uM) E. Coli. | S. Aureus |
|---|---|---|---|---|---|
| 12a | 7.3 | 0.9 | 0.1 | 12-25 | 6-12 |
| 9j | 5.0 | 0.1 | 0.1 | 1.5-3 | 3-6 |
| 9k | 2.6 | 0.3 | 0.04 | 1.5-3 | 3-6 |
| 54 | 68 | 4.1 | 0.3 | 6-12 | 25-50 |
| 9e | 11 | 3.9 | 0.2 | >100 | >100 |
| 9a | 3.5 | 0.6 | 0.1 | 3-6[b] | 0.6-1 |
| 9b | 9.4 | 0.9 | 0.1 | 6-12[b] | 0.6-1 |
| 9m | 0.9 | 0.1 | 0.1 | 12-25 | 1-2 |
| 9n | 0.4 | 0.1 | 0.2 | 3-6 | 3-5 |
| 9l | NA | NA | 0.1 | 50-100 | 6-12 |
| 9t | 0.3 | 0.02 | 0.7 | 6-12 | 0.6-1 |
| 9r | 1.8 | 0.6 | 0.3 | 12-25 | 2-3 |
| 9o | 1.0 | 0.2 | 0.2 | 6-12 | 0.6-1 |
| 9p | 1.3 | 0.1 | 1.1 | 3-6 | 0.3-0.6 |
| 9q | 0.3 | 0.1 | 0.8 | 3-6 | 3-5 |
| 9s | 0.5 | 0.1 | 0.2 | 3-6 | 0.3-0.6 |
| 9u | 22 | 5 | 0.4 | 12-25 | 1-2 |
| 9x | 6.3 | 1.0 | 0.1 | 3-5 | 0.6-1.2 |
| 9z | 6.4 | 0.7 | 0.1 | 3-5 | 0.6-1.2 |
| 14c | 59 | 40 | 0.2 | 10-20 | 3-5 |
| 9ak | 3.5 | 0.7 | 0.3 | 10-20 | 1-3. |

Example 106

Representative Aminoglycoside Compounds

The following compounds were prepared using methods illustrated in the previous examples. The compounds were analyzed for their activity using FTICR mass spectrometry and a bacterial transcription/translation assay, such as described herein. The compounds were also examined in standard bacterial assays against E. Coli and S. Aureus to determine activities.

| Compound# | 18S Kd (uM) | 16S Kd (uM) | Trans/Trans IC50 (uM) | MIC (uM) E. Coli. | S. Aureus |
|---|---|---|---|---|---|
| paromomycin | 4.8 | 0.6 | 0.1 | 20-40 | 3-5 |
| 9y | NA | NA | 0.2 | 10-20 | 5-10 |
| 9aa | 3.5 | 0.9 | 1.5 | 20-40 | 5-10 |
| 9v | 5.8 | 2.5 | 0.3 | 10-20 | 0.6-1 |
| 9w | 1.7 | 3.2 | 0.4 | 20-40 | 1-3 |
| 11 | 6.1 | 1.5 | 0.4 | 10-20 | 1-3 |
| 10 | 2.5 | 3.9 | 0.4 | 10-20 | 3-5 |

Neomycin B was also tested in the assays described. The 16S and 18S Kd were 0.04 and 0.3 µM, respectively. The Trans/Trans IC50 was 0.2 µM, and the MIC for E. Coli and S. Aureus were 1.3-2.5 and 0.6-1.3, respectively.

Example 107

Representative Aminoglycoside Compounds

The following compounds were prepared using methods illustrated in the previous examples. The compounds were examined in standard bacterial assays against E. Coli and S. Aureus to determine activities. If present, "N.D." indicates "no data".

| Compound# | MIC (uM) E. Coli. | S. Aureus |
|---|---|---|
| 9ac | >10 | 1.3-2.5 |
| 9ab | >10 | 5-10 |
| 9ad | >10 | 2.5-5 |
| 9ae | N.D. | N.D. |
| 9af | >10 | 2.5-5 |
| 9ah | 5-10 | 0.6-1.2 |
| 67 | 5-10 | 1.3-2.5 |
| 12b | 20-40 | 5-10 |
| 14b | 20-40 | 3-5 |
| 14c | 10-20 | 3-5 |
| 30c | >100 | 12-25 |

Example 108

Representative Aminoglycoside Compounds

The following compounds were prepared using methods illustrated in the previous examples. The compounds were analyzed for their activity using FTICR mass spectrometry and a bacterial transcription/translation assay, such as described herein. The compounds were also examined in standard bacterial assays against E. Coli and S. Aureus to determine activities.

| Compound# | 18S Kd (uM) | 16S Kd (uM) | Trans/Trans IC50 (uM) | MIC (uM) E. Coli. | S. Aureus |
|---|---|---|---|---|---|
| 15d | 1.4 | 0.01 | 0.3 | 6-12 | 12-25 |
| 15a | 0.7 | 0.6 | 0.3 | 3-6 | 2-3 |
| 15e | 1.2 | 0.4 | 0.2 | 2-3 | 2-3 |
| 15i | 1.7 | 0.6 | 0.2 | 12-25 | 3-6 |
| 15h | 1.2 | 1.2 | 0.2 | 2.5-5 | 1.3-2.5 |
| 15b | 1.4 | 1.6 | 0.2 | 2.5-5 | 1.3-2.5 |
| 15f | 6.0 | 6.3 | 0.0 | 2.5-5 | 10-20 |
| 15j | 2.2 | 0.5 | 0.2 | 1.3-2.5 | 0.3-0.6 |
| 15c | 3.0 | 3.6 | 0.3 | 20-40 | 10-20 |

Example 109

Representative Aminoglycoside Compounds

The following compounds were prepared using methods illustrated in the previous examples. The compounds were examined in standard bacterial assays against E. Coli and S. Aureus to determine activities. If present, "N.D." indicates "no data".

| Compound# | MIC (uM) E. Coli. | S. Aureus |
|---|---|---|
| 15g | 2.5-5 | 0.6-1.2 |
| 15k | 2.5-5 | 0.3-0.6 |
| 15l | 0.6-1.2 | 0.3-0.6 |
| 15r | 1.3-2.5 | 0.3-0.6 |
| 15v | 1.3-2.5 | 0.3-0.6 |
| 15n | 1.3-2.5 | 0.3-0.6 |
| 15p | 1.3-2.5 | 0.2-0.3 |
| 15t | 5-10 | 0.6-1.2 |
| 15m | 1.3-2.5 | 0.3-0.6 |
| 15s | 1.3-2.5 | 0.3-0.6 |

-continued

| Compound# | MIC (uM) E. Coli. | S. Aureus |
|---|---|---|
| 15w | 1.3-2.5 | 1.3-2.5 |
| 15x | 1.3-2.5 | 0.3-0.6 |
| 15q | 1.3-2.5 | 0.3-0.6 |
| 15n | 0.6-1.2 | 0.2-0.3 |
| 15o | 0.6-1.2 | 0.2-0.3 |
| 15z | 1.3-2.5 | 0.3-0.6 |
| 15aa | 1.3-2.5 | 0.3-0.6 |
| 15y | 1.3-2.5 | 0.3-0.6 |

Example 110

Representative Aminoglycoside Compounds

The following compounds were prepared using methods illustrated in the previous examples. The compounds were also examined in standard bacterial assays against *E. Coli, S. Aureus, P. aurginosa, K. pneumoniae, P. vulgaris*, and *A. baumannii* to determine activities. Each of the bacterial cultures that are available from ATCC (www.atcc.org) is identified by its ATCC number. *A. baumannii* is gentamicin sensitive *Acinetobacter baumannii* #2 from Walter Reed.

| | MIC (uM) | | | | | | |
|---|---|---|---|---|---|---|---|
| Compound# | E. coli ATCC 25922 | S. aureus ATCC 13709 | P. aurginosa ATCC 25416 | P. aurginosa ATCC 29248 | K. pneumoniae ATCC 10031 | P. vulgaris ATCC 8427 | A. baumannii WReed 2 |
| 9p - sample 1 | 5-10 | 10-20 | >40 | >40 | 1.3-2.5 | 2.5-5 | 2.5-5 |
| 9p - sample 2 | >40 | 1.2-2.5 | >40 | >40 | >40 | 20-40 | >40 |
| 15j | 1.3-2.5 | 10-20 | >40 | >40 | <0.6 | 1.3-2.5 | 1.3-2.5 |
| 9ae | >40 | 10-20 | 5-10 | >40 | 5-10 | 20-40 | 20-40 |
| 67 | 2.5-5 | 20-40 | 1.3-2.5 | 5-10 | 0.6-1.3 | 5-10 | 2.5-5 |
| 46a | 0.6-1.3 | 0.6-1.2 | 0.6-1.3 | 1.3-2.5 | <0.6 | 0.6-1.3 | 0.6-1.3 |
| 46b | 5-10 | 1.2-2.5 | 1.3-2.5 | 5-10 | 1.3-2.5 | 5-10 | 2.5-5 |
| 9ag | 10-20 | 0.6-1.2 | 10-20 | >40 | 2.5-5 | 10-20 | 10-20 |
| 9aj | 5-10 | <0.6 | >40 | >40 | 1.3-2.5 | 5-10 | 2.5-5 |
| 9ai | 5-10 | 1.2-2.5 | 2.5-5 | 20-40 | 2.5-5 | 5-10 | 10-20 |

Example 111

Representative Aminoglycoside Compounds

The following compounds were prepared using methods illustrated in the previous examples. The compounds were also examined in standard bacterial assays against *E. Coli, S. Aureus, P. aurginosa, K. pneumoniae, P. vulgaris*, and *A. baumannii* to determine activities. Each of the bacterial cultures that are available from ATCC (www.atcc.org) is identified by its ATCC number. *A. baumannii* is gentamicin sensitive *Acinetobacter baumannii* #2 from Walter Reed.

| | MIC (uM) | | | | | | |
|---|---|---|---|---|---|---|---|
| Compound# | E. coli ATCC 25922 | S. aureus ATCC 13709 | P. aurginosa ATCC 25416 | P. aurginosa ATCC 29248 | K. pneumoniae ATCC 10031 | P. vulgaris ATCC 8427 | A. baumannii WReed 2 |
| Paromomycin | 5-10 | 10-20 | >40 | >40 | 0.6-1.3 | >40 | 2.5-5 |
| 15j | 1.3-2.5 | 0.3-0.6 | >40 | >40 | 0.6-1.3 | >40 | 20-40 |
| 15l | 1.3-2.5 | 0.2-0.3 | >40 | >40 | 0.6-1.3 | >40 | 10-20 |
| 15u | 1.3-2.5 | 0.3-0.6 | >40 | >40 | 0.6-1.3 | >40 | 10-20 |
| 15o | 1.3-2.5 | 0.3-0.6 | >40 | >40 | 0.6-1.3 | >40 | 10-20 |
| 9p - sample 1 | 5-10 | 0.6-1.3 | >40 | >40 | 2.5-5 | >40 | >40 |
| 67 | 5-10 | 1.3-2.5 | 10-20 | 5-10 | 0.6-1.3 | 2.5-5 | 5-10 |
| 46a | 1.3-2.5 | 0.2-0.3 | 10-20 | 5-10 | 0.3-0.6 | 5-10 | 10-20 |
| 39 | 2.5-5 | 0.6-1.3 | >40 | >40 | 1.3-2.5 | >40 | 20-40 |

Example 112

Representative Aminoglycoside Compounds

The following compound was prepared using methods illustrated in the previous examples. The compound was also examined in standard bacterial assays against *E. Coli, S. Aureus, P. aurginosa, K. pneumoniae* and *A. baumannii* to determine activities. Each of the bacterial cultures that are available from ATCC (www.atcc.org) is identified by its ATCC number.

| | MIC (uM) | | | | |
|---|---|---|---|---|---|
| Compound# | *E. coli* ATCC 25922 | *S. aureus* ATCC 29213 | *P. aurginosa* ATCC 27853 | *K. pneumoniae* ATCC 10031 | *A. baumannii* ATCC 19606 |
| 87 | <16 | <16 | <16 | <16 | <16 |

Example 113

*Staphylococcus aureus* (Smith Strain ATCC 13709) Mouse Protection Assay

Two of the novel aminoglycoside compounds of the invention were examined for their anitbacterial activity against *staphylococcus aureus*. Mice were fed with autoclaved commercial food pellets and sterile water ad libitum. Animals were inoculated intraperitoneally with 0.5 mL/mouse of the indicated concentration of *S. aureus* (ATCC 13709) containing 10% mucin. There were 10 mice in each treatment group and compounds were administered subcutaneously one and 3 hour after infection. Compounds 15a ($R_4=R_5=CH_3$) and 15j ($R_4=H, R_5=(CH_2)_2C_6H_5$)) were used at 75 mg/kg, 37.5 mg/kg, 18.8 mg/kg, 9.4 mg/kg, 4.7 mg/kg, 2.3 mg/kg, 1.17 mg/kg and 0.5 mg/kg. Amakacin, paromomycin and neomycin were used as the positive controls at concentrations of 2 mg/kg, 1 mg/kg and 0.5 mg/kg.

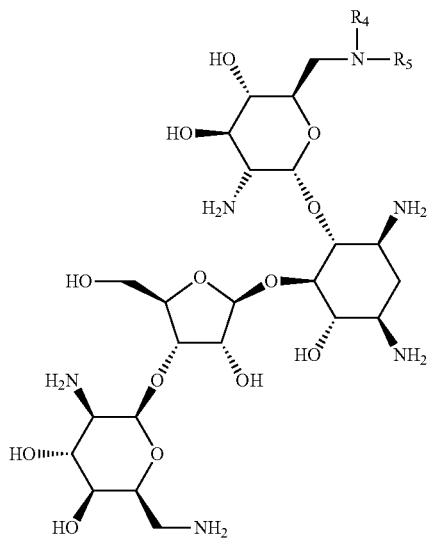

| Staph Conc. | Antibiotic conc. | # Dead mice/Total mice in group |
|---|---|---|
| $10^9$ | 0 | 5/5 (10% Mucin) |
| $10^8$ | 0 | 5/5 (10% Mucin) |
| $10^7$ | 0 | 1/5 (10% Mucin) |
| $10^6$ | 0 | 0/5 (10% Mucin) |
| 0 | 0 | 0/10 (10% Mucin) |
| $10^6$ | 0 | 9/10 (10% Mucin) |
| $10^7$ | 0 | 9/10 (10% Mucin) |
| $10^6$ | Amikacin 2 mg/kg | 8/10 (10% Mucin) |
| $10^6$ | Amikacin 1 mg/kg | 10/10 (10% Mucin) |
| $10^6$ | Amikacin 0.5 mg/kg | 8/10 (10% Mucin) |
| $10^6$ | Paromomycin 2 mg/kg | 9/10 (10% Mucin) |
| $10^6$ | Paromomycin 1 mg/kg | 10/10 (10% Mucin) |
| $10^6$ | Paromomycin 0.5 mg/kg | 10/10 (10% Mucin) |
| $10^6$ | Neomycin 2 mg/kg | 4/10 (10% Mucin) |
| $10^6$ | Neomycin 1 mg/kg | 10/10 (10% Mucin) |
| $10^6$ | Neomycin 0.5 mg/kg | 7/10 (10% Mucin) |
| $10^6$ | 15a 75 mg/kg | 0/10 (10% Mucin) |
| $10^6$ | 15a 37 mg/kg | 0/10 (10% Mucin) |
| $10^6$ | 15a 18 mg/kg | 0/10 (10% Mucin) |
| $10^6$ | 15a 9 mg/kg | 0/10 (10% Mucin) |
| $10^6$ | 15a 4.5 mg/kg | 1/10 (10% Mucin) |
| $10^6$ | 15a 2 mg/kg | 7/10 (10% Mucin) |
| $10^6$ | 15a 1 mg/kg | 7/10 (10% Mucin) |
| $10^6$ | 15a 0.5 mg/kg | 8/10 (10% Mucin) |
| $10^6$ | 15j 75 mg/kg | 0/10 (10% Mucin) |
| $10^6$ | 15j 37 mg/kg | 0/10 (10% Mucin) |
| $10^6$ | 15j 18 mg/kg | 0/10 (10% Mucin) |
| $10^6$ | 15j 9 mg/kg | 0/10 (10% Mucin) |
| $10^6$ | 15j 4.5 mg/kg | 0/10 (10% Mucin) |
| $10^6$ | 15j 2 mg/kg | 0/10 (10% Mucin) |
| $10^6$ | 15j 1 mg/kg | 0/10 (10% Mucin) |
| $10^6$ | 15j 0.5 mg/kg | 7/10 (10% Mucin) |

In a similar experiment, compounds 9p ($R_6=CH_2C_6H_5$) and 9b ($R_6=$3-pyridyl) were used at 75 mg/kg, 37 mg/kg, 18 mg/kg, 9 mg/kg, 4.5 mg/kg, 2 mg/kg, 1 mg/kg, 0.5 mg/kg, 0.25 mg/kg, and 0.1 mg/kg in the *staphylococcus aureus* protection assay. Test compound was administered as an aqueous buffer solution (phosphate buffered saline (PBS), pH=7.4). The data in the table below clearly indicate that both 9p and 9b are effective at preventing lethal bacterial infections in mice, with 9p being protective at doses as small as 0.25 mg/kg.

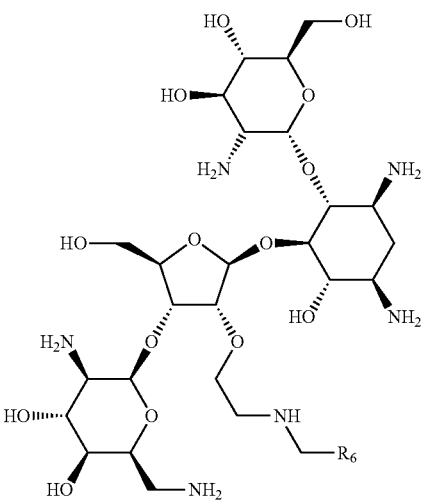

| Staph Conc. | Antibiotic conc. | # Dead mice/Total mice in group |
|---|---|---|
| $10^6$ | 9p 75 mg/kg | 0/10 (10% Mucin) |
| $10^6$ | 9p 37 mg/kg | 0/10 (10% Mucin) |
| $10^6$ | 9p 18 mg/kg | 0/10 (10% Mucin) |
| $10^6$ | 9p 9 mg/kg | 0/10 (10% Mucin) |
| $10^6$ | 9p 4.5 mg/kg | 0/10 (10% Mucin) |
| $10^6$ | 9p 2 mg/kg | 0/10 (10% Mucin) |
| $10^6$ | 9p 1 mg/kg | 0/10 (10% Mucin) |
| $10^6$ | 9p 0.5 mg/kg | 0/10 (10% Mucin) |
| $10^6$ | 9p 0.25 mg/kg | 1/10 (10% Mucin) |
| $10^6$ | 9p 0.1 mg/kg | 5/10 (10% Mucin) |
| $10^6$ | 9b 75 mg/kg | 0/10 (10% Mucin) |
| $10^6$ | 9b 37 mg/kg | 0/10 (10% Mucin) |
| $10^6$ | 9b 18 mg/kg | 0/10 (10% Mucin) |
| $10^6$ | 9b 9 mg/kg | 0/10 (10% Mucin) |
| $10^6$ | 9b 4.5 mg/kg | 0/10 (10% Mucin) |
| $10^6$ | 9b 2 mg/kg | 0/10 (10% Mucin) |
| $10^6$ | 9b 1 mg/kg | 0/10 (10% Mucin) |
| $10^6$ | 9b 0.5 mg/kg | 3/10 (10% Mucin) |
| $10^6$ | 9b 0.25 mg/kg | 6/10 (10% Mucin) |
| $10^6$ | 9b 0.1 mg/kg | 7/10 (10% Mucin) |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

What is claimed is:

1. A pharmaceutical composition comprising a pharmaceutically acceptable carrier or excipient and a compound having the following formula VI:

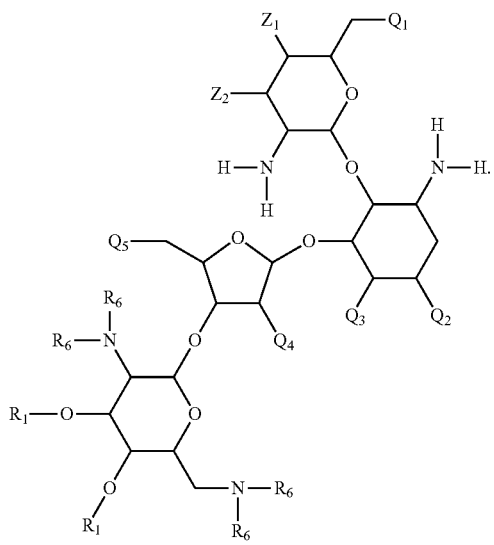

or a prodrug or pharmaceutically acceptable salt thereof, wherein:

$Q_1$ is $-NR_{10}R_{11}$;
$Q_2$ is

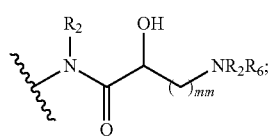

each $Q_3$ and $Q_4$ is $-OR_7$,
$Q_5$ is $-OR_8$;
each of $R_1$, $R_6$, $R_7$ and $R_8$ is, in each instance, H;
each $R_2$ and $R_{10}$ is, independently, H, $C_1$-$C_{12}$ alkyl or substituted $C_1$-$C_{12}$ alkyl;
$R_{11}$ is cyano, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or $-(CH_2)_n$-$(L_1)_m$-$(CH_2)_{nn}$-$E_1$;
$L_1$ is S, O or $NJ_1$;
n is an integer from 1 to 8;
m is 0 or 1;
nn is 0 or an integer from 1 to 8;
mm is 1 or 2;
$E_1$ is H, hydroxyl, halogen, cyano, $-NJ_1J_2$, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heteroaryl, substituted heteroaryl, a heterocyclic radical, a substituted heterocyclic radical or a substituted or unsubstituted mono or poly cyclic structure that is unsaturated, partially saturated or fully saturated and optionally includes one or more heteroatoms selected from O, N and S;
each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, $-C(=O)-X$, a heterocyclic radical or a substituted heterocyclic radical;
each X is, independently, H, $C_1$-$C_{12}$ alkyl or substituted $C_1$-$C_{12}$ alkyl; and
$Z_1$ and $Z_2$ are each, independently, H or $-OH$.

2. A pharmaceutical composition according to claim 1, wherein mm is 1.

3. A pharmaceutical composition according to claim 1, wherein mm is 2.

4. A pharmaceutical composition according to claim 1, wherein each $R_2$ is H.

5. A pharmaceutical composition according to claim 1, wherein $Z_1$ is —OH.

6. A pharmaceutical composition according to claim 1, wherein $R_{10}$ is H.

7. A pharmaceutical composition according to claim 6, wherein $R_{11}$ is substituted $C_1$-$C_{12}$ alkyl.

8. A pharmaceutical composition according to claim 1, wherein:
$R_{10}$ is H;
$R_{11}$ is substituted $C_1$-$C_{12}$ alkyl;
each $R_2$ is H; and
$Z_1$ is —OH.

9. A pharmaceutical composition according to claim 1, wherein said compound of formula VI has the configuration:

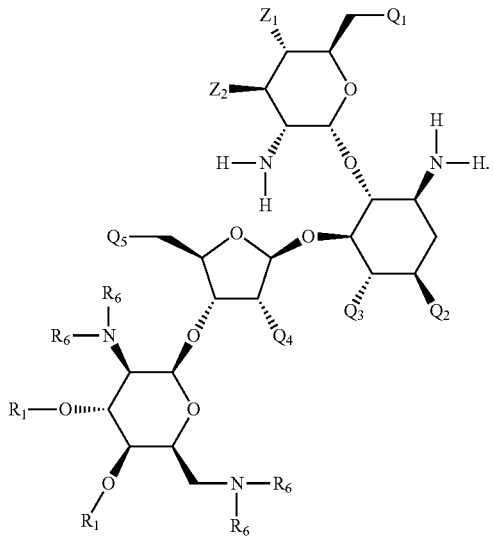

10. A pharmaceutical composition according to claim 9, wherein mm is 1.

11. A pharmaceutical composition according to claim 9, wherein mm is 2.

12. A pharmaceutical composition according to claim 9, wherein each $R_2$ is H.

13. A pharmaceutical composition according to claim 9, wherein $Z_1$ is —OH.

14. A pharmaceutical composition according to claim 9, wherein $R_{10}$ is H.

15. A pharmaceutical composition according to claim 14, wherein $R_{11}$ is substituted $C_1$-$C_{12}$ alkyl.

16. A pharmaceutical composition according to claim 9, wherein:
$R_{10}$ is H;
$R_{11}$ is substituted $C_1$-$C_{12}$ alkyl;
each $R_2$ is H; and
$Z_1$ is —OH.

17. A pharmaceutical composition according to claim 16, wherein mm is 1.

18. A pharmaceutical composition according to claim 16, wherein mm is 2.

19. A pharmaceutical composition comprising a pharmaceutically acceptable carrier or excipient and a compound having the following formula I:

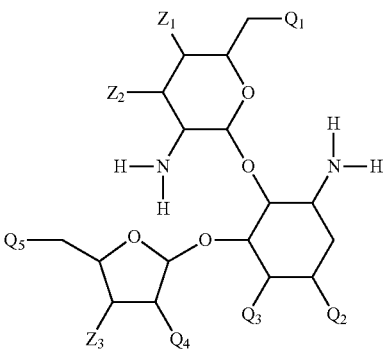

or a stereoisomer, prodrug or pharmaceutically acceptable salt thereof,
wherein:
$Q_1$ is azido or —$NR_{10}R_{11}$;
$Q_2$ is —$NR_{10}R_{12}$;
each $Q_3$ and $Q_4$ is —$OR_7$;
$Q_5$ is H, halogen, cyano, azido, —$OR_8$, —$NR_2R_3$, a protected amino group or a nitrogen containing heterocyclic radical which optionally includes one or more additional heteroatoms selected from N, O and S wherein the heterocyclic radical is covalently linked through said nitrogen atom;
each $R_1$ is, independently, H or a hydroxyl protecting group;
each $R_2$ is, independently, H, an amino protecting group, $C_1$-$C_{12}$ alkyl or substituted $C_1$-$C_{12}$ alkyl;
each $R_3$ is, independently, H, an amino protecting group, cyano, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$—$(CH_2)_{nn}$-$E_1$;
each $R_6$ is, independently, H or an amino protecting group;
each $R_7$ is, independently, H, a hydroxyl protecting group or —$(CH_2)_n$-$(L_1)_m$-$(CH_2)_{nn}$-$E_1$;
$R_8$ is H, a hydroxyl protecting group, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$—$(CH_2)_{nn}$-$E_1$;
each $R_{10}$ is, independently, H, $C_1$-$C_{12}$ alkyl or substituted $C_1$-$C_{12}$ alkyl;
each $R_{11}$ is, independently, cyano, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or —$(CH_2)_n$-$(L_1)_m$—$(CH_2)_{nn}$-$E_1$; and
$R_{12}$ is a group having the following formula III:

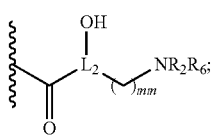

each $L_1$ is, independently, S, O or $NJ_1$;

$L_2$ is CH or N;

each n is, independently, an integer from 1 to 8;

each m is, independently, 0 or 1;

each nn is, independently, 0 or an integer from 1 to 8;

mm is 1 or 2;

each $E_1$ is, independently, H, hydroxyl, halogen, cyano, $-NJ_1J_2$, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heteroaryl, substituted heteroaryl, a heterocyclic radical, a substituted heterocyclic radical or a substituted or unsubstituted mono or poly cyclic structure that is unsaturated, partially saturated or fully saturated and optionally includes one or more heteroatoms selected from O, N and S;

each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, $-C(=O)-X$, a heterocyclic radical or a substituted heterocyclic radical;

each X is, independently, H, $C_1$-$C_{12}$ alkyl or substituted $C_1$-$C_{12}$ alkyl;

each $Z_1$ and $Z_2$ is, independently, H, hydroxyl or a protected hydroxyl; and $Z_3$ is a group having the following formula IV:

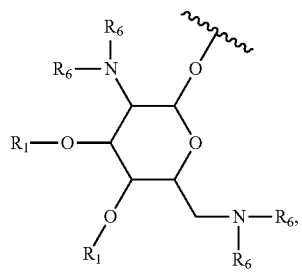

IV and wherein when $Q_2$ is $-N(H)C(=O)C(H)(OH)CH_2CH_2NH_2$ then $Q_1$ is other than $-N(H)CH_3$ or $-N(H)CH_2CH_3$ and $Q_5$ is other than $-N(H)C(=NH)NH_2$ or $-N(H)CH=NH_2$.

20. A pharmaceutical composition according to claim 19, wherein one of $Z_1$ and $Z_2$ is H.

21. A pharmaceutical composition according to claim 19, wherein:

each of said substituted groups, is, independently, mono or poly substituted with optionally protected substituent groups independently selected from $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl or substituted $C_5$-$C_{20}$ aryl, heterocyclic radical, substituted heterocyclic radical, heteroaryl, substituted heteroaryl, $C_5$-$C_7$ alicyclic radical, substituted $C_5$-$C_7$ alicyclic radical, halogen, $-OJ_3$, $-NJ_1J_2$, $-SJ_3$, $-N_3$, $-COOH$, $-C(=O)-X$, $-CN$, $-S(=O)_2-X$, $-S(=O)-X$, $-C(=O)-NJ_1J_2$, $-N(H)C(=O)-J_1$, $-N(J_1)-(CH_2)_{nm}-OJ_3$ and $-N(J_1)-(CH_2)_{nm}-NJ_1J_2$ and a substituted or unsubstituted mono or poly cyclic structure that is unsaturated, partially saturated or fully saturated and optionally includes one or more heteroatoms selected from O, N and S;

each $J_3$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ aminoalkyl, substituted $C_1$-$C_{12}$ aminoalkyl or a hydroxyl protecting group; and nm is an integer from 1 to 20.

22. A pharmaceutical composition according to claim 19, wherein said compound of formula I has the configuration:

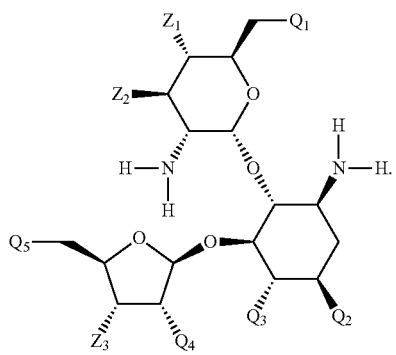

23. A pharmaceutical composition according to claim 19, wherein said compound of formula I has the configuration:

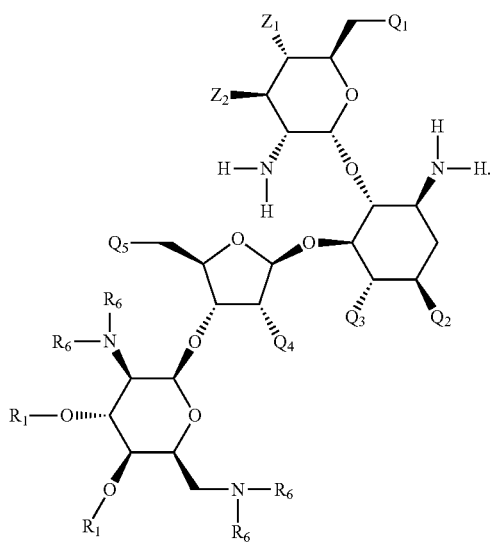

24. A pharmaceutical composition according to claim 8, wherein mm is 1.

25. A pharmaceutical composition according to claim 8, wherein mm is 2.

* * * * *